US009982301B2

(12) United States Patent
Muthukumar et al.

(10) Patent No.: US 9,982,301 B2
(45) Date of Patent: May 29, 2018

(54) URINE MRNA PROFILE AND ACUTE DYSFUNCTION OF KIDNEY ALLOGRAFT

(71) Applicant: Cornell University, Ithaca, NY (US)

(72) Inventors: Thangamani Muthukumar, New York, NY (US); Manikkam Suthanthiran, Scarsdale, NY (US); Ruchuang Ding, Beechurst, NY (US)

(73) Assignee: Cornell University, Ithaca, NY (US)

( * ) Notice: Subject to any disclaimer, the term of this patent is extended or adjusted under 35 U.S.C. 154(b) by 122 days.

(21) Appl. No.: 14/591,542

(22) Filed: Jan. 7, 2015

(65) Prior Publication Data

US 2015/0191787 A1 Jul. 9, 2015

Related U.S. Application Data

(60) Provisional application No. 61/924,543, filed on Jan. 7, 2014.

(51) Int. Cl.
*C12Q 1/68* (2018.01)
*C12P 19/34* (2006.01)

(52) U.S. Cl.
CPC ...... *C12Q 1/6883* (2013.01); *C12Q 2600/112* (2013.01); *C12Q 2600/118* (2013.01); *C12Q 2600/158* (2013.01)

(58) Field of Classification Search
CPC .................. C12Q 2600/158; C12Q 2600/112
See application file for complete search history.

(56) References Cited

U.S. PATENT DOCUMENTS

| 6,187,534 | B1 | 2/2001 | Strom et al. |
| 6,900,015 | B2 | 5/2005 | Avihingsanon et al. |
| 2003/0113744 | A1* | 6/2003 | O'Toole ............. A61K 38/1709 435/6.14 |
| 2004/0053284 | A1 | 3/2004 | Andrus et al. |
| 2006/0088836 | A1 | 4/2006 | Wohlgemuth et al. |
| 2007/0031890 | A1 | 2/2007 | Wohlgemuth et al. |
| 2008/0131441 | A1 | 6/2008 | Suthanthiran |
| 2013/0012860 | A1 | 1/2013 | Suthanthiran et al. |
| 2014/0213533 | A1 | 7/2014 | Suthanthiran et al. |

FOREIGN PATENT DOCUMENTS

| EP | 0534858 A1 | 3/1993 |
| WO | WO-2011112719 A1 | 9/2011 |

OTHER PUBLICATIONS

Anglicheau, D. et al. Transplantation & vol. 93, No. 11, Jun. 15, 2012, p. 1136-1146.*
Dressing, M.C. et al. Nephrol Dial Transplant (2010) 25: 4087-4092.*
Docherty, N.G. et al. Nephrol Dial Transplant (2006) 21: 2106-2119.*
Matignon, M. et al. J Am Soc Nephrol 25:printed pp. 1-12, 2014.*
Bolstad, B.M. et al. Bioinformatics, vol. 19 No. 2 (2003) pp. 185-193.*
Hoshikawa Y. et al., Physiol Genomics 12: 209-219, 2003.*
Cheung V.G. et al., Nature Genetics, vol. 33, Mar. 2003, p. 422-425.*
Dany Anglicheau et al. Transplantation. Jun. 15, 2012; 93(11): 1136-1146, Supplementary Digital Content, pp. 1-10.*
"U.S. Appl. No. 13/583,750, Final Office Action dated Jul. 30, 2014", 14 pgs.
"U.S. Appl. No. 13/583,750, Non Final Office Action dated Mar. 3, 2014", 14 pgs.
"U.S. Appl. No. 13/583,750, Preliminary Amendment filed Sep. 10, 2012", 3 pgs.
"U.S. Appl. No. 13/583,750, Response filed Feb. 12, 2014 to Restriction Requirement dated Nov. 12, 2013", 8 pgs.
"U.S. Appl. No. 13/583,750, Response filed Jul. 1, 2014 to Non Final Office Action dated Mar. 3, 2014", 13 pgs.
"U.S. Appl. No. 13/583,750, Response filed Oct. 30, 2014 to Final Office action dated Jul. 30, 2014", 13 pgs.
"U.S. Appl. No. 13/583,750, Restriction Requirement dated Nov. 12, 2013", 9 pgs.
"U.S. Appl. No. 14/170,132, Final Office Action dated Aug. 9, 2016", 10 pgs.
"U.S. Appl. No. 14/170,132, Non Final Office Action dated Jan. 29, 2016", 8 pgs.
"U.S. Appl. No. 14/170,132, Response filed Apr. 27, 2016 to Non Final Office Action dated Jan. 29, 2016", 8 pgs.
"U.S. Appl. No. 14/170,132, Response filed Sep. 25, 2015 to Restriction Requirement dated Jul. 28, 2015", 6 pgs.
"U.S. Appl. No. 14/170,132, Response filed Nov. 9, 2016 to Final Office Action dated Aug. 9, 2016", 6 pgs.
"U.S. Appl. No. 14/170,132, Restriction Requirement dated Jul. 28, 2015", 7 pgs.
"International Application Serial No. PCT/US11/27754, International Preliminary Report on Patentability dated Sep. 11, 2012", 6 pgs.
"International Application Serial No. PCT/US11/27754, International Search Report dated May 18, 2011", 3 pgs.
"International Application Serial No. PCT/US11/27754, Written Opinion dated May 18, 2011", 5 pgs.
Afaneh, C., et al., "Urinary Cell Levels of mRNA for OX40, OX40L, PD-1, PD-L1 OR PD-L2 and Acute Rejection of Human Renal Allografts", Transplantation, 90(12), (2010), 14 pgs.
Anglicheau, D., et al., "Noninvasive Prediction of Organ Graft Rejection and Outcome Using Gene Expression Patterns", Transplantation, 86(2), (2008), 192-199.
Aquino-Dias, E. C., et al., "Non-invasive diagnosis of acute rejection in kidney transplants with delayed graft function", Kidney International 73(7), (2008), 877-8 84.
Chen, G., et al., "Discordant Protein and mRNA Expression in Lung Adenocarcinomas", Molecular & Cellular Proteomics 1(4), (2002), 304-313.
Cobb, J P, et al., "Sepsis gene expression profiling: Murine splenic compared with hepatic responses determined by using complementary DNA microarrays", Crit Care Med, 30(12), (2002), 2711-2721.

(Continued)

Primary Examiner — Stephen T Kapushoc
(74) Attorney, Agent, or Firm — Schwegman Lundberg & Woessner, P.A.

(57) ABSTRACT

Non-invasive methods for detecting, predicting, and/or monitoring differential diagnosis of kidney transplant dysfunction in kidney transplant patients are described.

4 Claims, 9 Drawing Sheets

(56) References Cited

OTHER PUBLICATIONS

Dadhania, D., et al., "Molecular signatures of urinary cells distinguish acute rejection of renal allografts from urinary tract infection", (Abstract Only), Transplantation, 75(10), 1752-1754, (2003), 1 pg.

Ding, R., et al., "CD102 mRNA Levels in Urinary Cells Predict Acute Rejection of Renal Allografts", Transplantation, 75(8), (2003), 1307-1312.

Ding, R., et al., "Noninvasive Diagnosis of BK Virus Nephritis by Measurement of Messenger RNA for BK Virus VP1 in Urine", Transplantation, 74(7), (2002), 987-994.

Flechner, S. M., et al., "Kidney Transplant Rejection and Tissue Injury by Gene Profiling of Biopsies and Peripheral Blood Lymphocytes", American Journal of Transplantation, 4(9), (2004), 1475-4489.

Gibson, U. E., et al., "A Novel Method for Real Time Quantitative RT-PCR", Genome Research, 6(10), (1996), 995-1001.

Heid, C. A., et al., "Real Time Quantitative PCR", Genome Research, 6(10), (1996), 986-994.

Hsieh, M.-F., et al., "Both CXCR3 and CXCL10/1FN-Inducible Protein 10 Are Required for Resistance to Primary Infection by Dengue Virus", J Immunol, 177, (2006), 1855-1863.

Kotsch, K., et al., "Enhanced granulysin mrna expression in urinary sediment in early and delayed acute renal allograft rejection", Transplantation, 77(12), (2004), 1866-1875.

Li, B., et al., "Noninvasive Diagnosis of Renal-Allograft Rejection by Measurement of Messenger RNA for Perforin and Granzyme B in Urine", The New England Journal of Medicine, 344(13), (2001), 947-954.

Muthukumar, T., et al., "Messenger RNA for FOXP3 in the Urine of Renal-Allograft Receipients", New England Journal of Medicine, 353(22), (2005), 2342-2351.

Muthukumar, T., et al., "Serine Proteinase Inhibitor-9, an Endogenous Blocker of Granzyme B/Perforin Lytic Pathway, is Hyperexpressed During Acute Rejection of Renal Allografts", Transplantation, 75(9), (2003), 1565-1570.

Prashar, Y., et al., "Analysis of differential gene expression by display of 3' end restriction fragments of cDNA's", Proc. Natl. Acad. Sci. USA, 93(2), (Jan. 1996), 659-663.

Tatapudi, R. R., et al., "Noninvasive detection of renal allograft inflammation by measurements of mRNA for IP-10 and CXCR3 in urine", Kidney International, 65(6), (2004), 2390-2397.

Tyagi, S., et al., "Beacons of Light", Nature Biotechnology, 24(3), (1996), 303-304.

Velculescu, V. E., et al., "Serial Analysis of Gene Expression", Science, 270(5235), (1995), 484-487.

Zhang, Z., et al., "A Linear Regression Framework for Receiver Operating Characteristics (ROC) Curve Analysis", University of Washington Biostatistics Working Paper Series, (2005), 23 pgs.

"U.S. Appl. No. 14/170,132, Notice of Allowance dated May 5, 2017", 9 pgs.

"ASN Presentation—Differential Diagnosis of Acute Kidney Allograft Dysfunction Using Urinary Cell mRNA Profiles", Draft of the oral presentation at the American Society of Nephrology Kidney Week 2013, Nov. 5-10, 2013, Atlanta, GA, (2013), 12 pgs.

"ASN-Abstract", Abstract submitted for the American Society of Nephrology Kidney Week 2013, Nov. 5-10, 2013, Atlanta, GA, (2013), 2 pgs.

"ATC Presentation", Draft of the poster presented at the American Transplant Congress 2012, Jun. 2-6, Boston, MA, (2012), 13 pgs.

"ATC—Abstract", Abstract submitted for the American Transplant Congress 2012, Jun. 2-6, Boston, MA, (2012), 275-276.

Matignon, Marie, et al., "Urinary Cell mRNA Profiles and Differential Diagnosis of Acute Kidney Graft Dysfunction", J Am Soc Nephrol 25, (2014), 1586-1597.

* cited by examiner

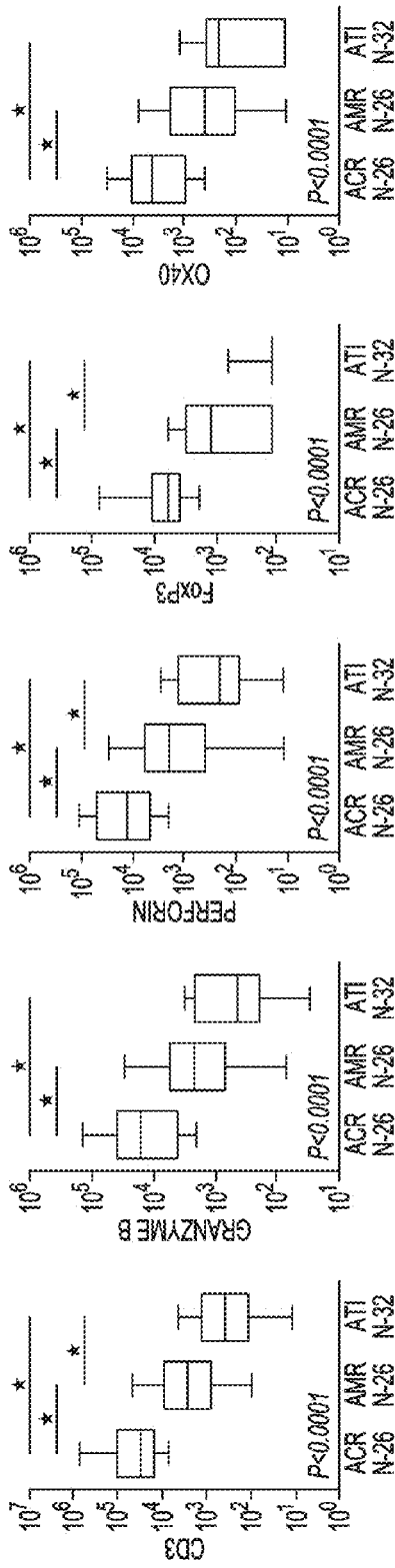
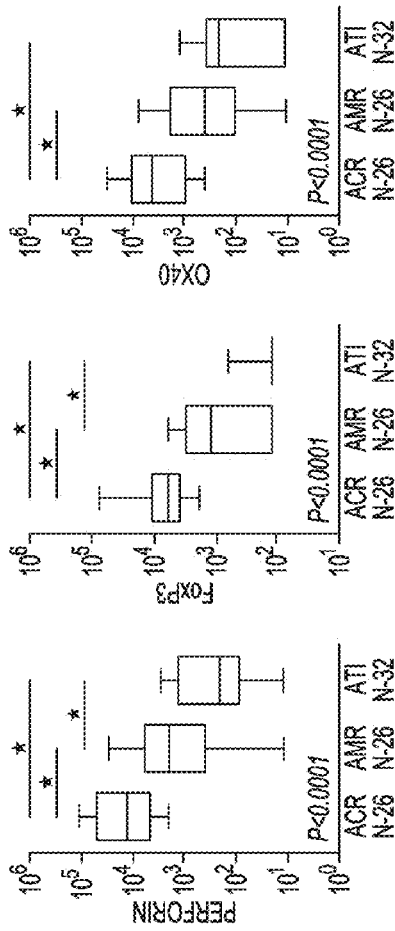
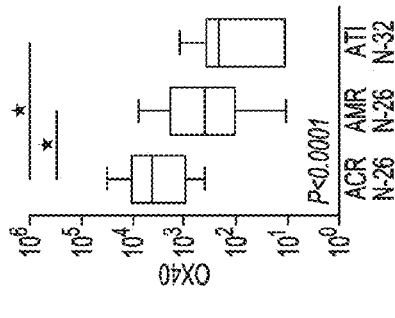
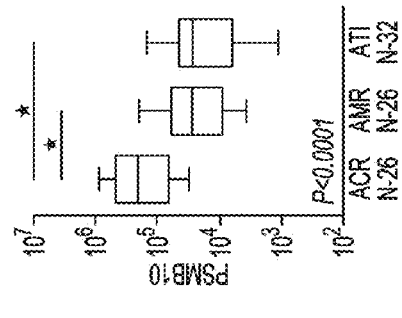

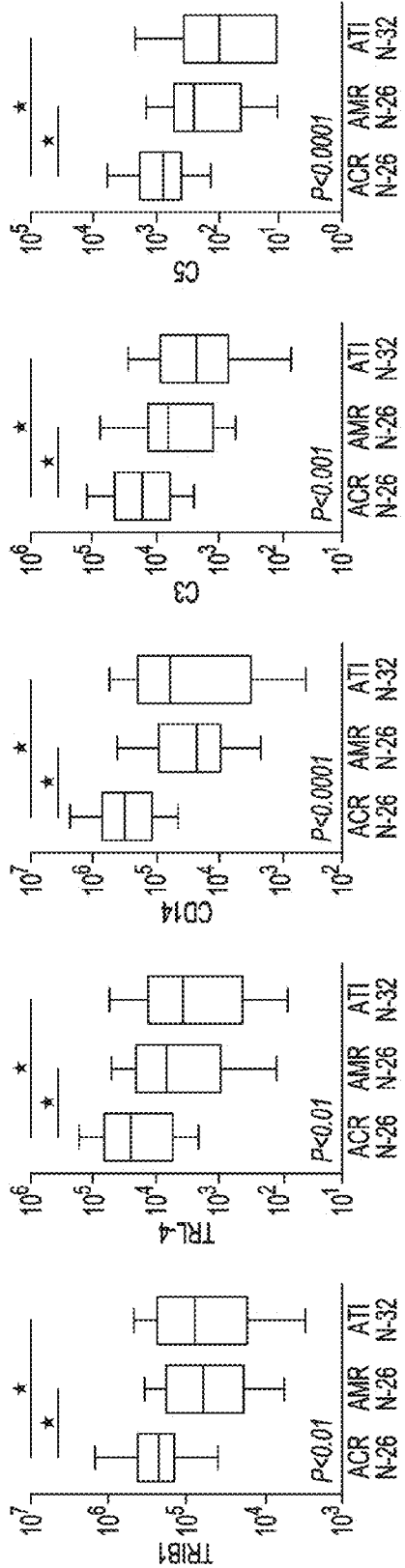
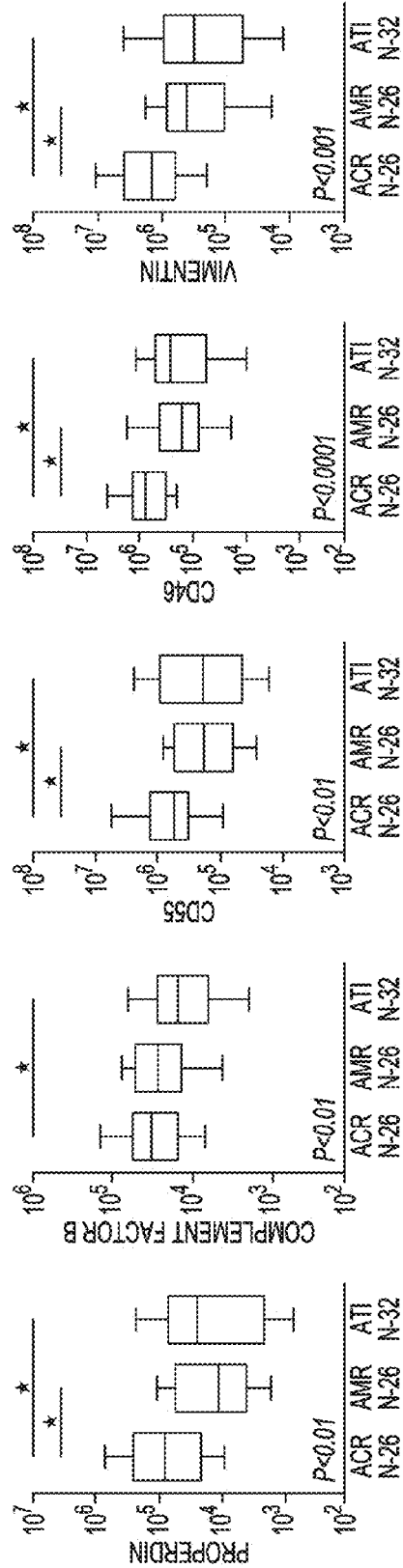

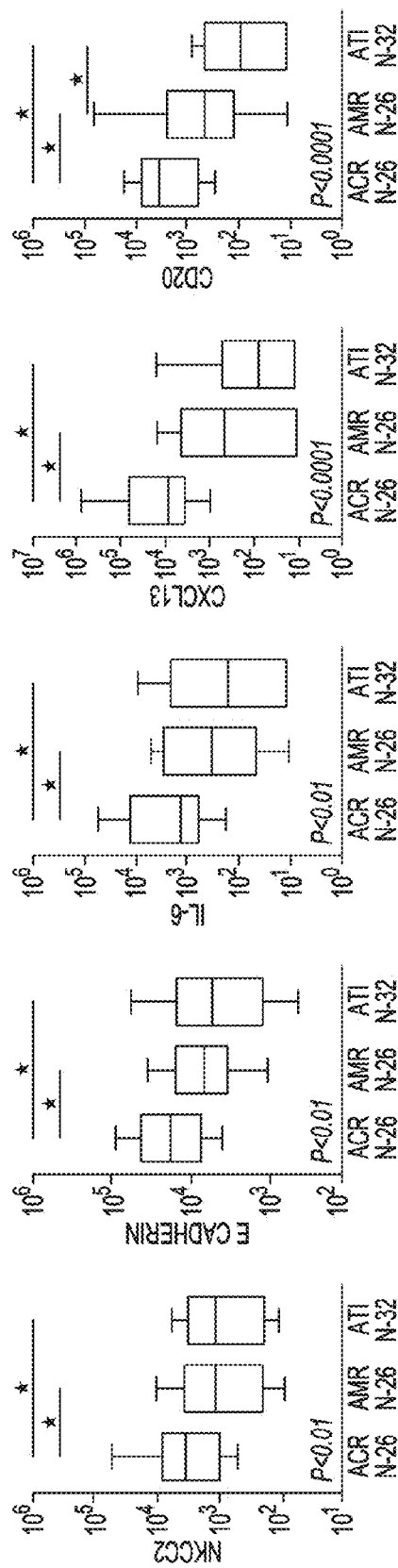
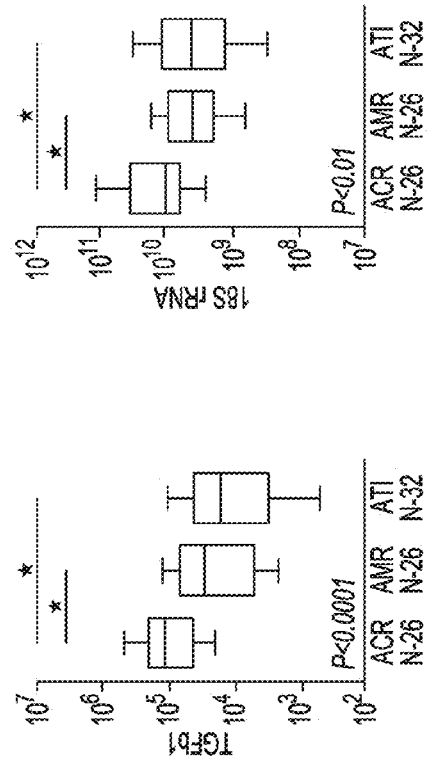

```
                           SEQUENCE LISTING

<160> NUMBER OF SEQ ID NOS: 90

<210> SEQ ID NO 1
<211> LENGTH: 2235
<212> TYPE: DNA
<213> ORGANISM: Homo sapiens
<220> FEATURE:
<223> OTHER INFORMATION: A synthetic oligonucleotide
<221> NAME/KEY: misc_feature
<222> LOCATION: (1)...(2235)
<223> OTHER INFORMATION: n = A,T,C or G

<400> SEQUENCE: 1
cgctgctcct cccgtcgccg tccgggcccg tccgtccgtc cgtccgtcgt cctcctcgct      60
nnnncggggc gccgggcccg tcctcacngg cccccgnnnn ngtccnggcc cgtcggggcc     120
tcgccgcgct ctaccttacc tacctggttg atcctgccaa tagcatatgc ttgtctcaaa     180
gattaagcca tgcatgtcta agtacgcacg gccggtacag tgaaactgcg aatggctcat     240
taaatcagtt atggttcctt tggtcgctcg ctcctctcct acttggataa ctgtggtaat     300
tctagagcta atacatgccg acgggcgctg acccccttcg cggggggat gcgtgcattt      360 atcagatcaa aaccaacccg gtcagcccct ctccggcccc ggccggggg cgggcgccgg      420 cggctttggt gactctagat aacctcgggc cgatcgcacg ccccccgtgg cggcgacgac     480
ccattcgaac gtctgcccta tcaactttcg atggtagtcg ccgtgcctac catggtgacc     540
acgggtgacg gggaatcagg gttcgattcc ggagagggag cctgagaaac ggctaccaca     600
tccaaggaag gcagcaggcg cgcaaattac ccactcccga cccggggagg tagtgacgaa     660
aaataacaat acaggactct ttcgaggccc tgtaattgga atgagtccac tttaaatcct     720
ttaacgagga tccattggag ggcaagtctg gtgccagcag ccgcggtaat tccagctcca     780
atagcgtata ttaaagttgc tgcagttaaa aagctcgtag ttggatcttg ggagcgggcg     840
ggcggtccgc cgcgaggcga gccaccgccc gtccccgccc cttgcctctc ggcgcccct      900 cgatgctctt agctgagtgt cccgcgggc ccgaagcgtt tactttgaaa aaattagagt      960
gttcaaagca ggcccgagcc gcctggatac cgcagctagg aataatggaa taggaccgcg    1020
gttctatttt gttggttttc ggaactgagg ccatgattaa gagggacggc cggggcatt     1080 cgtattgcgc cgctagaggt gaaattcctt ggaccggcgc aagacggacc agagcgaaag    1140
catttgccaa gaatgttttc attaatcaag aacgaaagtc ggaggttcga agacgatcag    1200
ataccgtcgt agttccgacc ataaacgatg ccgaccggcg atgcggcggc gttattccca    1260
tgacccgccg ggcagcttcc gggaaaccaa agtctttggg ttccggggg agtatggttg     1320 caaagctgaa acttaaagga attgacgaa gggcaccacc aggagtggag cctgcggctt     1380
aatttgactc aacacgggaa acctcacccg gcccggacac ggacaggatt gacagattga    1440
tagctctttc tcgattccgt gggtggtggt gcatggccgt tcttagttgg tggagcgatt    1500
tgtctggtta attccgataa cgaacgagac tctggcatgc taactagtta cgcgaccccc    1560
gagcggtcgg cgtcccccaa cttcttagag ggacaagtgg cgttcagcca cccgagattg    1620
agcaataaca ggtctgtgat gcccttagat gtccggggct gcacgcgcgc tacactgact    1680
ggctcagcgt gtgcctaccc tacgccggca ggcgcgggta acccgttgaa ccccattcgt    1740
```

```
gatgggatc gggattgca attattcccc atgaacgagg aattcccagt aagtgcgggt    1800
cataagcttg cgttgattaa gtccctgccc tttgtacaca ccgcccgtcg ctactaccga    1860
ttggatggtt tagtgaggcc ctcggatcgg ccccgccggg gtcggccac ggccctggcg    1920 gagcgctgag aagacggtcg aacttgacta tctagaggag gtaaaagtcg taacaaggtt    1980
tccgtaggtg aacctgcgga aggatcatta acggagcccg gacggcggcc cgcggcggcg    2040
ccgcgccgcg cttccctccg cacacccacc ccccaccgc gacggcgcgt gcgggcgggg    2100
ccgtgcccgt tcgttcgctc gctcgttcgt tcgccgcccg gcccggccgc gagagccgag    2160
aactcgggag ggagacgggg gagagagaga gagagagaga gagagagaga gagagagaga    2220
gaaagaaggg cgtgt                                                     2235
```

<210> SEQ ID NO 2  
<211> LENGTH: 1534  
<212> TYPE: DNA  
<213> ORGANISM: Homo sapiens

<400> SEQUENCE: 2

```
tattgtcaga gtcctcttgt ttggccttct aggaaggctg tgggacccag ctttcttcaa      60
ccagtccagg tggaggcctc tgccttgaac gtttccaagt gaggtaaaac ccgcaggccc     120
agaggcctct ctacttcctg tgtggggttc agaaaccctc ctcccctccc agcctcaggt     180
gcctgcttca gaaaatgaag tagtaagtct gctggcctcc gccatcttag taaagtaaca     240
gtcccatgaa acaaagatgc agtcgggcac tcactggaga gttctgggcc tctgcctctt     300
atcagttggc gtttggggggc aagatggtaa tgaagaaatg ggtggtatta cacagacacc     360
atataaagtc tccatctctg gaaccacagt aatattgaca tgccctcagt atcctggatc     420
tgaaatacta tggcaacaca atgataaaaa cataggcggt gatgaggatg ataaaaacat     480
aggcagtgat gaggatcacc tgtcactgaa ggaattttca gaattggagc aaagtggtta     540
ttatgtctgc taccccagag gaagcaaacc agaagatgcg aacttttatc tctacctgag     600
ggcaagagtg tgtgagaact gcatggagat ggatgtgatg tcggtggcca caattgtcat     660
agtggacatc tgcatcactg ggggcttgct gctgctggtt tactactgga gcaagaatag     720
aaaggccaag gccaagcctg tgacacgagg agcgggtgct ggcggcaggc aaagggggaca     780 aaacaaggag aggccaccac ctgttcccaa cccagactat gagcccatcc ggaaaggcca     840
gcgggacctg tattctggcc tgaatcagag acgcatctga ccctctggag aacactgcct     900
cccgctggcc caggtctcct ctccagtccc ctgcgactc cctgtttcct gggctagtct     960
tggaccccac gagagagaat cgttcctcag cctcatggtg aactcgcgcc ctccagcctg    1020 atccccgct ccctcctccc tgccttctct gctggtaccc agtcctaaaa tattgctgct    1080
tcctcttcct ttgaagcatc atcagtagtc acaccctcac agctggcctg ccctcttgcc    1140
aggatattta tttgtgctat tcactccctt cccctttggat gtaacttctc cgttcagttc    1200
cctccttttc ttgcatgtaa gttgtccccc atcccaaagt attccatcta cttttctatc    1260
gccgtcccct tttgcagccc tctctgggga tggactgggt aaatgttgac agaggccctg    1320 cccgttcac agatcctggc cctgagccag ccctgtgctc ctcccctccc caacactccc    1380
taccaacccc ctaatcccct actccctcca ccccccctcc actgtaggcc actggatggt    1440
catttgcatc tccgtaaatg tgctctgctc ctcagctgag agagaaaaaa ataaactgta    1500
tttggctgca agaaaaaaaa aaaaaaaaaa aaaa                                1534
```

<210> SEQ ID NO 3
<211> LENGTH: 2830
<212> TYPE: DNA
<213> ORGANISM: Homo sapiens

<400> SEQUENCE: 3

| | | | | | |
|---|---|---|---|---|---|
| ccacccagaa | aggctggagc | agggacgccg | tcgctccggc | cgcctgctcc | cctcgggtcc | 60 |
| ccgtgcgagc | ccacgccggc | cccggtgccc | gcccgcagcc | ctgccactgg | acacaggata | 120 |
| aggcccagcg | cacaggcccc | cacgtggaca | gcatggaccg | cggcacgctc | cctctggctg | 180 |
| ttgccctgct | gctggccagc | tgcagcctca | gccccacaag | tcttgcagaa | acagtccatt | 240 |
| gtgaccttca | gcctgtgggc | cccgagaggg | acgaggtgac | atataccact | agccaggtct | 300 |
| cgaagggctg | cgtggctcag | gcccccaatg | ccatccttga | agtccatgtc | ctcttcctgg | 360 |
| agttcccaac | gggcccgtca | cagctggagc | tgactctcca | ggcatccaag | caaaatggca | 420 |
| cctggccccg | agaggtgctt | ctggtcctca | gtgtaaacag | cagtgtcttc | ctgcatctcc | 480 |
| aggccctggg | aatcccactg | cacttggcct | acaattccag | cctggtcacc | ttccaagagc | 540 |
| ccccgggggt | caacaccaca | gagctgccat | ccttccccaa | gacccagatc | cttgagtggg | 600 |
| cagctgagag | gggcccatc | acctctgctg | ctgagctgaa | tgaccccag | agcatcctcc | 660 |
| tccgactggg | ccaagcccag | gggtcactgt | ccttctgcat | gctggaagcc | agccaggaca | 720 |
| tgggccgcac | gctcgagtgg | cggccgcgta | ctccagcctt | ggtccggggc | tgccacttgg | 780 |
| aaggcgtggc | cggccacaag | gaggcgcaca | tcctgagggt | cctgccgggc | cactcggccg | 840 |
| ggccccggac | ggtgacggtg | aaggtggaac | tgagctgcgc | acccggggat | ctcgatgccg | 900 |
| tcctcatcct | gcagggtccc | ccctacgtgt | cctggctcat | cgacgccaac | cacaacatgc | 960 |
| agatctggac | cactggagaa | tactccttca | agatctttcc | agagaaaaac | attcgtggct | 1020 |
| tcaagctccc | agacacacct | caaggcctcc | tgggggaggc | ccggatgctc | aatgccagca | 1080 |
| ttgtggcatc | cttcgtggag | ctaccgctgg | ccagcattgt | ctcacttcat | gcctccagct | 1140 |
| gcggtggtag | gctgcagacc | tcacccgcac | cgatccagac | cactcctccc | aaggacactt | 1200 |
| gtagcccgga | gctgctcatg | tccttgatcc | agacaaagtg | tgccgacgac | gccatgaccc | 1260 |
| tggtactaaa | gaaagagctt | gttgcgcatt | tgaagtgcac | catcacgggc | ctgaccttct | 1320 |
| gggacccag | ctgtgaggca | gaggacaggg | gtgacaagtt | tgtcttgcgc | agtgcttact | 1380 |
| ccagctgtgg | catgcaggtg | tcagcaagta | tgatcagcaa | tgaggcggtg | gtcaatatcc | 1440 |
| tgtcgagctc | atcaccacag | cggaaaaagg | tgcactgcct | caacatggac | agcctctctt | 1500 |
| tccagctggg | cctctacctc | agcccacact | tcctccaggc | ctccaacacc | atcgagccgg | 1560 |
| ggcagcagag | ctttgtgcag | gtcagagtgt | ccccatccgt | ctccgagttc | ctgctccagt | 1620 |
| tagacagctg | ccacctggac | ttggggcctg | agggaggcac | cgtggaactc | atccagggcc | 1680 |
| gggcggccaa | gggcaactgt | gtgagcctgc | tgtccccaag | cccgaggggt | gaccgcgct | 1740 |
| tcagcttcct | cctccacttc | tacacagtac | ccatacccaa | aaccggcacc | ctcagctgca | 1800 |
| cggtagccct | gcgtcccaag | accgggtctc | aagaccagga | agtccatagg | actgtcttca | 1860 |
| tgcgcttgaa | catcatcagc | cctgaccgtg | ctggttgcac | aagcaaaggc | ctcgtcctgc | 1920 |
| ccgccgtgct | gggcatcacc | tttggtgcct | tcctcatcgg | ggccctgctc | actgctgcac | 1980 |
| tctggtacat | ctactcgcac | acgcgttccc | ccagcaagcg | ggagcccgtg | gtggcggtgg | 2040 |
| ctgccccggc | ctcctcggag | agcagcagca | ccaaccacag | catcgggagc | acccagagca | 2100 |
| cccctgctc | caccagcagc | atggcatagc | cccggccccc | cgcgctcgcc | cagcaggaga | 2160 |

```
gactgagcag ccgccagctg ggagcactgg tgtgaactca ccctgggagc cagtcctcca    2220
ctcgacccag aatggagcct gctctccgcg cctacccttc ccgcctccct ctcagaggcc    2280
tgctgccagt gcagccactg gcttggaaca ccttggggtc cctccacccc acagaacctt    2340
caacccagtg ggtctgggat atggctgccc aggagacaga ccacttgcca cgctgttgta    2400
aaaacccaag tccctgtcat ttgaacctgg atccagcact ggtgaactga gctgggcagg    2460
aagggagaac ttgaaacaga ttcaggccag cccagccagg ccaacagcac ctcccgctg     2520 ggaagagaag agggcccagc ccagagccac ctggatctat ccctgcggcc tccacacctg    2580
aacttgccta actaactggc aggggagaca ggagcctagc ggagcccagc ctgggagccc    2640
agagggtggc aagaacagtg ggcgttggga gcctagctcc tgccacatgg agcccctct    2700 gccggtcggg cagccagcag aggggagta gccaagctgc ttgtcctggg cctgcccctg    2760
tgtattcacc accaataaat cagaccatga aaccaaaaaa aaaaaaaaaa aaaaaaaaa     2820 aaaaaaaaaa                                                           2830

<210> SEQ ID NO 4
<211> LENGTH: 3196
<212> TYPE: DNA
<213> ORGANISM: Homo sapiens

<400> SEQUENCE: 4
ctctacccgg ttggcaggcg gcctggccca gcccttctc taaggaagcg catttcctgc      60
ctccctgggc cggccgggct ggatgagccg ggagctccct gctgccggtc ataccacagc    120
cttcatctgc gccctggggc caggactgct gctgtcactg ccatccattg gagcccagca    180 cccctcccc gcccatcctt cggacagcaa ctccagccca gccccgcgtc cctgtgtcca    240
cttctcctga ccctcggcc gccacccag aaggctggag cagggacgcc gtcgctccgg     300
ccgcctgctc ccctcgggtc ccgtgcgag cccacgccgg ccccggtgcc cgcccgcagc    360
cctgccactg gacacaggat aaggcccagc gcacaggccc ccacgtggac agcatggacc    420
gcggcacgct ccctctggct gttgcccctgc tgctggccag ctgcagcctc agccccacaa    480
gtcttgcaga acagtccat tgtgaccttc agcctgtggg ccccgagagg ggcgaggtga    540
catataccac tagccaggtc tcgaagggct gcgtggctca ggcccccaat gccatccttg    600
aagtccatgt cctcttcctg gagttcccaa cgggccccgtc acagtggag ctgactctcc    660 aggcatccaa gcaaaatggc acctggccc gagaggtgct tctggtcctc agtgtaaaca    720
gcagtgtctt cctgcatctc caggccctgg gaatcccact gcacttggcc tacaattcca    780
gcctggtcac cttccaagag ccccggggg tcaacaccac agagctgcca tccttcccca    840
agacccagat cctgagtgg gcagctgaga ggggcccccat cacctctgct gctgagctga    900
atgaccccca gagcatcctc ctccgactgg gccaagccca gggtcactg tccttctgca    960 tgctggaagc cagccaggac atgggccgca cgctcgagtg gcggccgcgt actccagcct    1020
tggtccgggg ctgccacttg aaggcgtgg ccggccacaa ggaggcgcac atcctgaggg    1080
tcctgccggg ccactcggcc gggccccgga cggtgacggt gaaggtggaa ctgagctgcg    1140
cacccgggga tctcgatgcc gtcctcatcc tgcagggtcc cccctacgtg tcctggctca    1200
tcgacgccaa ccacaacatg cagatctgga ccactggaga atactccttc aagatctttc    1260
cagagaaaaa cattcgtggc ttcaagctcc cagacacacc tcaaggcctc ctgggggagg    1320
cccggatgct caatgccagc attgtggcat ccttcgtgga gctaccgctg ccagcattg    1380
```

| | |
|---|---|
| tctcacttca tgcctccagc tgcggtggta ggctgcagac ctcacccgca ccgatccaga | 1440 |
| ccactcctcc caaggacact tgtagcccgg agctgctcat gtccttgatc cagacaaagt | 1500 |
| gtgccgacga cgccatgacc ctggtactaa agaaagagct tgttgcgcat ttgaagtgca | 1560 |
| ccatcacggg cctgaccttc tgggacccca gctgtgaggc agaggacagg ggtgacaagt | 1620 |
| ttgtcttgcg cagtgcttac tccagctgtg gcatgcaggt gtcagcaagt atgatcagca | 1680 |
| atgaggcggt ggtcaatatc ctgtcgagct catcaccaca gcggaaaaag gtgcactgcc | 1740 |
| tcaacatgga cagcctctct ttccagctgg gcctctacct cagcccacac ttcctccagg | 1800 |
| cctccaacac catcgagccg ggcagcaga gctttgtgca ggtcagagtg tccccatccg | 1860 |
| tctccgagtt cctgctccag ttagacagct gccacctgga cttggggcct gagggaggca | 1920 |
| ccgtggaact catccagggc cgggcggcca agggcaactg tgtgagcctg ctgtccccaa | 1980 |
| gccccgaggg tgacccgcgc ttcagcttcc tcctccactt ctacacagta cccatacccA | 2040 |
| aaaccggcac cctcagctgc acggtagccc tgcgtcccaa gacccgggtct caagaccagg | 2100 |
| aagtccatag gactgtcttc atgcgcttga acatcatcag ccctgacctg tctggttgca | 2160 |
| caagcaaagg cctcgtcctg cccgccgtgc tgggcatcac cttttggtgcc ttcctcatcg | 2220 |
| gggccctgct cactgctgca ctctggtaca tctactcgca cacgcgtgag tacccccaggc | 2280 |
| ccccacagtg agcatgccgg gcccctccat ccacccgggg gagcccagtg aagcctctga | 2340 |
| gggattgagg ggccctggcc aggaccctga cctccgcccc tgccccgct cccgctccca | 2400 |
| ggttccccca gcaagcggga gcccgtggtg gcggtggctg ccccggcctc ctcggagagc | 2460 |
| agcagcacca accacagcat cgggagcacc cagagcaccc cctgctccac cagcagcatg | 2520 |
| gcatagcccc ggccccccgc gctcgcccag caggagagac tgagcagccg ccagctggga | 2580 |
| gcactggtgt gaactcaccc tgggagccag tcctccactc gacccagaat ggagcctgct | 2640 |
| ctccgcgcct acccttcccg cctccctctc agaggcctgc tgccagtgca gccactggct | 2700 |
| tggaacacct tggggtccct ccaccccaca gaaccttcaa cccagtgggt ctgggatatg | 2760 |
| gctgcccagg agacagacca cttgccacgc tgttgtaaaa acccaagtcc ctgtcatttg | 2820 |
| aacctggatc cagcactggt gaactgagct gggcaggaag ggagaacttg aaacagattc | 2880 |
| aggccagccc agccaggcca acagcacctc cccgctggga agagaagagg cccagccca | 2940 |
| gagccacctg gatctatccc tgcggcctcc acacctgaac ttgcctaact aactggcagg | 3000 |
| ggagacagga gcctagcgga gcccagcctg ggagcccaga gggtggcaag aacagtgggc | 3060 |
| gttgggagcc tagctcctgc cacatggagc cccctctgcc ggtcgggcag ccagcagagg | 3120 |
| gggagtagcc aagctgcttg tcctgggcct gcccctgtgt attcaccacc aataaatcag | 3180 |
| accatgaaac cagtga | 3196 |

<210> SEQ ID NO 5
<211> LENGTH: 3814
<212> TYPE: DNA
<213> ORGANISM: Homo sapiens

<400> SEQUENCE: 5

| | |
|---|---|
| cctctcaccc tttagcccag aactgctttg aatacaccaa ttgctgtggg gcggctcgag | 60 |
| gaagagaaga caccagtgcc tcagaaactg ctcggtcaga cggtgatagc gagccacgca | 120 |
| ttcacagggc cactgctgct cacagaagca gtgaggatga tgccaggatg atgtctgcct | 180 |
| cgcgcctggc tgggactctg atcccagcca tggccttcct ctcctgcgtg agaccagaaa | 240 |
| gctgggagcc ctgcgtggag gtggttccta atattactta tcaatgcatg gagctgaatt | 300 |

```
tctacaaaat ccccgacaac ctccccttct caaccaagaa cctggacctg agctttaatc      360
ccctgaggca tttaggcagc tatagcttct tcagtttccc agaactgcag gtgctggatt      420
tatccaggtg tgaaatccag acaattgaag atggggcata tcagagccta agccacctct      480
ctaccttaat attgacagga aaccccatcc agagtttagc cctgggagcc ttttctggac      540
tatcaagttt acagaagctg gtggctgtgg agacaaatct agcatctcta gagaacttcc      600
ccattggaca tctcaaaact ttgaaagaac ttaatgtggc tcacaatctt atccaatctt      660
tcaaattacc tgagtatttt tctaatctga ccaatctaga gcacttggac ctttccagca      720
acaagattca aagtatttat tgcacagact tgcgggttct acatcaaatg cccctactca      780
atctctcttt agacctgtcc ctgaacccta tgaactttat ccaaccaggt gcatttaaag      840
aaattaggct tcataagctg actttaagaa ataattttga tagtttaaat gtaatgaaaa      900
cttgtattca aggtctggct ggtttagaag tccatcgttt ggttctggga gaatttagaa      960
atgaaggaaa cttggaaaag tttgacaaat ctgctctaga gggcctgtgc aatttgacca     1020
ttgaagaatt ccgattagca tacttagact actacctcga tgatattatt gacttattta     1080
attgtttgac aaatgtttct tcattttccc tggtgagtgt gactattgaa agggtaaaag     1140 actttctctta taatttcgga tggcaacatt tagaattagt taactgtaaa tttggacagt     1200
ttcccacatt gaaactcaaa tctctcaaaa ggcttacttt cacttccaac aaaggtggga     1260 atgcttttc agaagttgat ctaccaagcc ttgagtttct agatctcagt agaaatggct      1320
tgagtttcaa aggttgctgt tctcaaagtg attttgggac aaccagccta agtatttag      1380 atctgagctt caatggtgtt attaccatga gttcaaactt cttgggctta gaacaactag     1440
aacatctgga tttccagcat tccaatttga aacaaatgag tgagttttca gtattcctat     1500
cactcagaaa cctcatttac cttgacattt ctcatactca caccagagtt gctttcaatg     1560
gcatcttcaa tggcttgtcc agtctcgaag tcttgaaaat ggctggcaat tctttccagg     1620
aaaacttcct tccagatatc ttcacagagc tgagaaactt gaccttcctg gacctctctc     1680
agtgtcaact ggagcagttg tctccaacag catttaactc actctccagt cttcaggtac     1740
taaatatgag ccacaacaac ttcttttcat tggatacgtt tccttataag tgtctgaact     1800
ccctccaggt tcttgattac agtctcaatc acataatgac ttccaaaaaa caggaactac     1860
agcattttcc aagtagtcta gctttcttaa atcttactca gaatgacttt gcttgtactt     1920
gtgaacacca gagtttcctg caatggatca aggaccagag gcagctcttg gtggaagttg     1980
aacgaatgga atgtgcaaca ccttcagata gcagggcat gcctgtgctg agtttgaata      2040
tcacctgtca gatgaataag accatcattg gtgtgtcggt cctcagtgtg cttgtagtat     2100
ctgttgtagc agttctggtc tataagttct attttcacct gatgcttctt gctggctgca     2160
taaagtatgg tagaggtgaa aacatctatg atgcctttgt tatctactca agccaggatg     2220
aggactgggg aaggaatgag ctagtaaaga atttagaaga aggggtgcct ccatttcagc     2280
tctgccttca ctacagagac tttattcccg gtgtggccat tgctgccaac atcatccatg     2340
aaggtttcca taaagccga aaggtgattg ttgtggtgtc ccagcacttc atccagagcc      2400
gctggtgtat ctttgaatat gagattgctc agacctggca gtttctgagc agtcgtgctg     2460
gtatcatctt cattgtcctg cagaaggtgg agaagaccct gctcaggcag caggtggagc     2520
tgtaccgcct tctcagcagg aacacttacc tggagtggga ggacagtgtc ctggggcggc     2580
acatcttctg gagacgactc agaaaagccc tgctggatgg taaatcatgg aatccagaag     2640
```

| | |
|---|---|
| gaacagtggg tacaggatgc aattggcagg aagcaacatc tatctgaaga ggaaaaataa | 2700 |
| aaacctcctg aggcatttct tgcccagctg gtccaacac ttgttcagtt aataagtatt | 2760 |
| aaatgctgcc acatgtcagg ccttatgcta agggtgagta attccatggt gcactagata | 2820 |
| tgcagggctg ctaatctcaa ggagcttcca gtgcagaggg aataaatgct agactaaaat | 2880 |
| acagagtctt ccaggtgggc atttcaacca actcagtcaa ggaacccatg acaaagaaag | 2940 |
| tcatttcaac tcttacctca tcaagttgaa taaagacaga gaaaacagaa agagacattg | 3000 |
| ttctttcct gagtcttttg aatggaaatt gtattatgtt atagccatca taaaaccatt | 3060 |
| ttggtagttt tgactgaact gggtgttcac tttttccttt ttgattgaat acaatttaaa | 3120 |
| ttctacttga tgactgcagt cgtcaagggg ctcctgatgc aagatgcccc ttccatttta | 3180 |
| agtctgtctc cttacagagg ttaaagtcta gtggctaatt cctaaggaaa cctgattaac | 3240 |
| acatgctcac aaccatcctg gtcattctcg agcatgttct atttttaac taatcacccc | 3300 |
| tgatatattt ttattttat atatccagtt tcatttttt tacgtcttgc ctataagcta | 3360 |
| atatcataaa taaggttgtt taagacgtgc ttcaaatatc catattaacc actatttttc | 3420 |
| aaggaagtat ggaaaagtac actctgtcac tttgtcactc gatgtcattc caaagttatt | 3480 |
| gcctactaag taatgactgt catgaaagca gcattgaaat aatttgttta aaggggggcac | 3540 |
| tcttttaaac gggaagaaaa tttccgcttc ctggtcttat catggacaat ttgggctaga | 3600 |
| ggcaggaagg aagtgggatg acctcaggag gtcacctttt cttgattcca gaaacatatg | 3660 |
| ggctgataaa cccggggtga cctcatgaaa tgagttgcag cagaagttta ttttttttcag | 3720 |
| aacaagtgat gtttgatgga cctctgaatc tctttaggga gacacagatg gctgggatcc | 3780 |
| ctcccctgta cccttctcac tgccaggaga acta | 3814 |

<210> SEQ ID NO 6
<211> LENGTH: 1648
<212> TYPE: DNA
<213> ORGANISM: Homo sapiens

<400> SEQUENCE: 6

| | |
|---|---|
| cagagaaggc ttaggctccc gagtcaacag ggcattcacc gcctggggcg cctgagtcat | 60 |
| caggacactg ccaggagaca cagaacccta gatgccctgc agaatccttc ctgttacggt | 120 |
| ccccctccct gaaacatcct tcattgcaat atttccagga aaggaagggg gctggctcgg | 180 |
| aggaagagag gtggggaggt gatcagggtt cacagaggag ggaactgaat gacatcccag | 240 |
| gattacataa actgtcagag gcagccgaag agttcacaag tgtgaagcct ggaagccggc | 300 |
| gggtgccgct gtgtaggaaa gaagctaaag cacttccaga gcctgtccgg agctcagagg | 360 |
| ttcggaagac ttatcgacca tggagcgcgc gtcctgcttg ttgctgctgc tgctgccgct | 420 |
| ggtgcacgtc tctgcgacca cgccagaacc ttgtgagctg gacgatgaag atttccgctg | 480 |
| cgtctgcaac ttctccgaac tcagcccga ctggtccgaa gccttccagt gtgtgtctgc | 540 |
| agtagaggtg gagatccatg ccggcggtct caacctagag ccgtttctaa agcgcgtcga | 600 |
| tgcggacgcc gacccgcggc agtatgctga cacggtcaag gctctccgcg tgcggcggct | 660 |
| cacagtggga gccgcacagg ttcctgctca gctactggta ggcgccctgc gtgtgctagc | 720 |
| gtactcccgc ctcaaggaac tgacgctcga ggacctaaag ataaccggca ccatgcctcc | 780 |
| gctgcctctg gaagccacag gacttgcact ttcagcttg cgcctacgca acgtgtcgtg | 840 |
| ggcgacaggg cgttcttggc tcgccgagct gcagcagtgg ctcaagccag gcctcaaggt | 900 |
| actgagcatt gcccaagcac actcgcctgc ctttttcctgc gaacaggttc gcgccttccc | 960 |

```
ggcccttacc agcctagacc tgtctgacaa tcctggactg ggcgaacgcg gactgatggc      1020
ggctctctgt ccccacaagt tcccggccat ccagaatcta gcgctgcgca acacaggaat      1080
ggagacgccc acaggcgtgt gcgccgcact ggcggcggca ggtgtgcagc cccacagcct      1140
agacctcagc cacaactcgc tgcgcgccac cgtaaaccct agcgctccga gatgcatgtg      1200
gtccagcgcc ctgaactccc tcaatctgtc gttcgctggg ctggaacagg tgcctaaagg      1260
actgccagcc aagctcagag tgctcgatct cagctgcaac agactgaaca gggcgccgca      1320
gcctgacgag ctgcccgagg tggataacct gacactggac gggaatccct tcctggtccc      1380
tggaactgcc ctcccccacg agggctcaat gaactccggc gtggtcccag cctgtgcacg      1440
ttcgaccctg tcggtggggg tgtcgggaac cctggtgctg ctccaagggg cccggggctt      1500
tgcctaagat ccaagacaga ataatgaatg gactcaaact gccttggctt caggggagtc      1560
ccgtcaggac gttgaggact tttcgaccaa ttcaacccct tgccccacct ttattaaaat      1620
cttaaacaac gggtcaaaaa aaaaaaaa                                        1648
```

<210> SEQ ID NO 7
<211> LENGTH: 3371
<212> TYPE: DNA
<213> ORGANISM: Homo sapiens

<400> SEQUENCE: 7

```
gctcgggcca cgcccacctg tcctgcagca ctggatgctt tgtgagttgg ggattgttgc        60
gtcccatatc tggacccaga agggacttcc ctgctcggct ggctctcggt ttctctgctt       120
tcctccggag aaataacagc gtcttccgcg ccgcgcatgg agcctcccgg ccgccgcgag       180 tgtcccttc cttcctggcg ctttcctggg ttgcttctgg cggccatggt gttgctgctg        240
tactccttct ccgatgcctg tgaggagcca ccaacatttg aagctatgga gctcattggt       300
aaaccaaaac cctactatga gattggtgaa cgagtagatt ataagtgtaa aaaggatac        360 ttctatatac ctcctcttgc cacccatact atttgtgatc ggaatcatac atggctacct       420
gtctcagatg acgcctgtta tagagaaaca tgtccatata tacgggatcc tttaaatggc       480
caagcagtcc ctgcaaatgg gacttacgag tttggttatc agatgcactt tatttgtaat       540
gagggttatt acttaattgg tgaagaaatt ctatattgtg aacttaaagg atcagtagca       600
atttggagcg gtaagccccc aatatgtgaa aaggttttgt gtacaccacc tccaaaaata       660
aaaaatggaa aacacacctt tagtgaagta gaagtatttg agtatcttga tgcagtaact       720
tatagttgtg atcctgcacc tggaccagat ccatttcac ttattggaga gagcacgatt        780
tattgtggtg acaattcagt gtggagtcgt gctgctccag agtgtaaagt ggtcaaatgt       840
cgatttccag tagtcgaaaa tggaaaacag atatcaggat tggaaaaaa attttactac        900 aaagcaacag ttatgtttga atgcgataag ggttttttacc tcgatggcag cgacacaatt       960
gtctgtgaca gtaacagtac ttgggatccc cagttccaa agtgtcttaa agtgctgcct       1020
ccatctagta caaaacctcc agctttgagt cattcagtgt cgacttcttc cactacaaaa       1080
tctccagcgt ccagtgcctc aggtcctagg cctacttaca agcctccagt ctcaaattat       1140
ccaggatatc ctaaacctga ggaaggaata cttgacagtt tggatgtttg ggtcattgct       1200
gtgattgtta ttgccatagt tgttggagtt gcagtaattt gtgttgtccc gtacagatat       1260
cttcaaagga ggaagaagaa aggcacatac ctaactgatg agaccacag agaagtaaaa       1320 tttacttctc tctgagaagg agagatgaga gaaaggtttg cttttatcat taaaaggaaa       1380
```

| | |
|---|---|
| gcagatggtg gagctgaata tgccacttac cagactaaat caaccactcc agcagagcag | 1440 |
| agaggctgaa tagattccac aacctggttt gccagttcat cttttgactc tattaaaatc | 1500 |
| ttcaatagtt gttattctgt agtttcactc tcatgagtgc aactgtggct tagctaatat | 1560 |
| tgcaatgtgg cttgaatgta ggtagcatcc tttgatgctt ctttgaaact tgtatgaatt | 1620 |
| tgggtatgaa cagattgcct gctttccctt aaataacact tagatttatt ggaccagtca | 1680 |
| gcacagcatg cctggttgta ttaaagcagg gatatgctgt atttataaa attggcaaaa | 1740 |
| ttagagaaat atagttcaca atgaaattat attttctttg taaagaaagt ggcttgaaat | 1800 |
| ctttttttgtt caaagattaa tgccaactct taagattatt ctttcaccaa ctatagaatg | 1860 |
| tattttatat atcgttcatt gtaaaaagcc cttaaaaata tgtgtatact actttggctc | 1920 |
| ttgtgcataa aaacaagaac actgaaaatt gggaatatgc acaaacttgg cttctttaac | 1980 |
| caagaatatt attggaaaat tctctaaaag ttaatagggt aaattctcta ttttttgtaa | 2040 |
| tgtgttcggt gatttcagaa agctagaaag tgtatgtgtg gcatttgttt tcactttta | 2100 |
| aaacatccct aactgatcga atatatcagt aatttcagaa tcagatgcat cctttcataa | 2160 |
| gaagtgagag gactctgaca gccataacag gagtgccact tcatggtgcg aagtgaacac | 2220 |
| tgtagtcttg ttgttttccc aaagagaact ccgtatgttc tcttaggttg agtaacccac | 2280 |
| tctgaattct ggttacatgt gttttttctct ccctccttaa ataaagagag gggttaaaca | 2340 |
| tgccctctaa aagtaggtgg ttttgaagag aataaaattca tcagataacc tcaagtcaca | 2400 |
| tgagaatctt agtccattta cattgccttg gctagtaaaa gccatctatg tatatgtctt | 2460 |
| acctcatctc ctaaaaggca gagtacaaag taagccatgt atctcaggaa ggtaacttca | 2520 |
| ttttgtctat ttgctgttga ttgtaccaag ggatggaaga agtaaatata gctcaggtag | 2580 |
| cactttatac tcaggcagat ctcagccctc tactgagtcc cttagccaag cagtttcttt | 2640 |
| caaagaagcc agcaggcgaa aagcagggac tgccactgca tttcatatca cactgttaaa | 2700 |
| agttgtgttt tgaaatttta tgtttagttg cacaaattgg gccaaagaaa cattgccttg | 2760 |
| aggaagatat gattggaaaa tcaagagtgt agaagaataa atactgtttt actgtccaaa | 2820 |
| gacatgttta tagtgctctg taaatgttcc tttccttttgt agtctctggc aagatgcttt | 2880 |
| aggaagataa aagtttgagg agaacaaaca ggaattctga attaagcaca gagttgaagt | 2940 |
| ttatacccgt ttcacatgct tttcaagaat gtcgcaatta ctaagaagca gataatggtg | 3000 |
| tttttttagaa acctaattga agtatattca accaaatact ttaatgtata aaataaatat | 3060 |
| tatacaatat acttgtatag cagtttctgc ttcacatttg attttttcaa atttaatatt | 3120 |
| tatattagag atctatatat gtataaatat gtattttgtc aaatttgtta cttaaatata | 3180 |
| tagagaccag ttttctctgg aagtttgttt aaatgacaga agcgtatatg aattcaagaa | 3240 |
| aatttaagct gcaaaaatgt atttgctata aaatgagaag tctcactgat agaggttctt | 3300 |
| tattgctcat ttttaaaaa atggactctt gaaatctgtt aaaataaaat tgtacatttg | 3360 |
| gagatgtttc a | 3371 |

<210> SEQ ID NO 8
<211> LENGTH: 2646
<212> TYPE: DNA
<213> ORGANISM: Homo sapiens

<400> SEQUENCE: 8

| | |
|---|---|
| gacttctgca gtttctgttt ccttgactgg cagctcagcg gggccctccc gcttggatgt | 60 |
| tccgggaaag tgatgtgggt aggacaggcg gggcgagccg caggtgccag aacacagatt | 120 |

```
gtataaaagg ctgggggctg gtggggagca ggggaaggga atgtgaccag gtctaggtct    180
ggagtttcag cttggacact gagccaagca gacaagcaaa gcaagccagg acacaccatc    240
ctgccccagg cccagcttct ctcctgcctt ccaacgccat ggggagcaat ctcagccccc    300
aactctgcct gatgcccttt atcttgggcc tcttgtctgg aggtgtgacc accactccat    360
ggtctttggc ccggcccag ggatcctgct ctctggaggg ggtagagatc aaaggcggct    420
ccttccgact tctccaagag ggccaggcac tggagtacgt gtgtccttct ggcttctacc    480
cgtaccctgt gcagacacgt acctgcagat ctacgggtc ctggagcacc ctgaagactc    540
aagaccaaaa gactgtcagg aaggcagagt gcagagcaat ccactgtcca agaccacacg    600
acttcgagaa cggggaatac tggccccggt ctccctacta caatgtgagt gatgagatct    660 cttttccactg ctatgacggt tacactctcc ggggctctgc caatcgcacc tgccaagtga    720
atggccgatg gagtgggcag acagcgatct gtgacaacgg agcggggtac tgctccaacc    780
cgggcatccc cattggcaca aggaaggtgg gcagccagta ccgccttgaa gacagcgtca    840
cctaccactg cagccggggg cttaccctgc gtggctccca gcggcgaacg tgtcaggaag    900
gtggctcttg gagcgggacg gagccttcct gccaagactc cttcatgtac gacacccctc    960
aagaggtggc cgaagctttc ctgtcttccc tgacagagac catagaagga gtcgatgctg   1020
aggatgggca cggcccaggg gaacaacaga agcggaagat cgtcctggac ccttcaggct   1080
ccatgaacat ctacctggtg ctagatggat cagacagcat tggggccagc aacttcacag   1140
gagccaaaaa gtgtcagtc aacttaattg agaaggtggc aagttatggt gtgaagccaa   1200
gatatggtct agtgacatat gccacatacc ccaaaatttg ggtcaaagtg tctgaagcag   1260
acagcagtaa tgcagactgg gtcacgaagc agctcaatga aatcaattat gaagaccaca   1320
agttgaagtc agggactaac accaagaagg ccctccaggc agtgtacagc atgatgagct   1380
ggccagatga cgtcccctcct gaaggctgga accgcacccg ccatgtcatc atcctcatga   1440
ctgatggatt gcacaacatg ggcggggacc caattactgt cattgatgag atccgggact   1500
tgctatacat tggcaaggat cgcaaaaacc caagggagga ttatctggat gtctatgtgt   1560 ttgggggtcgg gcctttggtg aaccaagtga acatcaatgc tttggcttcc aagaaagaca   1620
atgagcaaca tgtgttcaaa gtcaaggata tggaaaacct ggaagatgtt ttctaccaaa   1680
tgatcgatga aagccagtct ctgagtctct gtggcatggt tgggaacac aggaagggta   1740 ccgattacca caagcaacca tggcaggcca agatctcagt cattcgccct tcaaagggac   1800
acgagagctg tatgggggct gtggtgtctg agtactttgt gctgacagca gcacattgtt   1860
tcactgtgga tgacaaggaa cactcaatca aggtcagcgt aggagggag aagcgggacc   1920 tggagataga agtagtccta tttcaccccca actacaacat taatgggaaa aaagaagcag   1980
gaattcctga attttatgac tatgacgttg ccctgatcaa gctcaagaat aagctgaaat   2040
atggccagac tatcaggccc atttgtctcc cctgcaccga gggaacaact cgagctttga   2100
ggcttcctcc aactaccact tgccagcaac aaaaggaaga gctgctccct gcacaggata   2160
tcaaagctct gtttgtgtct gaggaggaga aaaagctgac tcggaaggag gtctacatca   2220
agaatgggga taagaaaggc agctgtgaga gagatgctca atatgcccca ggctatgaca   2280
aagtcaagga catctcagag gtggtcaccc ctcggttcct ttgtactgga ggagtgagtc   2340
cctatgctga ccccaatact tgcagaggtg attctggcgg ccccttgata gttcacaaga   2400
gaagtcgttt cattcaagtt ggtgtaatca gctggggagt agtggatgtc tgcaaaaacc   2460
```

| | | |
|---|---|---|
| agaagcggca aaagcaggta cctgctcacg cccgagactt tcacatcaac ctctttcaag | 2520 | |
| tgctgccctg gctgaaggag aaactccaag atgaggattt gggttttcta taagggtttt | 2580 | |
| cctgctggac aggggcgtgg gattgaatta aaacagctgc gacaacaaaa aaaaaaaaaa | 2640 | |
| aaaaaa | 2646 | |

<210> SEQ ID NO 9
<211> LENGTH: 1847
<212> TYPE: DNA
<213> ORGANISM: Homo sapiens

<400> SEQUENCE: 9

| | |
|---|---|
| gtccccgcgc cagagacgca gccgcgctcc caccacccac acccaccgcg ccctcgttcg | 60 |
| cctcttctcc gggagccagt ccgcgccacc gccgccgccc aggccatcgc caccctccgc | 120 |
| agccatgtcc accaggtccg tgtcctcgtc ctcctaccgc aggatgttcg gcggccgggg | 180 |
| caccgcgagc cggccgagct ccagccggag ctacgtgact acgtccaccc gcacctacag | 240 |
| cctgggcagc gcgctgcgcc ccagcaccag ccgcagcctc tacgcctcgt ccccgggcgg | 300 |
| cgtgtatgcc acgcgctcct ctgccgtgcg cctgcggagc agcgtgcccg gggtgcggct | 360 |
| cctgcaggac tcggtggact ctcgctggcg cgacgccatc aacaccgagt tcaagaacac | 420 |
| ccgcaccaac gagaaggtgg agctgcagga gctgaatgac cgcttcgcca actacatcga | 480 |
| caaggtgcgc ttcctggagc agcagaataa gatcctgctg gccgagctcg agcagctcaa | 540 |
| gggccaaggc aagtcgcgcc tgggggacct ctacgaggag gagatgcggg agctgcgccg | 600 |
| gcaggtggac cagctaacca acgacaaagc ccgcgtcgag gtggagcgcg acaacctggc | 660 |
| cgaggacatc atgcgcctcc gggagaaatt gcaggaggag atgcttcaga gagaggaagc | 720 |
| cgaaaacacc ctgcaatctt tcagacagga tgttgacaat gcgtctctgg cacgtcttga | 780 |
| ccttgaacgc aaagtggaat cttttgcaag agagattgcc ttttgaaga aactccacga | 840 |
| agaggaaatc caggagctgc aggctcagat tcaggaacag catgtccaaa tcgatgtgga | 900 |
| tgtttccaag cctgacctca cggctgccct gcgtgacgta cgtcagcaat atgaaagtgt | 960 |
| ggctgccaag aacctgcagg aggcagaaga atggtacaaa tccaagtttg ctgacctctc | 1020 |
| tgaggctgcc aaccggaaca tgacgcccct gcgccaggca aagcaggagt ccactgagta | 1080 |
| ccggagacag gtgcagtccc tcacctgtga agtggatgcc cttaaaggaa ccaatgagtc | 1140 |
| cctggaacgc cagatgcgtg aaatggaaga gaactttgcc gttgaagctg ctaactacca | 1200 |
| agacactatt ggccgcctgc aggatgagat tcagaatatg aaggaggaaa tggctcgtca | 1260 |
| ccttcgtgaa taccaagacc tgctcaatgt taagatggcc cttgacattg agattgccac | 1320 |
| ctacaggaag ctgctggaag gcgaggagag caggatttct ctgcctcttc caaacttttc | 1380 |
| ctccctgaac ctgagggaaa ctaatctgga ttcactccct ctggttgata cccactcaaa | 1440 |
| aaggacactt ctgattaaga cggttgaaac tagagatgga caggttatca acgaaacttc | 1500 |
| tcagcatcac gatgaccttg aataaaaatt gcacacactc agtgcagcaa tatattacca | 1560 |
| gcaagaataa aaaagaaatc catatcttaa agaaacagct ttcaagtgcc tttctgcagt | 1620 |
| ttttcaggag cgcaagatag atttggaata ggaataagct ctagttctta acaaccgaca | 1680 |
| ctcctacaag atttagaaaa aagtttacaa cataatctag tttacagaaa atcttgtgc | 1740 |
| tagaatactt tttaaaaggt attttgaata ccattaaaac tgctttttt tttccagcaa | 1800 |
| gtatccaacc aacttggttc tgcttcaata aatctttgga aaaactc | 1847 |

```
<210> SEQ ID NO 10
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 10
aagaaatggg tggtattaca cagaca                                          26

<210> SEQ ID NO 11
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 11
tgccatagta tttcagatcc aggat                                           25

<210> SEQ ID NO 12
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 12
ccatctctgg aaccacagta atattgacat gcc                                  33

<210> SEQ ID NO 13
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 13
gcgaatctga cttacgccat tatt                                            24

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
caagagggcc tccagagtcc                                                 20

<210> SEQ ID NO 15
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 15
cccacgcaca actcaatggt actgtcg                                         27

<210> SEQ ID NO 16
<211> LENGTH: 23
<212> TYPE: DNA
<213> ORGANISM: Artificial Sequence
<220> FEATURE:
<223> OTHER INFORMATION: A synthetic oligonucleotide
```

<400> SEQUENCE: 16
ggaccagtac agcttcagca ctg                                          23

<210> SEQ ID NO 17
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 17
gccctcttga agtcagggtg                                              20

<210> SEQ ID NO 18
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 18
tgccgcttct acagtttcca tgtggtacac                                   30

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
gagaagctga gtgccatgca                                              20

<210> SEQ ID NO 20
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 20
ggagcccttg tcggatgat                                               19

<210> SEQ ID NO 21
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 21
tgccattttc ccagccaggt gg                                           22

<210> SEQ ID NO 22
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 22
acgacgtggt cagctccaa                                               19

<210> SEQ ID NO 23
<211> LENGTH: 20

```
<212> TYPE: DNA
<213> ORGANISM: Artificial Sequence
<220> FEATURE:
<223> OTHER INFORMATION: A synthetic oligonucleotide

<400> SEQUENCE: 23
tccgctcact cccacttctg                                              20

<210> SEQ ID NO 24
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 24
aagccctgca cgtgg                                                   15

<210> SEQ ID NO 25
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 25
cagcctcagc cccacaagt                                               19

<210> SEQ ID NO 26
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 26
ggcccacagg ctgaaggt                                                18

<210> SEQ ID NO 27
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 27
ttgcagaaac agtccatt                                                18

<210> SEQ ID NO 28
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 28
cctggacttg gacaccatga t                                            21

<210> SEQ ID NO 29
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 29
```

```
actcggacgt cagacacata gttc                                           24

<210> SEQ ID NO 30
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 30
tgctgagtga accacagg                                                  18

<210> SEQ ID NO 31
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 31
cctcaaaggc ggtggtcat                                                 19

<210> SEQ ID NO 32
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 32
agcgatctcc aattccaata gg                                             22

<210> SEQ ID NO 33
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 33
ccaacagagt gacagtgt                                                  18

<210> SEQ ID NO 34
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 34
tggagagaaa catccgaatt attg                                           24

<210> SEQ ID NO 35
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 35
tggtgaggtg ggatcagaga ta                                             22

<210> SEQ ID NO 36
<211> LENGTH: 18
<212> TYPE: DNA
<213> ORGANISM: Artificial Sequence
```

```
<220> FEATURE:
<223> OTHER INFORMATION: A synthetic oligonucleotide

<400> SEQUENCE: 36
tcctctgaac aacaggga                                                    18

<210> SEQ ID NO 37
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 37
agagctgcga gaagatccac tt                                               22

<210> SEQ ID NO 38
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 38
ctccagcccc acagcagta                                                   19

<210> SEQ ID NO 39
<211> LENGTH: 14
<212> TYPE: DNA
<213> ORGANISM: Artificial Sequence
<220> FEATURE:
<223> OTHER INFORMATION: A synthetic oligonucleotide

<400> SEQUENCE: 39
atcgccccca aaat                                                        14

<210> SEQ ID NO 40
<211> LENGTH: 16
<212> TYPE: DNA
<213> ORGANISM: Artificial Sequence
<220> FEATURE:
<223> OTHER INFORMATION: A synthetic oligonucleotide

<400> SEQUENCE: 40
gggcgctgtg catcca                                                      16

<210> SEQ ID NO 41
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 41
aaggcctgat tttgtcctgg ta                                               22

<210> SEQ ID NO 42
<211> LENGTH: 15
<212> TYPE: DNA
<213> ORGANISM: Artificial Sequence
<220> FEATURE:
<223> OTHER INFORMATION: A synthetic olilgonucleotide

<400> SEQUENCE: 42
cgctgcaagg tgttt                                                       15
```

```
<210> SEQ ID NO 43
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 43
catggccttc ctctcctgc                                                  19

<210> SEQ ID NO 44
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 44
gaaattcagc tccatgcatt ga                                              22

<210> SEQ ID NO 45
<211> LENGTH: 23
<212> TYPE: DNA
<213> ORGANISM: Artificial Sequence
<220> FEATURE:
<223> OTHER INFORMATION: A synthetic olilgonucleotide

<400> SEQUENCE: 45
aggaaccacc tccacgcagg gct                                             23

<210> SEQ ID NO 46
<211> LENGTH: 27
<212> TYPE: DNA
<213> ORGANISM: Artificial Sequence
<220> FEATURE:
<223> OTHER INFORMATION: A synthetic olilgonucleotide

<400> SEQUENCE: 46
gctgtgtaga aagaagctaa agcactt                                         27

<210> SEQ ID NO 47
<211> LENGTH: 17
<212> TYPE: DNA
<213> ORGANISM: Artificial Sequence
<220> FEATURE:
<223> OTHER INFORMATION: A synthetic olilgonucleotide

<400> SEQUENCE: 47
tggcgtggtc gcagaga                                                    17

<210> SEQ ID NO 48
<211> LENGTH: 23
<212> TYPE: DNA
<213> ORGANISM: Artificial Sequence
<220> FEATURE:
<223> OTHER INFORMATION: A synthetic olilgonucleotide

<400> SEQUENCE: 48
cttatcgacc atggagcgcg cgt                                             23

<210> SEQ ID NO 49
<211> LENGTH: 22
<212> TYPE: DNA
<213> ORGANISM: Artificial Sequence
<220> FEATURE:
<223> OTHER INFORMATION: A synthetic olilgonucleotide
```

```
<400> SEQUENCE: 49
cagcaccgga aacagaaaag ag                                               22

<210> SEQ ID NO 50
<211> LENGTH: 21
<212> TYPE: DNA
<213> ORGANISM: Artificial Sequence
<220> FEATURE:
<223> OTHER INFORMATION: A synthetic olilgonucleotide

<400> SEQUENCE: 50
ccccggtacc tggtacagat c                                                21

<210> SEQ ID NO 51
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 51
aagaacacta tgatccttg                                                   19

<210> SEQ ID NO 52
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 52
ttccttggga ggccagtaga                                                  20

<210> SEQ ID NO 53
<211> LENGTH: 18
<212> TYPE: DNA
<213> ORGANISM: Artificial Sequence
<220> FEATURE:
<223> OTHER INFORMATION: A synthetic olilgonucleotide

<400> SEQUENCE: 53
agccaagcca ctgccaaa                                                    18

<210> SEQ ID NO 54
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 54
acctcattgt cagtacagg                                                   19

<210> SEQ ID NO 55
<211> LENGTH: 17
<212> TYPE: DNA
<213> ORGANISM: Artificial Sequence
<220> FEATURE:
<223> OTHER INFORMATION: A synthetic olilgonucleotide

<400> SEQUENCE: 55
gatgtgccgg gcaacag                                                     17

<210> SEQ ID NO 56
```

```
<211> LENGTH: 24
<212> TYPE: DNA
<213> ORGANISM: Artificial Sequence
<220> FEATURE:
<223> OTHER INFORMATION: A synthetic olilgonucleotide

<400> SEQUENCE: 56
cactctgacc atgatccttt caag                                          24

<210> SEQ ID NO 57
<211> LENGTH: 17
<212> TYPE: DNA
<213> ORGANISM: Artificial Sequence
<220> FEATURE:
<223> OTHER INFORMATION: A synthetic olilgonucleotide

<400> SEQUENCE: 57
tatccggcac tgctaca                                                  17

<210> SEQ ID NO 58
<211> LENGTH: 18
<212> TYPE: DNA
<213> ORGANISM: Artificial Sequence
<220> FEATURE:
<223> OTHER INFORMATION: A synthetic olilgonucleotide

<400> SEQUENCE: 58
tggcggcccc ttgatagt                                                 18

<210> SEQ ID NO 59
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 59
cccagctgat tacaccaact tg                                            22

<210> SEQ ID NO 60
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 60
cacaagagaa gtcgtttca                                                19

<210> SEQ ID NO 61
<211> LENGTH: 21
<212> TYPE: DNA
<213> ORGANISM: Artificial Sequence
<220> FEATURE:
<223> OTHER INFORMATION: A synthetic olilgonucleotide

<400> SEQUENCE: 61
caccacctga atgcagagga a                                             21

<210> SEQ ID NO 62
<211> LENGTH: 28
<212> TYPE: DNA
<213> ORGANISM: Artificial Sequence
<220> FEATURE:
<223> OTHER INFORMATION: A synthetic olilgonucleotide

<400> SEQUENCE: 62
```

```
gaacatttac tgtggtaggt ttctgaac                                           28
```

<210> SEQ ID NO 63
<211> LENGTH: 17
<212> TYPE: DNA
<213> ORGANISM: Artificial Sequence
<220> FEATURE:
<223> OTHER INFORMATION: A synthetic olilgonucleotide

<400> SEQUENCE: 63

```
ctaacttcca aggtccc                                                       17
```

<210> SEQ ID NO 64
<211> LENGTH: 24
<212> TYPE: DNA
<213> ORGANISM: Artificial Sequence
<220> FEATURE:
<223> OTHER INFORMATION: A synthetic olilgonucleotide

<400> SEQUENCE: 64

```
gatcggaatc atacatggct acct                                               24
```

<210> SEQ ID NO 65
<211> LENGTH: 23
<212> TYPE: DNA
<213> ORGANISM: Artificial Sequence
<220> FEATURE:
<223> OTHER INFORMATION: A synthetic olilgonucleotide

<400> SEQUENCE: 65

```
ggccatttaa aggatcccgt ata                                                23
```

<210> SEQ ID NO 66
<211> LENGTH: 34
<212> TYPE: DNA
<213> ORGANISM: Artificial Sequence
<220> FEATURE:
<223> OTHER INFORMATION: A synthetic olilgonucleotide

<400> SEQUENCE: 66

```
ctcagatgac gcctgttata gagaaacatg tcca                                    34
```

<210> SEQ ID NO 67
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 67

```
tcagagagag gaagccgaaa ac                                                 22
```

<210> SEQ ID NO 68
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 68

```
ccagagacgc attgtcaaca tc                                                 22
```

<210> SEQ ID NO 69
<211> LENGTH: 18
<212> TYPE: DNA

<213> ORGANISM: Artificial Sequence
<220> FEATURE:
<223> OTHER INFORMATION: A synthetic olilgonucleotide

<400> SEQUENCE: 69
ccctgcaatc tttcagac                                             18

<210> SEQ ID NO 70
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 70
tcacgagcaa ctcgcaaaga                                           20

<210> SEQ ID NO 71
<211> LENGTH: 21
<212> TYPE: DNA
<213> ORGANISM: Artificial Sequence
<220> FEATURE:
<223> OTHER INFORMATION: A synthetic olilgonucleotide

<400> SEQUENCE: 71
tcccatcacc gttagcaact c                                         21

<210> SEQ ID NO 72
<211> LENGTH: 24
<212> TYPE: DNA
<213> ORGANISM: Artificial Sequence
<220> FEATURE:
<223> OTHER INFORMATION: A synthetic olilgonucleotide

<400> SEQUENCE: 72
tgtggcagtc accccaagtt cagc                                      24

<210> SEQ ID NO 73
<211> LENGTH: 21
<212> TYPE: DNA
<213> ORGANISM: Artificial Sequence
<220> FEATURE:
<223> OTHER INFORMATION: A synthetic olilgonucleotide

<400> SEQUENCE: 73
tgagtgtccc ccggtatctt c                                         21

<210> SEQ ID NO 74
<211> LENGTH: 21
<212> TYPE: DNA
<213> ORGANISM: Artificial Sequence
<220> FEATURE:
<223> OTHER INFORMATION: A synthetic olilgonucleotide

<400> SEQUENCE: 74
cagccgcttt cagattttca t                                         21

<210> SEQ ID NO 75
<211> LENGTH: 27
<212> TYPE: DNA
<213> ORGANISM: Artificial Sequence
<220> FEATURE:
<223> OTHER INFORMATION: A synthetic olilgonucleotide

<400> SEQUENCE: 75
cctgccaatc ccgatgaaat tggaaat                                   27

<210> SEQ ID NO 76
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 76
ccaggagccc agctatgaac                                           20

<210> SEQ ID NO 77
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 77
cccagggaga aggcaactg                                            19

<210> SEQ ID NO 78
<211> LENGTH: 23
<212> TYPE: DNA
<213> ORGANISM: Artificial Sequence
<220> FEATURE:
<223> OTHER INFORMATION: A synthetic olilgonucleotide

<400> SEQUENCE: 78
ccttctccac aagcgccttc ggt                                       23

<210> SEQ ID NO 79
<211> LENGTH: 25
<212> TYPE: DNA
<213> ORGANISM: Artificial Sequence
<220> FEATURE:
<223> OTHER INFORMATION: A synthetic olilgonucleotide

<400> SEQUENCE: 79
aactccccat ctacccaata ctgtt                                     25

<210> SEQ ID NO 80
<211> LENGTH: 23
<212> TYPE: DNA
<213> ORGANISM: Artificial Sequence
<220> FEATURE:
<223> OTHER INFORMATION: A synthetic olilgonucleotide

<400> SEQUENCE: 80
agaaggcaaa gatcagcatc act                                       23

<210> SEQ ID NO 81
<211> LENGTH: 31
<212> TYPE: DNA
<213> ORGANISM: Artificial Sequence
<220> FEATURE:
<223> OTHER INFORMATION: A synthetic olilgonucleotide

<400> SEQUENCE: 81
cagcatacaa tctctgttct tgggcatttt g                              31

<210> SEQ ID NO 82
<211> LENGTH: 18
<212> TYPE: DNA
<213> ORGANISM: Artificial Sequence
<220> FEATURE:

<223> OTHER INFORMATION: A synthetic olilgonucleotide

<400> SEQUENCE: 82
cccgtgggaa tggttgtc                                                  18

<210> SEQ ID NO 83
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 83
gggtccacac acacaattga ct                                             22

<210> SEQ ID NO 84
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 84
atcatagtct ggaagaagaa                                                20

<210> SEQ ID NO 85
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 85
gcgtgctaat ggtggaaacc                                                20

<210> SEQ ID NO 86
<211> LENGTH: 22
<212> TYPE: DNA
<213> ORGANISM: Artificial Sequence
<220> FEATURE:
<223> OTHER INFORMATION: A synthetic olilgonucleotide

<400> SEQUENCE: 86
cggagctctg atgtgttgaa ga                                             22

<210> SEQ ID NO 87
<211> LENGTH: 37
<212> TYPE: DNA
<213> ORGANISM: Artificial Sequence
<220> FEATURE:
<223> OTHER INFORMATION: A synthetic olilgonucleotide

<400> SEQUENCE: 87
acaacgaaat ctatgacaag ttcaagcaga gtacaca                             37

<210> SEQ ID NO 88
<211> LENGTH: 20
<212> TYPE: DNA
<213> ORGANISM: Artificial Sequence
<220> FEATURE:
<223> OTHER INFORMATION: A synthetic olilgonucleotide

<400> SEQUENCE: 88
gcccgaagcg tttactttga                                                20

```
<210> SEQ ID NO 89
<211> LENGTH: 24
<212> TYPE: DNA
<213> ORGANISM: Artificial Sequence
<220> FEATURE:
<223> OTHER INFORMATION: A synthetic olilgonucleotide

<400> SEQUENCE: 89
tccattattc ctagctgcgg tatc                                              24

<210> SEQ ID NO 90
<211> LENGTH: 19
<212> TYPE: DNA
<213> ORGANISM: Artificial Sequence
<220> FEATURE:
<223> OTHER INFORMATION: A synthetic olilgonucleotide

<400> SEQUENCE: 90
aaagcaggcc cgagccgcc                                                    19
```

URINE MRNA PROFILE AND ACUTE DYSFUNCTION OF KIDNEY ALLOGRAFT

This application claims benefit of priority to the filing date of U.S. Provisional Application Ser. No. 61/924,543, filed Jan. 7, 2014, the contents of which are specifically incorporated by reference herein in their entity.

GOVERNMENT FUNDING

This invention was made with Government support under 2R37-AI051652, K08-DK087824 and UL1TR000457 awarded by National Institutes of Health. The United States Government has certain rights in the invention.

BACKGROUND

The healthiness of a kidney transplant is conventionally assessed by measuring creatinine levels in the blood. An increase in creatinine is called allograft dysfunction. Two types of acute rejection are the more common cause of allograft dysfunction: acute cellular and acute antibody mediated. Accurate diagnosis is important for providing that will provide treatment that is optimally therapeutic.

When the creatinine levels increase, patients typically undergo an invasive needle biopsy of the transplanted kidney to confirm acute rejection. However an increase in creatinine is not a specific test for acute rejection and a sizable proportion of patients with allograft dysfunction do not have acute rejection on biopsy. Moreover, invasive needle biopsy is not only associated with complications but is costly as well. Noninvasive tests to identify acute rejection would help obviate the need for biopsies in sizable proportion of patients with allograft dysfunction.

SUMMARY

The invention relates to methods of detecting acute kidney rejection in a subject, and discriminating between types of rejection, by detecting urinary RNA expression levels in a test urinary sample from the subject. For example, the methods described herein can be used to distinguish various types of kidney conditions such as acute rejection, acute tubular injury, acute cellular rejection, and/or antibody-mediated rejection. The methods can also be used to identify whether a subject has a kidney condition that may need treatment. Probes, primers, and methods for detecting RNA expression levels in urinary test samples and for performing the methods are also described herein.

For example, a method of detecting, predicting, or monitoring acute kidney rejection and distinguishing it from other types of kidney problems is described herein that includes:

(a) measuring urinary RNA expression levels of the following genes: CD3ε, CD105, TLR4, CD14, complement factor B, and vimentin in a test urinary cell sample from a subject with a kidney transplant; and (b) identifying increased expression of CD3ε, CD105, TLR4, CD14, complement factor B, and vimentin to thereby detect, predict, or monitor acute kidney rejection in the subject.

A six-gene diagnostic signature can be used to distinguish acute cellular rejection from acute tubular injury:

$$(0.52*\ln CD3\epsilon)+(1.02*\ln CD105)+(0.81*\ln TLR4)+(-1.16*\ln CD14)+(0.28*\ln \text{Complement Factor B})+(-0.79*\ln \text{Vimentin});$$

wherein a patient with test urinary cell sample that has a six-gene diagnostic signature of greater than about −0.24 has a transplanted kidney that is undergoing acute rejection, or will develop acute rejection. The method can also include treatment of subject for acute rejection when the six-gene diagnostic signature is greater than about −0.24. When the six-gene diagnostic signature of a sample is less than about −0.24 the patient from whom the sample was obtained has a transplanted kidney that is undergoing acute tubular injury, or will develop acute tubular injury. The method can also include treatment of subject for acute tubular injury when the six-gene diagnostic signature is less than about −0.24.

In another example, the method can include measuring urinary RNA expression levels of the following RNAs: CD3ε, CD105, CD14, CD46, and 18S rRNA in a test urinary cell sample from a subject with a kidney transplant. A five-gene diagnostic signature can be used to distinguish acute cellular rejection (ACR) from antibody-mediated rejection (AMR):

$$(0.67*\ln CD3\epsilon)+(-1.18*\ln CD105)+(1.30*\ln CD14)+(-0.83*\ln CD46)+(0.45*\ln 18S)$$

wherein a patient with a test urinary cell sample that has a five-gene diagnostic signature of greater than about 9.1 has a transplanted kidney that is undergoing acute cellular rejection, or will develop acute cellular rejection, rather than antibody-mediated rejection. The method can also include treatment of subject for acute cellular rejection when the five-gene diagnostic signature is greater than about 9.1. When the five-gene diagnostic signature of a sample is less than about 9.1 the patient from whom the sample was obtained has a transplanted kidney that is undergoing antibody-mediated rejection, or will develop antibody-mediated rejection. The method can also include treatment of subject for antibody-mediated rejection when the five-gene diagnostic signature is less than about 9.1.

Another method of detecting lack of acute kidney rejection involves measuring urinary RNA expression levels of one or more of the following: CD3ε, CD105, TLR4, CD14, CD46, complement factor B, vimentin, and 18S rRNA expression levels in a test urinary cell sample from a subject with a kidney transplant, identifying no increased expression of one or more of the CD3ε, CD105, TLR4, CD14, CD46, complement factor B, vimentin, and 18S rRNA to thereby detect lack of acute kidney rejection in a subject.

A kit is also described herein that includes instructions for detecting acute rejection of a kidney transplant, and probes or primers for selective hybridization to at least five mRNAs selected from the group: CD3ε, CD105, TLR4, CD14, CD46, complement factor B, vimentin, and 18S rRNA.

DESCRIPTION OF THE FIGURES

FIG. 1A is a schematic showing a flowchart for discovery and validation of urinary cell diagnostic signatures. Urinary cells were obtained from 84 kidney transplant recipients with acute allograft dysfunction. Transcript levels were measured in RNA from the urinary cells by pre-amplification enhanced real-time quantitative polymerase chain reaction (PCR) assays using a customized amplicon for construction of a standard curve of quantified mRNA abundance as copies per microgram of total RNA obtained from urinary cells. Individual transcripts were used as variables to construct statistical models using discriminant analysis. In each model the linear combination of variables yielded a discriminant score that constituted the diagnostic signature. A two-step approach was used to develop the diagnostic signatures. In the first step, acute rejection (both types, N=52) was differentiated from acute tubular injury (ATI, N=32). In the second step, acute cellular rejection (ACR, N=26) was differentiated from acute antibody mediated rejection (AMR, N=26) with the use of same PCR assay results. Ten-fold cross validation was used to validate both the models. FIG. 1B graphically illustrates the RNA quantity and purity, as well as the 18S rRNA levels in urinary cells from male or female patients, as a function of time post-kidney transplantation. The scatter plot shows the relation between time from kidney transplantation to the collection of urine samples (X-axis) and the quantity of total RNA isolated in urinary cells (Y-axis top), the purity of RNA as assessed by the ratio of the optical density (OD) at 260 nm to the optical density at 280 nm (Y-axis bottom) and the levels of endogenous control 18S ribosomal RNA. Total RNA was reverse transcribed to cDNA. The 18S rRNA level in urinary cells was quantified using gene specific primers and probes by real-time PCR assay and expressed as natural log-transformed copies per one microgram of total RNA. Dark closed circles represent samples from women and lighter open circles represent samples from men. By Spearman rank order correlation, there was no statistically significant association (P>0.5) between time from transplant to urine collection and each of the variables represented on the Y-axis. The $OD_{260}/OD_{280}$ ratio of pure RNA is about 2.

FIG. 2A-2ZA shows box plots illustrating the quantity of the twenty-six mRNAs and the 18S rRNA measured in the urinary cells of kidney transplant recipients at the time of for-cause (diagnostic) kidney biopsies. The X-axis of each box plot shows the expression levels of the indicated RNA in three groups of biopsy types; acute T-cell mediated rejection (ACR, left, N=26), acute antibody mediated rejection (AMR, center, N=26) and acute tubular injury (ATI, right, N=32). FIG. 2A shows CD3 expression levels. FIG. 2B shows Granzyme B expression levels. FIG. 2C shows perforin expression levels. FIG. 2D shows FoxP3 expression levels. FIG. 2E shows OX40 expression levels. FIG. 2F shows CD105 expression levels. FIG. 2G shows CD146 expression levels. FIG. 2H shows Von Willebrand factor expression levels. FIG. 2I shows Immunoglobulin J expression levels. FIG. 2J shows PSMB10 expression levels. FIG. 2K shows TRIM1 expression levels. FIG. 2L shows TRL-4 expression levels. FIG. 2M shows CD14 expression levels. FIG. 2N shows C3 expression levels. FIG. 2O shows C5 expression levels. FIG. 2P shows properdin expression levels. FIG. 2Q shows complement factor B expression levels. FIG. 2R shows CD55 expression levels. FIG. 2S shows CD46 expression levels. FIG. 2T shows vimentin expression levels. FIG. 2U shows NKCC2 expression levels. FIG. 2V shows E-cadherin expression levels. FIG. 2W shows IL-6 expression levels. FIG. 2X shows CXCL13 expression levels. FIG. 2Y shows CD20 expression levels. FIG. 2ZA shows TGFβ1 expression levels. FIG. 2Zb shows 18S rRNA expression levels. The 26 mRNAs and 18S rRNA were quantified using gene specific primers and probes by real-time PCR assay and expressed as copies per microgram of total RNA. The horizontal line within each box represents the median, the bottom and top of each box represent the 25th and 75th percentile values, and the whiskers represent the 10th and 90th percentile values. P values are based on the Kruskal-Wallis test. Individual groups were compared by Dunn's test, and if significant (P<0.05) are represented by an asterisk.

FIG. 3A shows a box plot of predicted probability of acute rejection from the cross validation. The horizontal line within each box represents the median and the plus symbol the mean. The bottom and top of each box represent 1.5 times the interquartile range. The values beyond this are shown as dots. The discrimination slope is the difference between the means of the predicted probabilities of the two groups. FIG. 3B shows the ROC curve of the predicted probability for each patient from the cross validation to diagnose AR. The sensitivity (true positive fraction), specificity (false positive fraction), likelihood ratio of a positive test (LR+, sensitivity/1-specificity) and likelihood ratio of a negative test (LR−, 1-sensitivity/specificity) for various cut-points of predicted risks are shown beneath the X-axis. The AUC is the estimate of the expected value in an independent sample not used for deriving the diagnostic signature. The absolute levels of the 26 mRNAs and the 18S rRNA in the urinary cells from 84 kidney graft recipients were measured. Quadratic discriminant function analysis was used to derive linear combination of mRNAs to better differentiate the 52 AR (acute rejection) biopsies (ACR and AMR, N=52 patients) from 32 ATI biopsies (N=32 patients) than any single mRNA measure. A linear combination of six mRNAs (CD3ε, CD105, TLR-4, CD14, Complement Factor B, and Vimentin) emerged as the parsimonious model and yielded a discriminant score that constituted the diagnostic signature. Ten-fold cross validation was performed to internally validate the 6-gene diagnostic signature. The entire study cohort of 84 patients was randomly divided into ten equal groups. Within each of the ten groups, the proportion of samples (AR vs. ATI) was similar to the undivided cohort. At the first run, group 1 (10% of samples) was excluded and a signature was derived from the remaining 9 groups (90% of samples) including both variables selection and model fitting. Next, this newly derived signature was applied to samples of group 1 to predict their diagnostic outcome. In the second run, group 2 was excluded and a signature was derived from the remaining 9 groups (90% of samples) including both variables selection and model fitting. This newly derived signature was applied to samples of group 2 (10% of samples) to predict their diagnostic outcome. This iteration was done for all the 10 groups. Thus, all observations were used for both deriving and validating a model and each observation was used for validation exactly once. Accordingly, the predicted probability for an individual patient was derived from a model that did not include any data from that patient. The predicted probability for each patient from the cross validation was used to construct a ROC curve. This is the estimate of the expected value of the AUC in an independent sample not used for deriving the diagnostic signature.

FIG. 4A shows the net benefit [(true positive count/n)−(false positive count/n)*[pt/(1−pt)] in the Y axis, where true positive count=the number of patients with AR, false positive count=the number of patients with ATI, n=the total number of patients and pt=threshold probability. Here, pt/(1−pt) is the ratio of the harms of false positive to false negative results. Of the 84 patients studied, 52 (62%) had AR. This proportion of acute rejection (AR) is a reasonable approximation of the expected incidence of AR in consecutive for-cause (diagnostic) biopsies done to identify the cause of acute graft dysfunction. The uppermost line is the net benefit of the urinary cell diagnostic signature. This strategy is compared with the 'biopsy all patients' strategy (middle line), which is essentially the current approach. The lowest line, which represents no net benefit, is the 'biopsy none' strategy. The decision curve plot depicts that among patients who present with acute graft dysfunction, within a reasonable physician/patient threshold probability for doing a biopsy to diagnose AR, the use of urinary cell diagnostic signature is beneficial compared with the current 'biopsy all patients' strategy. FIG. 4B shows the threshold probability on the X-axis, for the corresponding value on the Y-axis where the Y-axis represents the net reduction in avoidable biopsies per 100 patients, when using the diagnostic signature.

FIG. 5A shows the box plot of predicted probability of ACR biopsies from the cross-validation. FIG. 5B shows the ROC curve of the 5-gene urinary cell diagnostic signature to diagnose ACR. The AUC is the estimate of the expected value in an independent sample not used for deriving the diagnostic signature.

FIG. 6A shows the 6-gene signature. FIG. 6B shows the 5-gene signature. The diagnostic signature score is represented on the Y-axis for both the 6-gene signature (FIG. 6A) and the 5-gene signature (FIG. 6B) and time from transplantation to biopsy/urine sample collection, in logarithmic scale, is represented on the X-axis. Induction immunosuppression therapy with lymphocyte depleting-Thymoglobulin® (including one patient with alemtuzumab) is shown as closed symbols while induction with lymphocyte non-depleting interleukin-2 receptor antibody or no induction therapy is shown as open symbols. Within each diagnostic category, analysis involving Spearman rank order correlation showed that there was no significant association ($P>0.5$) between the score of the 6 or the 5-gene diagnostic signature and the time from transplantation to biopsy in patients with biopsies showing ACR, AMR or ATI and induced with depleting or non-depleting antibodies. There was also no association between the scores of the signatures and either serum creatinine levels (6-gene signature-ACR: $r_s=-0.39$, $P=0.06$; AMR: $r_s=-0.19$, $P=0.3$; ATI: $r_s=-0.002$, $P=0.9$ and 5-gene signature-ACR: $r_s=-0.14$, $P=0.5$; AMR: $r_s=-0.07$, $P=0.7$) or tacrolimus trough levels (6-gene signature-ACR: $r_s=0.14$, $P=0.5$; AMR: $r_s=-0.14$, $P=0.5$; ATI: $r_s=-0.02$, $P=0.9$ and 5-gene signature-ACR: $r_s=-0.12$, $P=0.6$; AMR: $r_s=-0.02$, $P=0.9$) (not shown).

DETAILED DESCRIPTION

Figure 1A:
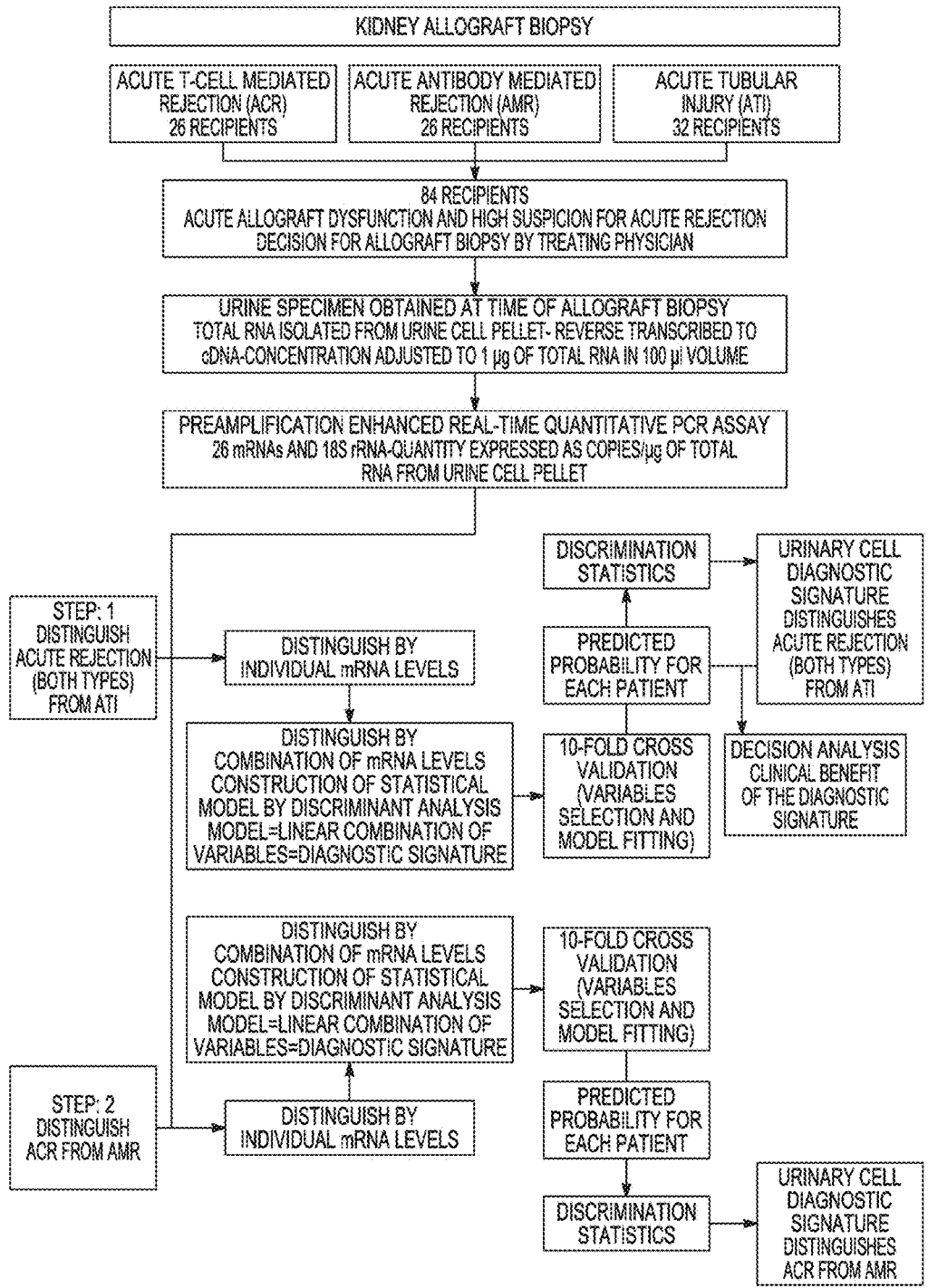
FIG. 1A-1B illustrates the methods and characteristics of the patient samples used to develop the methods.

Noninvasive tests to differentiate the basis for acute dysfunction of the kidney allograft are preferable to invasive allograft biopsies. As described herein, cells obtained from urine samples of patients with kidney transplants can be used to detect whether the patient has, or will develop transplant tissue rejection.

For example, the urinary cell expression levels of mRNAs for CD3ϵ, CD105, TLR4, CD14, complement factor B, and vimentin distinguish acute rejection (AR) from acute tubular injury (ATI) in a six-gene signature. The method for distinguishing acute rejection (AR) from acute tubular injury (ATI) involved natural log (ln) transformation of measured mRNA values of CD3ϵ, CD105, TLR4, CD14, Complement factor B, and Vimentin where the unit of measurement in the PCR assay is copies/μg of total RNA. The six-gene diagnostic signature that distinguished AR from ATI is as follows:

(0.52*ln CD3ϵ)+(1.02*ln CD105)+(0.81*ln TLR4)+
(−1.16*ln CD14)+(0.28*ln Complement Factor
B)+(−0.79*ln Vimentin).

This diagnostic signature better differentiated AR from ATI than any single mRNA measure (e.g. vs. CD3ϵ [AUC: 0.88], likelihood ratio test $X^2=40.6$, $P<0.0001$). The diagnostic signature also outperformed other variables; time from transplantation to biopsy (AUC: 0.65), serum creatinine (AUC: 0.59) or tacrolimus trough levels (AUC: 0.77).

A six-gene diagnostic signature of greater than about −0.24 indicates that the transplanted kidney in the patient from whom the tested sample was obtained can be acutely rejecting the transplanted kidney, or will develop acute rejection of the transplanted kidney. For example, a six-gene diagnostic signature that greater than about −0.2, or greater than about −0.1, or greater than about 0, or greater than about 0.1, or greater than about 0.2, or greater than about 0.3, or greater than about 0.4 indicates that the transplanted kidney in the patient from whom the tested sample was obtained can be acutely rejecting the transplanted kidney, or will develop acute rejection of the transplanted kidney.

In general, a six-gene diagnostic signature of less than about −0.25 indicates that the transplanted kidney in the patient from whom the tested sample was obtained is not acutely rejecting the transplanted kidney. However, when a sample has a six-gene diagnostic signature of less than about −0.25, the patient from whom the sample was obtained can have a kidney with acute tubular injury (ATI). For example, samples with a six-gene diagnostic signature of less than about −0.3, or less than about −0.35, or less than about −0.4, or less than about −0.45, or less than about −0.5, or less than about −0.6 can mean that the patient from whom the sample was obtained has a kidney with acute tubular injury (ATI).

In addition, mRNAs for CD3ϵ, CD105, CD14, CD46 and 18S rRNA can distinguish acute cellular rejection (ACR) from antibody-mediated rejection (AMR) in a five-gene signature. The five-gene model involved natural log (ln) transformation of measured mRNA values of CD3ϵ, CD105, CD14, CD46 and 18S rRNA and the following algorithm:

(0.67*ln CD3ϵ)+(−1.18*ln CD105)+(1.30*ln
CD14)+(−0.83*ln CD46)+(0.45*ln 18S).

Figure 4A:
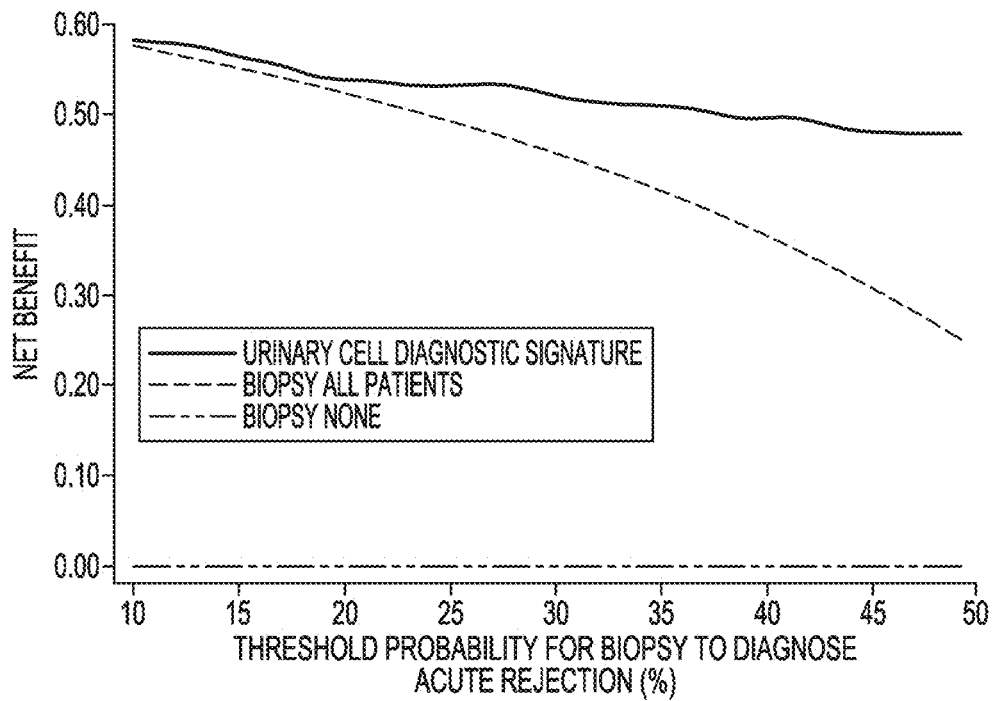
FIG. 4A-4B illustrate decision curve analysis to assess the clinical benefit of the 6-gene urinary cell diagnostic signature. The predicted probability for each patient from the cross validation in decision curve analysis was used to quantify the clinical benefit of the diagnostic signature in terms of the number of unnecessary biopsies that can be avoided in the diagnosis of AR.

This diagnostic signature better differentiated ACR from AMR than any other single mRNA measure (e.g. vs. CD3ϵ [AUC: 0.87], likelihood ratio test $X^2=30.4$, $P<0.0001$). Ten-fold cross validation of this 5-gene model yielded an AUC of 0.81 (95% CI 0.68 to 0.93, $P<0.001$, FIG. 4).

A five-gene diagnostic signature of greater than about 9.24 indicates that the transplanted kidney in the patient from whom the tested sample was obtained is undergoing acute cellular rejection, or will develop acute cellular rejection. For example, a five-gene diagnostic signature of greater than about 9.24, or greater than about 9.3, or greater than about 9.4, or greater than about 9.5, or greater than about 9.6, or greater than about 9.7, or greater than about 9.8, or greater than about 9.9 indicates that the transplanted kidney in the patient from whom the tested sample was obtained is undergoing acute cellular rejection, or will develop acute cellular rejection.

In general, a five-gene diagnostic signature of less than about 9.24 indicates that the transplanted kidney in the patient from whom the tested sample was obtained is undergoing antibody-mediated rejection rather than acute cellular rejection. For example, a five-gene diagnostic signature of less than about 9.2, or less than about 9.1, or less than about 9.0, or less than about 8.7, or less than about 8.5, or less than about 8.0, or less than about 7.0, or less than about 6.0, or less than about 5.0 indicates that the transplanted kidney in the patient from whom the tested sample was obtained is undergoing antibody-mediated rejection rather than acute cellular rejection.

The inventors measured absolute levels of a panel of 26 pre-specified mRNAs in 84 urine samples collected from 84 kidney graft recipients at the time of a for-cause biopsy for acute allograft dysfunction, and investigated whether differential diagnosis of acute graft dysfunction is feasible using urinary cell mRNA profiles. Fifty-two urine samples from 52 patients with acute rejection biopsies (26 with acute T-cell mediated rejection [ACR] and 26 with acute antibody-mediated rejection [AMR]) and 32 urine samples from 32 patients with acute tubular injury and without acute rejection changes (ATI) were profiled. A stepwise quadratic discriminant analysis of mRNA measurements identified a linear combination of mRNAs for CD3ε, CD105, TLR4, CD14, complement factor B, and vimentin that distinguishes acute rejection from acute tubular injury (ATI). Ten-fold cross validation of the 6-gene signature yielded an estimate of the area under the curve (AUC) of 0.92 (95% CI, 0.86-0.98). In a decision analysis, the 6-gene signature yielded the highest net benefit across a range of reasonable threshold probabilities for biopsy. Next, among patients diagnosed with acute rejection biopsies, a similar statistical approach identified a linear combination of mRNAs for CD3ε, CD105, CD14, CD46 and 18S rRNA that distinguishes ACR from AMR, with a cross-validated estimate of the AUC of 0.81 (95% CI, 0.68-0.93). The incorporation of these urinary cell mRNA signatures in clinical decision making may help avoid substantial number of biopsies in patients with acute dysfunction of the kidney allograft.

Organ Transplant

Organ transplantation or the transfer of an organ from one human to another continues to rise throughout the world as the treatment of choice when an organ is irreversibly damaged or organ function is severely impaired. Organ transplantation is not without complications, not only from the transplant surgery itself, but also from the transplant recipient's own immune system and this process, if it happens suddenly, is called acute rejection.

For example, when acute rejection of a kidney transplant occurs, it manifests itself by a sudden deterioration in kidney transplant function. About 30 percent of transplant recipients experience an episode of acute rejection. Acute rejection can be associated with reduction in the one-year survival rate of kidney grafts from a deceased donor of about 20 percent, and the projected half-life is about four years shorter in patients who have had an episode of acute rejection compared to patients who have not had an episode of acute rejection.

Sometimes, acute rejection can result from the activation of recipient's T cells and/or B cells. The rejection primarily due to T cells is classified as T cell mediated acute rejection or acute cellular rejection (ACR) and the rejection in which B cells are primarily responsible is classified as antibody mediated acute rejection (AMR). Often times, acute rejection of either type can result in the complete loss of transplant function and transplant failure.

An increase in the level of serum creatinine, a clinically used measure of kidney function, is often the first clinical indicator of acute rejection, and is currently the best surrogate marker of acute rejection of either type. However, this biomarker lacks sensitivity and specificity because graft dysfunction can occur due to non-immunological causes.

Two of the commonly used drugs prescribed to transplant recipients to prevent rejection, cyclosporine and tacrolimus, can cause kidney toxicity, and this complication is not readily identified solely on the basis of blood concentrations of cyclosporine/tacrolimus. In kidney transplant patients, the clinical importance of distinguishing acute rejection from cyclosporine/tacrolimus toxicity cannot be overemphasized because the treatment approaches are diametrically opposite. In one instance, continued administration of cyclosporine/tacrolimus for rejection is critical whereas, in the other instance, a reduction in dosage or discontinuation of cyclosporine/tacrolimus is indicated to prevent further kidney toxicity. Furthermore, deterioration in kidney function is not always available as a clinical clue to diagnose rejection because many of the kidney transplants suffer from acute (reversible) renal failure in the immediate post-transplantation period due to injury from organ procurement and the ex-vivo preservation procedures involved.

Currently, acute rejection is diagnosed by performing an invasive core needle biopsy procedure, which obtains a biopsy of the kidney graft. The histological features in the allograft biopsy tissues are then observed. However, this invasive biopsy procedure is associated with complications such as bleeding, arteriovenous fistula, graft loss, and, in severe cases, even death.

Development of a noninvasive test either to anticipate an episode of acute rejection or to diagnose acute rejection without performing the transplant biopsy procedure is a major and an unmet goal in organ transplantation.

Measurement of mRNA and 18S rRNA Quantities in Urinary Cells

Any procedure available to those of skill in the art can be employed to determine the expression levels of CD3ε mRNA, CD105 mRNA, TLR4 mRNA, CD14 mRNA, complement factor B mRNA, vimentin mRNA, CD46 mRNA, 18S rRNA, or a combination thereof. For example, probes, primers, and/or antibodies can be employed in quantitative nucleic acid amplification reactions (e.g., quantitative polymerase chain reaction (PCR)), primer extension, Northern blot, immunoassay, immunosorbant assay (ELISA), radioimmunoassay (RIA), immunofluorimetry, immunoprecipitation, equilibrium dialysis, immunodiffusion, immunoblotting, mass spectrometry and other techniques available to the skilled artisan.

In some embodiments, the expression levels CD3ε mRNA, CD105 mRNA, TLR4 mRNA, CD14 mRNA, complement factor B mRNA, vimentin mRNA, CD46 mRNA, 18S rRNA, or a combination thereof are determined using respective probes or primers that can hybridize to the CD3ε mRNA, CD105 mRNA, TLR4 mRNA, CD14 mRNA, complement factor B mRNA, vimentin mRNA, CD46 mRNA, and 18S rRNA.

Sequences for CD3ε mRNA, CD105 mRNA, TLR4 mRNA, CD14 mRNA, complement factor B mRNA, vimentin mRNA, CD46 mRNA, and 18S rRNA are readily available and can be used to make such probes and primers.

For example, the following cDNA sequence for a human 18S rRNA is available from the National Center for Biotechnology Information database (see website at ncbi.nlm.nih.gov) as accession number K03432 (SEQ ID NO:1).

```
   1 CGCTGCTCCT CCCGTCGCCG TCCGGGCCCG TCCGTCCGTC
  41 CGTCCGTCGT CCTCCTCGCT NNNNCGGGGC GCCGGGCCCG
  61 TCCTCACNGG CCCCCGNNNN NGTCCNGGCC CGTCGGGGCC
 121 TCGCCGCGCT CTACCTTACC TACCTGGTTG ATCCTGCCAG
 161 TAGCATATGC TTGTCTCAAA GATTAAGCCA TGCATGTCTA
 201 AGTACGCACG GCCGGTACAG TGAAACTGCG AATGGCTCAT
 241 TAAATCAGTT ATGGTTCCTT TGGTCGCTCG CTCCTCTCCT
 281 ACTTGGATAA CTGTGGTAAT TCTAGAGCTA ATACATGCCG
 321 ACGGGCGCTG ACCCCCTTCG CGGGGGGGAT GCGTGCATTT
 361 ATCAGATCAA AACCAACCCG GTCAGCCCCT CTCCGGCCCC
 401 GGCCGGGGGG CGGGCGCCGG CGGCTTTGGT GACTCTAGAT
 441 AACCTCGGGC CGATCGCACG CCCCCCGTGG CGGCGACGAC
 481 CCATTCGAAC GTCTGCCCTA TCAACTTTCG ATGGTAGTCG
 521 CCGTGCCTAC CATGGTGACC ACGGGTGACG GGGAATCAGG
 561 GTTCGATTCC GGAGAGGGAG CCTGAGAAAC GGCTACCACA
 601 TCCAAGGAAG GCAGCAGGCG CGCAAATTAC CCACTCCCGA
 641 CCCGGGGAGG TAGTGACGAA AAATAACAAT ACAGGACTCT
 681 TTCGAGGCCC TGTAATTGGA ATGAGTCCAC TTTAAATCCT
 721 TTAACGAGGA TCCATTGGAG GGCAAGTCTG GTGCCAGCAG
 761 CCGCGGTAAT TCCAGCTCCA ATAGCGTATA TTAAAGTTGC
 801 TGCAGTTAAA AAGCTCGTAG TTGGATCTTG GGAGCGGGCG
 841 GGCGGTCCGC CGCGAGGCGA GCCACCGCCC GTCCCCGCCC
 881 CTTGCCTCTC GGCGCCCCCT CGATGCTCTT AGCTGAGTGT
 921 CCCGCGGGGC CCGAAGCGTT TACTTTGAAA AAATTAGAGT
 961 GTTCAAAGCA GGCCCGAGCC GCCTGGATAC CGCAGCTAGG
1001 AATAATGGAA TAGGACCGCG GTTCTATTTT GTTGGTTTTC
1041 GGAACTGAGG CCATGATTAA GAGGGACGGC CGGGGGCATT
1081 CGTATTGCGC CGCTAGAGGT GAAATTCCTT GGACCGGCGC
1121 AAGACGGACC AGAGCGAAAG CATTTGCCAA GAATGTTTTC
1161 ATTAATCAAG AACGAAAGTC GGAGGTTCGA AGACGATCAG
1201 ATACCGTCGT AGTTCCGACC ATAAACGATG CCGACCGGCG
1241 ATGCGGCGGC GTTATTCCCA TGACCCGCCG GGCAGCTTCC
1281 GGGAAACCAA AGTCTTTGGG TTCCGGGGGG AGTATGGTTG
1321 CAAAGCTGAA ACTTAAAGGA ATTGACGGAA GGGCACCACC
1361 AGGAGTGGAG CCTGCGGCTT AATTTGACTC AACACGGGAA
1401 ACCTCACCCG GCCCGGACAC GGACAGGATT GACAGATTGA
1441 TAGCTCTTTC TCGATTCCGT GGGTGGTGGT GCATGGCCGT
1481 TCTTAGTTGG TGGAGCGATT TGTCTGGTTA ATTCCGATAA
1521 CGAACGAGAC TCTGGCATGC TAACTAGTTA CGCGACCCCC
1561 GAGCGGTCGG CGTCCCCCAA CTTCTTAGAG GGACAAGTGG
1601 CGTTCAGCCA CCCGAGATTG AGCAATAACA GGTCTGTGAT
1641 GCCCTTAGAT GTCCGGGGCT GCACGCGCGC TACACTGACT
1681 GGCTCAGCGT GTGCCTACCC TACGCCGGCA GGCGCGGGTA
1721 ACCCGTTGAA CCCCATTCGT GATGGGGATC GGGGATTGCA
1761 ATTATTCCCC ATGAACGAGG AATTCCCAGT AAGTGCGGGT
1801 CATAAGCTTG CGTTGATTAA GTCCCTGCCC TTTGTACACA
1841 CCGCCCGTCG CTACTACCGA TTGGATGGTT TAGTGAGGCC
1881 CTCGGATCGG CCCCGCCGGG GTCGGCCCAC GGCCCTGGCG
1921 GAGCGCTGAG AAGACGGTCG AACTTGACTA TCTAGAGGAA
1961 GTAAAAGTCG TAACAAGGTT TCCGTAGGTG AACCTGCGGA
2001 AGGATCATTA ACGGAGCCCG GACGGCGGCC CGCGGCGGCG
2041 CCGCGCCGCG CTTCCCTCCG CACACCCACC CCCCCACCGC
2081 GACGGCGCGT GCGGGCGGGG CCGTGCCCGT TCGTTCGCTC
2121 GCTCGTTCGT TCGCCGCCCG GCCCGGCCGC GAGAGCCGAG
2161 AACTCGGGAG GGAGACGGGG GAGAGAGAGA GAGAGAGAGA
2201 GAGAGAGAGA GAGAGAGAGA GAAAGAAGGG CGTGT
```

A cDNA sequence for a human CD3ε is also available from the National Center for Biotechnology Information database as accession number NM_000733 (SEQ ID NO:2).

```
   1 TATTGTCAGA GTCCTCTTGT TTGGCCTTCT AGGAAGGCTG
  41 TGGGACCCAG CTTTCTTCAA CCAGTCCAGG TGGAGGCCTC
  81 TGCCTTGAAC GTTTCCAAGT GAGGTAAAAC CCGCAGGCCC
 121 AGAGGCCTCT CTACTTCCTG TGTGGGGTTC AGAAACCCTC
 161 CTCCCCTCCC AGCCTCAGGT GCCTGCTTCA GAAAATGAAG
 201 TAGTAAGTCT GCTGGCCTCC GCCATCTTAG TAAAGTAACA
 241 GTCCCATGAA ACAAAGATGC AGTCGGGCAC TCACTGGAGA
 281 GTTCTGGGCC TCTGCCTCTT ATCAGTTGGC GTTTGGGGGC
 321 AAGATGGTAA TGAAGAAATG GGTGGTATTA CACAGACACC
 361 ATATAAAGTC TCCATCTCTG GAACCACAGT AATATTGACA
 401 TGCCCTCAGT ATCCTGGATC TGAAATACTA TGGCAACACA
 441 ATGATAAAAA CATAGGCGGT GATGAGGATG ATAAAAACAT
 481 AGGCAGTGAT GAGGATCACC TGTCACTGAA GGAATTTTCA
 521 GAATTGGAGC AAAGTGGTTA TTATGTCTGC TACCCCAGAG
 561 GAAGCAAACC AGAAGATGCG AACTTTTATC TCTACCTGAG
 601 GGCAAGAGTG TGTGAGAACT GCATGGAGAT GGATGTGATG
 641 TCGGTGGCCA CAATTGTCAT AGTGGACATC TGCATCACTG
 681 GGGGCTTGCT GCTGCTGGTT TACTACTGGA GCAAGAATAG
```

```
 721 AAAGGCCAAG GCCAAGCCTG TGACACGAGG AGCGGGTGCT
 761 GGCGGCAGGC AAAGGGGACA AAACAAGGAG AGGCCACCAC
 801 CTGTTCCCAA CCCAGACTAT GAGCCCATCC GGAAAGGCCA
 841 GCGGGACCTG TATTCTGGCC TGAATCAGAG ACGCATCTGA
 881 CCCTCTGGAG AACACTGCCT CCCGCTGGCC CAGGTCTCCT
 921 CTCCAGTCCC CCTGCGACTC CCTGTTTCCT GGGCTAGTCT
 961 TGGACCCCAC GAGAGAGAAT CGTTCCTCAG CCTCATGGTG
1001 AACTCGCGCC CTCCAGCCTG ATCCCCCGCT CCCTCCTCCC
1041 TGCCTTCTCT GCTGGTACCC AGTCCTAAAA TATTGCTGCT
1081 TCCTCTTCCT TTGAAGCATC ATCAGTAGTC ACACCCTCAC
1121 AGCTGGCCTG CCCTCTTGCC AGGATATTTA TTTGTGCTAT
1161 TCACTCCCTT CCCTTTGGAT GTAACTTCTC CGTTCAGTTC
1201 CCTCCTTTTC TTGCATGTAA GTTGTCCCCC ATCCCAAAGT
1241 ATTCCATCTA CTTTTCTATC GCCGTCCCCT TTTGCAGCCC
1281 TCTCTGGGGA TGGACTGGGT AAATGTTGAC AGAGGCCCTG
1321 CCCCGTTCAC AGATCCTGGC CCTGAGCCAG CCCTGTGCTC
1361 CTCCCTCCCC CAACACTCCC TACCAACCCC CTAATCCCCT
1401 ACTCCCTCCA CCCCCCCTCC ACTGTAGGCC ACTGGATGGT
1441 CATTTGCATC TCCGTAAATG TGCTCTGCTC CTCAGCTGAG
1481 AGAGAAAAAA ATAAACTGTA TTTGGCTGCA AGAAAAAAAA
1521 AAAAAAAAAA AAAA
```

A cDNA sequence for human CD105 (also called endoglin) is available from the National Center for Biotechnology Information database as accession number BC014271.2 (GI:33871100; SEQ ID NO:3).

```
   1 CCACCCCAGA AGGCTGGAGC AGGGACGCCG TCGCTCCGGC
  41 CGCCTGCTCC CCTCGGGTCC CCGTGCGAGC CCACGCCGGC
  81 CCCGGTGCCC GCCCGCAGCC CTGCCACTGG ACACAGGATA
 121 AGGCCCAGCG CACAGGCCCC CACGTGGACA GCATGGACCG
 161 CGGCACGCTC CCTCTGGCTG TTGCCCTGCT GCTGGCCAGC
 201 TGCAGCCTCA GCCCCACAAG TCTTGCAGAA ACAGTCCATT
 241 GTGACCTTCA GCCTGTGGGC CCCGAGAGGG ACGAGGTGAC
 281 ATATACCACT AGCCAGGTCT CGAAGGGCTG CGTGGCTCAG
 321 GCCCCCAATG CCATCCTTGA AGTCCATGTC CTCTTCCTGG
 361 AGTTCCCAAC GGGCCCGTCA CAGCTGGAGC TGACTCTCCA
 401 GGCATCCAAG CAAAATGGCA CCTGGCCCCG AGAGGTGCTT
 441 CTGGTCCTCA GTGTAAACAG CAGTGTCTTC CTGCATCTCC
 481 AGGCCCTGGG AATCCCACTG CACTTGGCCT ACAATTCCAG
 521 CCTGGTCACC TTCCAAGAGC CCCCGGGGGT CAACACCACA
 561 GAGCTGCCAT CCTTCCCCAA GACCCAGATC CTTGAGTGGG
 601 CAGCTGAGAG GGGCCCCATC ACCTCTGCTG CTGAGCTGAA
 641 TGACCCCCAG AGCATCCTCC TCCGACTGGG CCAAGCCCAG
 681 GGGTCACTGT CCTTCTGCAT GCTGGAAGCC AGCCAGGACA
 721 TGGGCCGCAC GCTCGAGTGG CGGCCGCGTA CTCCAGCCTT
 761 GGTCCGGGGC TGCCACTTGG AAGGCGTGGC CGGCCACAAG
 801 GAGGCGCACA TCCTGAGGGT CCTGCCGGGC CACTCGGCCG
 841 GGCCCCGGAC GGTGACGGTG AAGGTGGAAC TGAGCTGCGC
 881 ACCCGGGGAT CTCGATGCCG TCCTCATCCT GCAGGGTCCC
 921 CCCTACGTGT CCTGGCTCAT CGACGCCAAC CACAACATGC
 961 AGATCTGGAC CACTGGAGAA TACTCCTTCA AGATCTTTCC
1001 AGAGAAAAAC ATTCGTGGCT TCAAGCTCCC AGACACACCT
1041 CAAGGCCTCC TGGGGGAGGC CCGGATGCTC AATGCCAGCA
1081 TTGTGGCATC CTTCGTGGAG CTACCGCTGG CCAGCATTGT
1121 CTCACTTCAT GCCTCCAGCT GCGGTGGTAG GCTGCAGACC
1161 TCACCCGCAC CGATCCGGAC CACTCCTCCC AAGGACACTT
1201 GTAGCCCGGA GCTGCTCATG TCCTTGATCC AGACAAAGTG
1241 TGCCGACGAC GCCATGACCC TGGTACTAAA GAAAGAGCTT
1281 GTTGCGCATT TGAAGTGCAC CATCACGGGC CTGACCTTCT
1321 GGGACCCCAG CTGTGAGGCA GAGGACAGGG GTGACAAGTT
1361 TGTCTTGCGC AGTGCTTACT CCAGCTGTGG CATGCAGGTG
1401 TCAGCAAGTA TGATCAGCAA TGAGGCGGTG GTCAATATCC
1441 TGTCGAGCTC ATCACCACAG CGGAAAAAGG TGCACTGCCT
1481 CAACATGGAC AGCCTCTCTT TCCAGCTGGG CCTCTACCTC
1521 AGCCCACACT TCCTCCAGGC CTCCAACACC ATCGAGCCGG
1561 GGCAGCAGAG CTTTGTGCAG GTCAGAGTGT CCCCATCCGT
1601 CTCCGAGTTC CTGCTCCAGT TAGACAGCTG CCACCTGGAC
1641 TTGGGGCCTG AGGGAGGCAC CGTGGAACTC ATCCAGGGCC
1681 GGGCGGCCAA GGGCAACTGT GTGAGCCTGC TGTCCCCAAG
1721 CCCCGAGGGT GACCCGCGCT TCAGCTTCCT CCTCCACTTC
1761 TACACAGTAC CCATACCCAA AACCGGCACC CTCAGCTGCA
1801 CGGTAGCCCT GCGTCCCAAG ACCGGGTCTC AAGACCAGGA
1841 AGTCCATAGG ACTGTCTTCA TGCGCTTGAA CATCATCAGC
1881 CCTGACCTGT CTGGTTGCAC AAGCAAAGGC CTCGTCCTGC
1921 CCGCCGTGCT GGGCATCACC TTTGGTGCCT TCCTCATCGG
1961 GGCCCTGCTC ACTGCTGCAC TCTGGTACAT CTACTCGCAC
2001 ACGCGTTCCC CCAGCAAGCG GGAGCCCGTG GTGGCGGTGG
2041 CTGCCCCGGC CTCCTCGGAG AGCAGCAGCA CCAACCACAG
2081 CATCGGGAGC ACCCAGAGCA CCCCCTGCTC CACCAGCAGC
2121 ATGGCATAGC CCCGGCCCCC CGCGCTCGCC CAGCAGGAGA
2161 GACTGAGCAG CCGCCAGCTG GGAGCACTGG TGTGAACTCA
2201 CCCTGGGAGC CAGTCCTCCA CTCGACCCAG AATGGAGCCT
```

```
2241 GCTCTCCGCG CCTACCCTTC CCGCCTCCCT CTCAGAGGCC
2281 TGCTGCCAGT GCAGCCACTG GCTTGGAACA CCTTGGGGTC
2321 CCTCCACCCC ACAGAACCTT CAACCCAGTG GGTCTGGGAT
2361 ATGGCTGCCC AGGAGACAGA CCACTTGCCA CGCTGTTGTA
2401 AAAACCCAAG TCCCTGTCAT TTGAACCTGG ATCCAGCACT
2441 GGTGAACTGA GCTGGGCAGG AAGGGAGAAC TTGAAACAGA
2481 TTCAGGCCAG CCCAGCCAGG CCAACAGCAC CTCCCCGCTG
2521 GGAAGAGAAG AGGGCCCAGC CCAGAGCCAC CTGGATCTAT
2561 CCCTGCGGCC TCCACACCTG AACTTGCCTA ACTAACTGGC
2601 AGGGGAGACA GGAGCCTAGC GGAGCCCAGC CTGGGAGCCC
2641 AGAGGGTGGC AAGAACAGTG GGCGTTGGGA GCCTAGCTCC
2681 TGCCACATGG AGCCCCCTCT GCCGGTCGGG CAGCCAGCAG
2721 AGGGGGAGTA GCCAAGCTGC TTGTCCTGGG CCTGCCCCTG
2761 TGTATTCACC ACCAATAAAT CAGACCATGA AACCAAAAAA
2801 AAAAAAAAAA AAAAAAAAA AAAAAAAAA
```

Another cDNA sequence for human CD105 is available from the National Center for Biotechnology Information database as accession number NM_000118.2 (GI: 168693645; SEQ ID NO:4).

```
   1 CTCTACCCGG TTGGCAGGCG GCCTGGCCCA GCCCCTTCTC
  41 TAAGGAAGCG CATTTCCTGC CTCCCTGGGC CGGCCGGGCT
  81 GGATGAGCCG GGAGCTCCCT GCTGCCGGTC ATACCACAGC
 121 CTTCATCTGC GCCCTGGGGC CAGGACTGCT GCTGTCACTG
 161 CCATCCATTG GAGCCCAGCA CCCCCTCCCC GCCCATCCTT
 201 CGGACAGCAA CTCCAGCCCA GCCCCGCGTC CCTGTGTCCA
 241 CTTCTCCTGA CCCCTCGGCC GCCACCCCAG AAGGCTGGAG
 281 CAGGGACGCC GTCGCTCCGG CCGCCTGCTC CCCTCGGGTC
 321 CCCGTGCGAG CCCACGCCGG CCCCGGTGCC CGCCCGCAGC
 361 CCTGCCACTG GACACAGGAT AAGGCCCAGC GCACAGGCCC
 401 CCACGTGGAC AGCATGGACC GCGGCACGCT CCCTCTGGCT
 441 GTTGCCCTGC TGCTGGCCAG CTGCAGCCTC AGCCCCACAA
 481 GTCTTGCAGA AACAGTCCAT TGTGACCTTC AGCCTGTGGG
 521 CCCCGAGAGG GGCGAGGTGA CATATACCAC TAGCCAGGTC
 561 TCGAAGGGCT GCGTGGCTCA GGCCCCCAAT GCCATCCTTG
 601 AAGTCCATGT CCTCTTCCTG GAGTTCCCAA CGGGCCCGTC
 641 ACAGCTGGAG CTGACTCTCC AGGCATCCAA GCAAAATGGC
 681 ACCTGGCCCC GAGAGGTGCT TCTGGTCCTC AGTGTAAACA
 721 GCAGTGTCTT CCTGCATCTC CAGGCCCTGG GAATCCCACT
 761 GCACTTGGCC TACAATTCCA GCCTGGTCAC CTTCCAAGAG
 801 CCCCCGGGGG TCAACACCAC AGAGCTGCCA TCCTTCCCCA
 841 AGACCCAGAT CCTTGAGTGG GCAGCTGAGA GGGGCCCCAT
 881 CACCTCTGCT GCTGAGCTGA ATGACCCCCA GAGCATCCTC
 921 CTCCGACTGG GCCAAGCCCA GGGGTCACTG TCCTTCTGCA
 961 TGCTGGAAGC CAGCCAGGAC ATGGGCCGCA CGCTCGAGTG
1001 GCGGCCGCGT ACTCCAGCCT TGGTCCGGGG CTGCCACTTG
1041 GAAGGCGTGG CCGGCCACAA GGAGGCGCAC ATCCTGAGGG
1081 TCCTGCCGGG CCACTCGGCC GGGCCCCGGA CGGTGACGGT
1121 GAAGGTGGAA CTGAGCTGCG CACCCGGGGA TCTCGATGCC
1161 GTCCTCATCC TGCAGGGTCC CCCCTACGTG TCCTGGCTCA
1201 TCGACGCCAA CCACAACATG CAGATCTGGA CCACTGGAGA
1241 ATACTCCTTC AAGATCTTTC CAGAGAAAAA CATTCGTGGC
1281 TTCAAGCTCC CAGACACACC TCAAGGCCTC CTGGGGGAGG
1321 CCCGGATGCT CAATGCCAGC ATTGTGGCAT CCTTCGTGGA
1361 GCTACCGCTG GCCAGCATTG TCTCACTTCA TGCCTCCAGC
1401 TGCGGTGGTA GGCTGCAGAC CTCACCCGCA CCGATCCAGA
1441 CCACTCCTCC CAAGGACACT TGTAGCCCGA GCTGCTCAT
1481 GTCCTTGATC CAGACAAAGT GTGCCGACGA CGCCATGACC
1521 CTGGTACTAA AGAAAGAGCT TGTTGCGCAT TTGAAGTGCA
1561 CCATCACGGG CCTGACCTTC TGGGACCCCA GCTGTGAGGC
1601 AGAGGACAGG GGTGACAAGT TTGTCTTGCG CAGTGCTTAC
1641 TCCAGCTGTG GCATGCAGGT GTCAGCAAGT ATGATCAGCA
1681 ATGAGGCGGT GGTCAATATC CTGTCGAGCT CATCACCACA
1721 GCGGAAAAAG GTGCACTGCC TCAACATGGA CAGCCTCTCT
1761 TTCCAGCTGG GCCTCTACCT CAGCCCACAC TTCCTCCAGG
1801 CCTCCAACAC CATCGAGCCG GGGCAGCAGA GCTTTGTGCA
1841 GGTCAGAGTG TCCCCATCCG TCTCCGAGTT CCTGCTCCAG
1881 TTAGACAGCT GCCACCTGGA CTTGGGGCCT GAGGGAGGCA
1921 CCGTGGAACT CATCCAGGGC CGGGCGGCCA AGGGCAACTG
1961 TGTGAGCCTG CTGTCCCCAA GCCCCGAGGG TGACCCGCGC
2001 TTCAGCTTCC TCCTCCACTT CTACACAGTA CCCATACCCA
2041 AAACCGGCAC CCTCAGCTGC ACGGTAGCCC TGCGTCCCAA
2081 GACCGGGTCT CAAGACCAGG AAGTCCATAG GACTGTCTTC
2121 ATGCGCTTGA ACATCATCAG CCCTGACCTG TCTGGTTGCA
2161 CAAGCAAAGG CCTCGTCCTG CCCGCCGTGC TGGGCATCAC
2201 CTTTGGTGCC TTCCTCATCG GGGCCCTGCT CACTGCTGCA
2241 CTCTGGTACA TCTACTCGCA CACGCGTGAG TACCCCAGGC
2281 CCCCACAGTG AGCATGCCGG GCCCCTCCAT CCACCCGGGG
2321 GAGCCCAGTG AAGCCTCTGA GGGATTGAGG GGCCCTGGCC
2361 AGGACCCTGA CCTCCGCCCC TGCCCCCGCT CCCGCTCCCA
2401 GGTTCCCCCA GCAAGCGGGA GCCCGTGGTG GCGGTGGCTG
2441 CCCCGGCCTC CTCGGAGAGC AGCAGCACCA ACCACAGCAT
2481 CGGGAGCACC CAGAGCACCC CCTGCTCCAC CAGCAGCATG
```

```
2521 GCATAGCCCC GGCCCCCCGC GCTCGCCCAG CAGGAGAGAC
2561 TGAGCAGCCG CCAGCTGGGA GCACTGGTGT GAACTCACCC
2601 TGGGAGCCAG TCCTCCACTC GACCCAGAAT GGAGCCTGCT
2641 CTCCGCGCCT ACCCTTCCCG CCTCCCTCTC AGAGGCCTGC
2681 TGCCAGTGCA GCCACTGGCT TGGAACACCT TGGGGTCCCT
2721 CCACCCCACA GAACCTTCAA CCCAGTGGGT CTGGGATATG
2761 GCTGCCCAGG AGACAGACCA CTTGCCACGC TGTTGTAAAA
2801 ACCCAAGTCC CTGTCATTTG AACCTGGATC CAGCACTGGT
2841 GAACTGAGCT GGGCAGGAAG GGAGAACTTG AAACAGATTC
2881 AGGCCAGCCC AGCCAGGCCA ACAGCACCTC CCCGCTGGGA
2921 AGAGAAGAGG GCCCAGCCCA GAGCCACCTG GATCTATCCC
2961 TGCGGCCTCC ACACCTGAAC TTGCCTAACT AACTGGCAGG
3001 GGAGACAGGA GCCTAGCGGA GCCCAGCCTG GGAGCCCAGA
3041 GGGTGGCAAG AACAGTGGGC GTTGGGAGCC TAGCTCCTGC
3081 CACATGGAGC CCCCTCTGCC GGTCGGGCAG CCAGCAGAGG
3121 GGGAGTAGCC AAGCTGCTTG TCCTGGGCCT GCCCCTGTGT
3161 ATTCACCACC AATAAATCAG ACCATGAAAC CAGTGA
```

A cDNA sequence for human Toll-like receptor 4 (TLR4) is available from the National Center for Biotechnology Information database as accession number NM_138554.1 (GI:19924148; SEQ ID NO:5).

```
   1 CCTCTCACCC TTTAGCCCAG AACTGCTTTG AATACACCAA
  41 TTGCTGTGGG GCGGCTCGAG GAAGAGAAGA CACCAGTGCC
  81 TCAGAAACTG CTCGGTCAGA CGGTGATAGC GAGCCACGCA
 121 TTCACAGGGC CACTGCTGCT CACAGAAGCA GTGAGGATGA
 161 TGCCAGGATG ATGTCTGCCT CGCGCCTGGC TGGGACTCTG
 201 ATCCCAGCCA TGGCCTTCCT CTCCTGCGTG AGACCAGAAA
 241 GCTGGGAGCC CTGCGTGGAG GTGGTTCCTA ATATTACTTA
 281 TCAATGCATG GAGCTGAATT TCTACAAAAT CCCCGACAAC
 321 CTCCCCTTCT CAACCAAGAA CCTGGACCTG AGCTTTAATC
 361 CCCTGAGGCA TTTAGGCAGC TATAGCTTCT TCAGTTTCCC
 401 AGAACTGCAG GTGCTGGATT TATCCAGGTG TGAAATCCAG
 441 ACAATTGAAG ATGGGGCATA TCAGAGCCTA AGCCACCTCT
 481 CTACCTTAAT ATTGACAGGA AACCCCATCC AGAGTTTAGC
 521 CCTGGGAGCC TTTTCTGGAC TATCAAGTTT ACAGAAGCTG
 561 GTGGCTGTGG AGACAAATCT AGCATCTCTA GAGAACTTCC
 601 CCATTGGACA TCTCAAAACT TTGAAAGAAC TTAATGTGGC
 641 TCACAATCTT ATCCAATCTT TCAAATTACC TGAGTATTTT
 681 TCTAATCTGA CCAATCTAGA GCACTTGGAC CTTTCCAGCA
 721 ACAAGATTCA AAGTATTTAT TGCACAGACT TGCGGGTTCT
 761 ACATCAAATG CCCCTACTCA ATCTCTCTTT AGACCTGTCC
 801 CTGAACCCTA TGAACTTTAT CCAACCAGGT GCATTTAAAG
 841 AAATTAGGCT TCATAAGCTG ACTTTAAGAA ATAATTTTGA
 881 TAGTTTAAAT GTAATGAAAA CTTGTATTCA AGGTCTGGCT
 921 GGTTTAGAAG TCCATCGTTT GGTTCTGGGA GAATTTAGAA
 961 ATGAAGGAAA CTTGGAAAAG TTTGACAAAT CTGCTCTAGA
1001 GGGCCTGTGC AATTTGACCA TTGAAGAATT CCGATTAGCA
1041 TACTTAGACT ACTACCTCGA TGATATTATT GACTTATTTA
1081 ATTGTTTGAC AAATGTTTCT TCATTTTCCC TGGTGAGTGT
1141 GACTATTGAA AGGGTAAAAG ACTTTTCTTA TAATTTCGGA
1181 TGGCAACATT TAGAATTAGT TAACTGTAAA TTTGACAAAT
1201 TTCCCACATT GAAACTCAAA TCTCTCAAAA GGCTTACTTT
1241 CACTTCCAAC AAAGGTGGGA ATGCTTTTTC AGAAGTTGAT
1281 CTACCAAGCC TTGAGTTTCT AGATCTCAGT AGAAATGGCT
1321 TGAGTTTCAA AGGTTGCTGT TCTCAAAGTG ATTTTGGGAC
1361 AACCAGCCTA AAGTATTTAG ATCTGAGCTT CAATGGTGTT
1401 ATTACCATGA GTTCAAACTT CTTGGGCTTA GAACAACTAG
1441 AACATCTGGA TTTCCAGCAT TCCAATTTGA AACAAATGAG
1481 TGAGTTTTCA GTATTCCTAT CACTCAGAAA CCTCATTTAC
1521 CTTGACATTT CTCATACTCA CACCAGAGTT GCTTTCAATG
1561 GCATCTTCAA TGGCTTGTCC AGTCTCGAAG TCTTGAAAAT
1601 GGCTGGCAAT TCTTTCCAGG AAAACTTCCT TCCAGATATC
1641 TTCACAGAGC TGAGAAACTT GACCTTCCTG GACCTCTCTC
1681 AGTGTCAACT GGAGCAGTTG TCTCCAACAG CATTTAACTC
1721 ACTCTCCAGT CTTCAGGTAC TAAATATGAG CCACAACAAC
1761 TTCTTTTCAT TGGATACGTT TCCTTATAAG TGTCTGAACT
1801 CCCTCCAGGT TCTTGATTAC AGTCTCAATC ACATAATGAC
1841 TTCCAAAAAA CAGGAACTAC AGCATTTTCC AAGTAGTCTA
1881 GCTTTCTTAA ATCTTACTCA GAATGACTTT GCTTGTACTT
1921 GTGAACACCA GAGTTCCTG CAATGGATCA AGGACCAGAG
1961 GCAGCTCTTG GTGGAAGTTG AACGAATGGA ATGTGCAACA
2001 CCTTCAGATA AGCAGGGCAT GCCTGTGCTG AGTTTGAATA
2041 TCACCTGTCA GATGAATAAG ACCATCATTG GTGTGTCGGT
2081 CCTCAGTGTG CTTGTAGTAT CTGTTGTAGC AGTTCTGGTC
2121 TATAAGTTCT ATTTTCACCT GATGCTTCTT GCTGGCTGCA
2161 TAAAGTATGG TAGAGGTGAA AACATCTATG ATGCCTTTGT
2201 TATCTACTCA AGCCAGGATG AGGACTGGGT AAGGAATGAG
2241 CTAGTAAAGA ATTTAGAAGA AGGGGTGCCT CCATTTCAGC
2281 TCTGCCTTCA CTACAGAGAC TTTATTCCCG GTGTGGCCAT
2321 TGCTGCCAAC ATCATCCATG AAGGTTTCCA TAAAAGCCGA
2361 AAGGTGATTG TTGTGGTGTC CCAGCACTTC ATCCAGAGCC
```

```
2401 GCTGGTGTAT CTTTGAATAT GAGATTGCTC AGACCTGGCA
2441 GTTTCTGAGC AGTCGTGCTG GTATCATCTT CATTGTCCTG
2481 CAGAAGGTGG AGAAGACCCT GCTCAGGCAG CAGGTGGAGC
2521 TGTACCGCCT TCTCAGCAGG AACACTTACC TGGAGTGGGA
2561 GGACAGTGTC CTGGGGCGGC ACATCTTCTG GAGACGACTC
2601 AGAAAAGCCC TGCTGGATGG TAAATCATGG AATCCAGAAG
2641 GAACAGTGGG TACAGGATGC AATTGGCAGG AAGCAACATC
2681 TATCTGAAGA GGAAAAATAA AAACCTCCTG AGGCATTTCT
2721 TGCCCAGCTG GTCCAACAC TTGTTCAGTT AATAAGTATT
2761 AAATGCTGCC ACATGTCAGG CCTTATGCTA AGGGTGAGTA
2801 ATTCCATGGT GCACTAGATA TGCAGGGCTG CTAATCTCAA
2841 GGAGCTTCCA GTGCAGAGGG AATAAATGCT AGACTAAAAT
2881 ACAGAGTCTT CCAGGTGGGC ATTTCAACCA ACTCAGTCAA
2921 GGAACCCATG ACAAAGAAAG TCATTTCAAC TCTTACCTCA
2961 TCAAGTTGAA TAAAGACAGA GAAAACAGAA AGAGACATTG
3001 TTCTTTTCCT GAGTCTTTTG AATGGAAATT GTATTATGTT
3041 ATAGCCATCA TAAAACCATT TTGGTAGTTT TGACTGAACT
3081 GGGTGTTCAC TTTTTCCTTT TTGATTGAAT ACAATTTAAA
3121 TTCTACTTGA TGACTGCAGT CGTCAAGGGG CTCCTGATGC
3161 AAGATGCCCC TTCCATTTTA AGTCTGTCTC CTTACAGAGG
3201 TTAAAGTCTA GTGGCTAATT CCTAAGGAAA CCTGATTAAC
3241 ACATGCTCAC AACCATCCTG GTCATTCTCG AGCATGTTCT
3281 ATTTTTTAAC TAATCACCCC TGATATATTT TTATTTTTAT
3321 ATATCCAGTT TTCATTTTTT TACGTCTTGC CTATAAGCTA
3361 ATATCATAAA TAAGGTTGTT TAAGACGTGC TTCAAATATC
3401 CATATTAACC ACTATTTTTC AAGGAAGTAT GGAAAAGTAC
3441 ACTCTGTCAC TTTGTCACTC GATGTCATTC CAAAGTTATT
3481 GCCTACTAAG TAATGACTGT CATGAAAGCA GCATTGAAAT
3521 AATTTGTTTA AAGGGGGCAC TCTTTTAAAC GGGAAGAAAA
3561 TTTCCGCTTC CTGGTCTTAT CATGGACAAT TTGGGCTAGA
3601 GGCAGGAAGG AAGTGGGATG ACCTCAGGAG GTCACCTTTT
3641 CTTGATTCCA GAAACATATG GGCTGATAAA CCCGGGGTGA
3681 CCTCATGAAA TGAGTTGCAG CAGAAGTTTA TTTTTTTCAG
3721 AACAAGTGAT GTTTGATGGA CCTCTGAATC TCTTTAGGGA
3761 GACACAGATG GCTGGGATCC CTCCCCTGTA CCCTTCTCAC
3801 TGCCAGGAGA ACTA
```

A cDNA sequence for human CD14 is available from the National Center for Biotechnology Information database as accession number NM_000591.3 (GI:291575160; SEQ ID NO:6).

```
   1 CAGAGAAGGC TTAGGCTCCC GAGTCAACAG GGCATTCACC
  41 GCCTGGGGCG CCTGAGTCAT CAGGACACTG CCAGGAGACA
  81 CAGAACCCTA GATGCCCTGC AGAATCCTTC CTGTTACGGT
 121 CCCCCTCCCT GAAACATCCT TCATTGCAAT ATTTCCAGGA
 161 AAGGAAGGGG GCTGGCTCGG AGGAAGAGAG GTGGGGAGGT
 201 GATCAGGGTT CACAGAGGAG GGAACTGAAT GACATCCCAG
 241 GATTACATAA ACTGTCAGAG GCAGCCGAAG AGTTCACAAG
 281 TGTGAAGCCT GGAAGCCGGC GGGTGCCGCT GTGTAGGAAA
 321 GAAGCTAAAG CACTTCCAGA GCCTGTCCGG AGCTCAGAGG
 361 TTCGGAAGAC TTATCGACCA TGGAGCGCGC GTCCTGCTTG
 401 TTGCTGCTGC TGCTGCCGCT GGTGCACGTC TCTGCGACCA
 441 CGCCAGAACC TTGTGAGCTG GACGATGAAG ATTTCCGCTG
 481 CGTCTGCAAC TTCTCCGAAC CTCAGCCCGA CTGGTCCGAA
 521 GCCTTCCAGT GTGTGTCTGC AGTAGAGGTG GAGATCCATG
 561 CCGGCGGTCT CAACCTAGAG CCGTTTCTAA AGCGCGTCGA
 601 TGCGGACGCC GACCCGCGGC AGTATGCTGA CACGGTCAAG
 641 GCTCTCCGCG TGCGGCGGCT CACAGTGGGA GCCGCACAGG
 681 TTCCTGCTCA GCTACTGGTA GGCGCCCTGC GTGTGCTAGC
 721 GTACTCCCGC CTCAAGGAAC TGACGCTCGA GGACCTAAAG
 761 ATAACCGGCA CCATGCCTCC GCTGCCTCTG GAAGCCACAG
 801 GACTTGCACT TTCCAGCTTG CGCCTACGCA ACGTGTCGTG
 841 GGCGACAGGG CGTTCTTGGC TCGCCGAGCT GCAGCAGTGG
 881 CTCAAGCCAG GCCTCAAGGT ACTGAGCATT GCCCAAGCAC
 921 ACTCGCCTGC CTTTTCCTGC GAACAGGTTC GCGCCTTCCC
 961 GGCCCTTACC AGCCTAGACC TGTCTGACAA TCCTGGACTG
 001 GGCGAACGCG GACTGATGGC GGCTCTCTGT CCCCACAAGT
1041 TCCCGGCCAT CCAGAATCTA GCGCTGCGCA ACACAGGAAT
1081 GGAGACGCCC ACAGGCGTGT GCGCCGCACT GGCGGCGGCA
1121 GGTGTGCAGC CCCACAGCCT AGACCTCAGC CACAACTCGC
1161 TGCGCGCCAC CGTAAACCCT AGCGCTCCGA GATGCATGTG
1201 GTCCAGCGCC CTGAACTCCC TCAATCTGTC GTTCGCTGGG
1241 CTGGAACAGG TGCCTAAAGG ACTGCCAGCC AAGCTCAGAG
1281 TGCTCGATCT CAGCTGCAAC AGACTGAACA GGGCGCCGCA
1321 GCCTGACGAG CTGCCCGAGG TGGATAACCT GACACTGGAC
1361 GGGAATCCCT TCCTGGTCCC TGGAACTGCC CTCCCCCACG
1401 AGGGCTCAAT GAACTCCGGC GTGGTCCCAG CCTGTGCACG
1441 TTCGACCCTG TCGGTGGGGG TGTCGGGAAC CCTGGTGCTG
1481 CTCCAAGGGG CCCGGGGCTT TGCCTAAGAT CCAAGACAGA
1521 ATAATGAATG GACTCAAACT GCCTTGGCTT CAGGGGAGTC
1561 CCGTCAGGAC GTTGAGGACT TTTCGACCAA TTCAACCCTT
```

-continued

```
1601 TGCCCCACCT TTATTAAAAT CTTAAACAAC GGGTCAAAAA

1641 AAAAAAAA
```

A cDNA sequence for human CD46 is available from the National Center for Biotechnology Information database as accession number NM_002389.3 (GI:27502401; SEQ ID NO:7).

```
   1 GCTCGGGCCA CGCCCACCTG TCCTGCAGCA CTGGATGCTT

41 TGTGAGTTGG GGATTGTTGC GTCCCATATC TGGACCCAGA

81 AGGGACTTCC CTGCTCGGCT GGCTCTCGGT TTCTCTGCTT

121 TCCTCCGGAG AAATAACAGC GTCTTCCGCG CCGCGCATGG

161 AGCCTCCCGG CCGCCGCGAG TGTCCCTTTC CTTCCTGGCG

201 CTTTCCTGGG TTGCTTCTGG CGGCCATGGT GTTGCTGCTG

241 TACTCCTTCT CCGATGCCTG TGAGGAGCCA CCAACATTTG

281 AAGCTATGGA GCTCATTGGT AAACCAAAAC CCTACTATGA

321 GATTGGTGAA CGAGTAGATT ATAAGTGTAA AAAAGGATAC

361 TTCTATATAC CTCCTCTTGC CACCCATACT ATTTGTGATC

401 GGAATCATAC ATGGCTACCT GTCTCAGATG ACGCCTGTTA

441 TAGAGAAACA TGTCCATATA TACGGGATCC TTTAAATGGC

481 CAAGCAGTCC CTGCAAATGG GACTTACGAG TTTGGTTATC

521 AGATGCACTT TATTTGTAAT GAGGGTTATT ACTTAATTGG

561 TGAAGAAATT CTATATTGTG AACTTAAAGG ATCAGTAGCA

601 ATTTGGAGCG GTAAGCCCCC AATATGTGAA AAGGTTTTGT

641 GTACACCACC TCCAAAAATA AAAAATGGAA AACACACCTT

681 TAGTGAAGTA GAAGTATTTG AGTATCTTGA TGCAGTAACT

721 TATAGTTGTG ATCCTGCACC TGGACCAGAT CCATTTTCAC

761 TTATTGGAGA GAGCACGATT TATTGTGGTG ACAATTCAGT

801 GTGGAGTCGT GCTGCTCCAG AGTGTAAAGT GGTCAAATGT

841 CGATTTCCAG TAGTCGAAAA TGGAAAACAG ATATCAGGAT

881 TTGGAAAAAA ATTTTACTAC AAAGCAACAG TTATGTTTGA

921 ATGCGATAAG GGTTTTTACC TCGATGGCAG CGACACAATT

961 GTCTGTGACA GTAACAGTAC TTGGGATCCC CCAGTTCCAA

1001 AGTGTCTTAA AGTGCTGCCT CCATCTAGTA CAAAACCTCC

1041 AGCTTTGAGT CATTCAGTGT CGACTTCTTC CACTACAAAA

1081 TCTCCAGCGT CCAGTGCCTC AGGTCCTAGG CCTACTTACA

1121 AGCCTCCAGT CTCAAATTAT CCAGGATATC CTAAACCTGA

1161 GGAAGGAATA CTTGACAGTT TGGATGTTTG GGTCATTGCT

1201 GTGATTGTTA TTGCCATAGT TGTTGGAGTT GCAGTAATTT

1241 GTGTTGTCCC GTACAGATAT CTTCAAAGGA GGAAGAAGAA

1281 AGGCACATAC CTAACTGATG AGACCCACAG AGAAGTAAAA

1321 TTTACTTCTC TCTGAGAAGG AGAGATGAGA GAAAGGTTTG

1361 CTTTTATCAT TAAAAGGAAA GCAGATGGTG GAGCTGAATA

1401 TGCCACTTAC CAGACTAAAT CAACCACTCC AGCAGAGCAG

1441 AGAGGCTGAA TAGATTCCAC AACCTGGTTT GCCAGTTCAT

1481 CTTTTGACTC TATTAAAATC TTCAATAGTT GTTATTCTGT

1621 AGTTTCACTC TCATGAGTGC AACTGTGGCT TAGCTAATAT

1561 TGCAATGTGG CTTGAATGTA GGTAGCATCC TTTGATGCTT

1601 CTTTGAAACT TGTATGAATT TGGGTATGAA CAGATTGCCT

1641 GCTTTCCCTT AAATAACACT TAGATTTATT GGACCAGTCA

1681 GCACAGCATG CCTGGTTGTA TTAAAGCAGG GATATGCTGT

1721 ATTTTATAAA ATTGGCAAAA TTAGAGAAAT ATAGTTCACA

1761 ATGAAATTAT ATTTTCTTTG TAAAGAAAGT GGCTTGAAAT

1801 CTTTTTTGTT CAAAGATTAA TGCCAACTCT TAAGATTATT

1841 CTTTCACCAA CTATAGAATG TATTTTATAT ATCGTTCATT

1881 GTAAAAGCC CTTAAAAATA TGTGTATACT ACTTTGGCTC

1921 TTGTGCATAA AAACAAGAAC ACTGAAAATT GGGAATATGC

1961 ACAAACTTGG CTTCTTTAAC CAAGAATATT ATTGGAAAAT

2001 TCTCTAAAAG TTAATAGGGT AAATTCTCTA TTTTTTGTAA

2041 TGTGTTCGGT GATTTCAGAA AGCTAGAAAG TGTATGTGTG

2061 GCATTTGTTT TCACTTTTTA AAACATCCCT AACTGATCGA

2121 ATATATCAGT AATTTCAGAA TCAGATGCAT CCTTTCATAA

2161 GAAGTGAGAG GACTCTGACA GCCATAACAG GAGTGCCACT

2201 TCATGGTGCG AAGTGAACAC TGTAGTCTTG TTGTTTTCCC

2241 AAAGAGAACT CCGTATGTTC TCTTAGGTTA AGTAACCCAC

2281 TCTGAATTCT GGTTACATGT GTTTTTCTCT CCCTCCTTAA

2321 ATAAAGAGAG GGGTTAAACA TGCCCTCTAA AAGTAGGTGG

2361 TTTTGAAGAG AATAAATTCA TCAGATAACC TCAAGTCACA

2401 TGAGAATCTT AGTCCATTTA CATTGCCTTG GCTAGTAAAA

2441 GCCATCTATG TATATGTCTT ACCTCATCTC CTAAAAGGCA

2481 GAGTACAAAG TAAGCCATGT ATCTCAGGAA GGTAACTTCA

2521 TTTTGTCTAT TTGCTGTTGA TTGTACCAAG GGATGGAAGA

2561 AGTAAATATA GCTCAGGTAG CACTTTATAC TCAGGCAGAT

2601 CTCAGCCCTC TACTGAGTCC CTTAGCCAAG CAGTTTCTTT

2641 CAAAGAAGCC AGCAGGCGAA AAGCAGGGAC TGCCACTGCA

2681 TTTCATATCA CACTGTTAAA AGTTGTGTTT TGAAATTTTA

2721 TGTTTAGTTG CACAAATTGG GCCAAAGAAA CATTGCCTTG

2761 AGGAAGATAT GATTGGAAAA TCAAGAGTGT AGAAGAATAA

2801 ATACTGTTTT ACTGTCCAAA GACATGTTTA TAGTGCTCTG

2841 TAAATGTTCC TTTCCTTTGT AGTCTCTGGC AAGATGCTTT

2881 AGGAAGATAA AAGTTTGAGG AGAACAAACA GGAATTCTGA

2921 ATTAAGCACA GAGTTGAAGT TTATACCCGT TTCACATGCT

2961 TTTCAAGAAT GTCGCAATTA CTAAGAAGCA GATAATGGTG
```

```
3001 TTTTTTAGAA ACCTAATTGA AGTATATTCA ACCAAATACT
3041 TTAATGTATA AAATAAATAT TATACAATAT ACTTGTATAG
3081 CAGTTTCTGC TTCACATTTG ATTTTTTCAA ATTTAATATT
3121 TATATTAGAG ATCTATATAT GTATAAATAT GTATTTTGTC
3161 AAATTTGTTA CTTAAATATA TAGAGACCAG TTTTCTCTGG
3201 AAGTTTGTTT AAATGACAGA AGCGTATATG AATTCAAGAA
3241 AATTTAAGCT GCAAAAATGT ATTTGCTATA AAATGAGAAG
3281 TCTCACTGAT AGAGGTTCTT TATTGCTCAT TTTTTAAAAA
3321 ATGGACTCTT GAAATCTGTT AAAATAAAAT TGTACATTTG
3361 GAGATGTTTC A
```

A cDNA sequence for human complement factor B is available from the National Center for Biotechnology Information database as accession number NM_001710.5 (GI: 189181756; SEQ ID NO:8).

```
   1 GACTTCTGCA GTTTCTGTTT CCTTGACTGG CAGCTCAGCG
  41 GGGCCCTCCC GCTTGGATGT TCCGGGAAAG TGATGTGGGT
  81 AGGACAGGCG GGGCGAGCCG CAGGTGCCAG AACACAGATT
 121 GTATAAAAGG CTGGGGGCTG GTGGGAGCA GGGGAAGGGA
 161 ATGTGACCAG GTCTAGGTCT GGAGTTTCAG CTTGGACACT
 201 GAGCCAAGCA GACAAGCAAA GCAAGCCAGG ACACACCATC
 241 CTGCCCCAGG CCCAGCTTCT CTCCTGCCTT CCAACGCCAT
 281 GGGGAGCAAT CTCAGCCCCC AACTCTGCCT GATGCCCTTT
 321 ATCTTGGGCC TCTTGTCTGG AGGTGTGACC ACCACTCCAT
 361 GGTCTTTGGC CCGGCCCCAG GGATCCTGCT CTCTGGAGGG
 401 GGTAGAGATC AAAGGCGGCT CCTTCCGACT TCTCCAAGAG
 441 GGCCAGGCAC TGGAGTACGT GTGTCCTTCT GGCTTCTACC
 481 CGTACCCTGT GCAGACACGT ACCTGCAGAT CTACGGGGTC
 521 CTGGAGCACC CTGAAGACTC AAGACCAAAA GACTGTCAGG
 561 AAGGCAGAGT GCAGAGCAAT CCACTGTCCA AGACCACACG
 601 ACTTCGAGAA CGGGGAATAC TGGCCCCGGT CTCCCTACTA
 641 CAATGTGAGT GATGAGATCT CTTTCCACTG CTATGACGGT
 681 TACACTCTCC GGGGCTCTGC CAATCGCACC TGCCAAGTGA
 721 ATGGCCGATG GAGTGGGCAG ACAGCGATCT GTGACAACGG
 761 AGCGGGGTAC TGCTCCAACC CGGGCATCCC CATTGGCACA
 801 AGGAAGGTGG GCAGCCAGTA CCGCCTTGAA GACAGCGTCA
 841 CCTACCACTG CAGCCGGGGG CTTACCCTGC GTGGCTCCCA
 881 GCGGCGAACG TGTCAGGAAG GTGGCTCTTG GAGCGGGACG
 921 GAGCCTTCCT GCCAAGACTC CTTCATGTAC GACACCCCTC
 961 AAGAGGTGGC CGAAGCTTTC CTGTCTTCCC TGACAGAGAC
1001 CATAGAAGGA GTCGATGCTG AGGATGGGCA CGGCCCAGGG
1041 GAACAACAGA AGCGGAAGAT CGTCCTGGAC CCTTCAGGCT
1081 CCATGAACAT CTACCTGGTG CTAGATGGAT CAGACAGCAT
1121 TGGGGCCAGC AACTTCACAG GAGCCAAAAA GTGTCTAGTC
1161 AACTTAATTG AGAAGGTGGC AAGTTATGGT GTGAAGCCAA
1201 GATATGGTCT AGTGACATAT GCCACATACC CCAAAATTTG
1241 GGTCAAAGTG TCTGAAGCAG ACAGCAGTAA TGCAGACTGG
1281 GTCACGAAGC AGCTCAATGA AATCAATTAT GAAGACCACA
1321 AGTTGAAGTC AGGGACTAAC ACCAAGAAGG CCCTCCAGGC
1361 AGTGTACAGC ATGATGAGCT GGCCAGATGA CGTCCCTCCT
1401 GAAGGCTGGA ACCGCACCCG CCATGTCATC ATCCTCATGA
1441 CTGATGGATT GCACAACATG GCGGGGACC CAATTACTGT
1481 CATTGATGAG ATCCGGGACT TGCTATACAT TGGCAAGGAT
1521 CGCAAAAACC CAAGGGAGGA TTATCTGGAT GTCTATGTGT
1561 TTGGGGTCGG GCCTTTGGTG AACCAAGTGA ACATCAATGC
1601 TTTGGCTTCC AAGAAAGACA ATGAGCAACA TGTGTTCAAA
1641 GTCAAGGATA TGGAAAACCT GGAAGATGTT TTCTACCAAA
1681 TGATCGATGA AAGCCAGTCT CTGAGTCTCT GTGGCATGGT
1721 TTGGGAACAC AGGAAGGGTA CCGATTACCA CAAGCAACCA
1761 TGGCAGGCCA AGATCTCAGT CATTCGCCCT TCAAAGGGAC
1801 ACGAGAGCTG TATGGGGCT GTGGTGTCTG AGTACTTTGT
1841 GCTGACAGCA GCACATTGTT TCACTGTGGA TGACAAGGAA
1881 CACTCAATCA AGGTCAGCGT AGGAGGGGAG AAGCGGGACC
1921 TGGAGATAGA AGTAGTCCTA TTTCACCCCA ACTACAACAT
1961 TAATGGGAAA AAAGAAGCAG GAATTCCTGA ATTTTATGAC
2001 TATGACGTTG CCCTGATCAA GCTCAAGAAT AAGCTGAAAT
2041 ATGGCCAGAC TATCAGGCCC ATTTGTCTCC CCTGCACCGA
2081 GGGAACAACT CGAGCTTTGA GGCTTCCTCC AACTACCACT
2121 TGCCAGCAAC AAAAGGAAGA GCTGCTCCCT GCACAGGATA
2161 TCAAAGCTCT GTTTGTGTCT GAGGAGGAGA AAAAGCTGAC
2201 TCGGAAGGAG GTCTACATCA AGAATGGGGA TAAGAAAGGC
2241 AGCTGTGAGA GAGATGCTCA ATATGCCCCA GGCTATGACA
2281 AAGTCAAGGA CATCTCAGAG GTGGTCACCC CTCGGTTCCT
2321 TTGTACTGGA GGGAGTGAGT CCCTATGCTGA CCCCAATACT
2361 TGCAGAGGTG ATTCTGGCGG CCCCTTGATA GTTCACAAGA
2401 GAAGTCGTTT CATTCAAGTT GGTGTAATCA GCTGGGGAGT
2441 AGTGGATGTC TGCAAAAACC AGAAGCGGCA AAAGCAGGTA
2481 CCTGCTCACG CCCGAGACTT TCACATCAAC CTCTTTCAAG
2521 TGCTGCCCTG GCTGAAGGAG AAACTCCAAG ATGAGGATTT
2561 GGGTTTTCTA TAAGGGGTTT CCTGCTGGAC AGGGGCGTGG
2601 GATTGAATTA AAACAGCTGC GACAACAAAA AAAAAAAAA
2641 AAAAAA
```

A cDNA sequence for human vimentin is available from the National Center for Biotechnology Information database as accession number NM_003380.2 (GI:62414288; SEQ ID NO:9).

```
   1 GTCCCCGCGC CAGAGACGCA GCCGCGCTCC CACCACCCAC

41 ACCCACCGCG CCCTCGTTCG CCTCTTCTCC GGGAGCCAGT

81 CCGCGCCACC GCCGCCGCCC AGGCCATCGC CACCCTCCGC

121 AGCCATGTCC ACCAGGTCCG TGTCCTCGTC CTCCTACCGC

161 AGGATGTTCG GCGGCCCGGG CACCGCGAGC CGGCCGAGCT

201 CCAGCCGGAG CTACGTGACT ACGTCCACCC GCACCTACAG

241 CCTGGGCAGC GCGCTGCGCC CCAGCACCAG CCGCAGCCTC

281 TACGCCTCGT CCCCGGGCGG CGTGTATGCC ACGCGCTCCT

321 CTGCCGTGCG CCTGCGGAGC AGCGTGCCCG GGGTGCGGCT

361 CCTGCAGGAC TCGGTGGACT TCTCGCTGGC CGACGCCATC

401 AACACCGAGT TCAAGAACAC CCGCACCAAC GAGAAGGTGG

441 AGCTGCAGGA GCTGAATGAC CGCTTCGCCA ACTACATCGA

481 CAAGGTGCGC TTCCTGGAGC AGCAGAATAA GATCCTGCTG

521 GCCGAGCTCG AGCAGCTCAA GGGCCAAGGC AAGTCGCGCC

561 TGGGGGACCT CTACGAGGAG GAGATGCGGG AGCTGCGCCG

601 GCAGGTGGAC CAGCTAACCA ACGACAAAGC CCGCGTCGAG

641 GTGGAGCGCG ACAACCTGGC CGAGGACATC ATGCGCCTCC

681 GGGAGAAATT GCAGGAGGAG ATGCTTCAGA GAGAGGAAGC

721 CGAAAACACC CTGCAATCTT TCAGACAGGA TGTTGACAAT

761 GCGTCTCTGG CACGTCTTGA CCTTGAACGC AAAGTGGAAT

801 CTTTGCAAGA AGAGATTGCC TTTTTGAAGA AACTCCACGA

841 AGAGGAAATC CAGGAGCTGC AGGCTCAGAT TCAGGAACAG

881 CATGTCCAAA TCGATGTGGA TGTTTCCAAG CCTGACCTCA

921 CGGCTGCCCT GCGTGACGTA CGTCAGCAAT ATGAAAGTGT

961 GGCTGCCAAG AACCTGCAGG AGGCAGAAGA ATGGTACAAA

1001 TCCAAGTTTG CTGACCTCTC TGAGGCTGCC AACCGGAACA

1041 ATGACGCCCT GCGCCAGGCA AAGCAGGAGT CCACTGAGTA

1081 CCGGAGACAG GTGCAGTCCC TCACCTGTGA AGTGGATGCC

1121 CTTAAAGGAA CCAATGAGTC CCTGGAACGC CAGATGCGTG

1161 AAATGGAAGA GAACTTTGCC GTTGAAGCTG CTAACTACCA

1201 AGACACTATT GGCCGCCTGC AGGAIGAGAT TCAGAATATG

1241 AAGGAGGAAA TGGCTCGTCA CCTTCGTGAA TACCAAGACC

1281 TGCTCAATGT TAAGATGGCC CTTGACATTG AGATTGCCAC

1321 CTACAGGAAG CTGCTGGAAG GCGAGGAGAG CAGGATTTCT

1361 CTGCCTCTTC CAAACTTTTC CTCCCTGAAC CTGAGGGAAA

1401 CTAATCTGGA TTCACTCCCT CTGGTTGATA CCCACTCAAA

1441 AAGGACACTT CTGATTAAGA CGGTTGAAAC TAGAGATGGA

1481 CAGGTTATCA ACGAAACTTC TCAGCATCAC GATGACCTTG
```

```
1521 AATAAAAATT GCACACACTC AGTGCAGCAA TATATTACCA

1561 GCAAGAATAA AAAAGAAATC CATATCTTAA AGAAACAGCT

1601 TTCAAGTGCC TTTCTGCAGT TTTTCAGGAG CGCAAGATAG

1641 ATTTGGAATA GGAATAAGCT CTAGTTCTTA ACAACCGACA

1681 CTCCTACAAG ATTTAGAAAA AAGTTTACAA CATAATCTAG

1721 TTTACAGAAA AATCTTGTGC TAGAATACTT TTTAAAAGGT

1761 ATTTTGAATA CCATTAAAAC TGCTTTTTTT TTTCCAGCAA

1801 GTATCCAACC AACTTGGTTC TGCTTCAATA AATCTTTGGA

1841 AAAACTC
```

The CD3ε mRNA, CD105 mRNA, TLR4 mRNA, CD14 mRNA, complement factor B mRNA, vimentin mRNA, CD46 mRNA, and 18S rRNA quantified using the methods described herein have RNA sequences that are the same or complementary to those recited above, except that these RNAs have uracil-containing nucleotides instead of the thymine-containing nucleotides recited in the sequences described herein.

The CD3ε mRNA, CD105 mRNA, TLR4 mRNA, CD14 mRNA, complement factor B mRNA, vimentin mRNA, CD46 mRNA, and 18S rRNA quantified using the methods described herein, and the probes and primers described herein can exhibit some variation of sequence from those recited herein. For example, the CD3ε mRNA, CD105 mRNA, TLR4 mRNA, CD14 mRNA, complement factor B mRNA, vimentin mRNA, CD46 mRNA, and 18S rRNA quantified using the methods described herein, and the probes and primers described herein, can have at least 70% sequence identity, or at least 80% sequence identity, or at least 90%, or at least 91% sequence identity, or at least 93% sequence identity, or at least 95% sequence identity, or at least 96%, or at least 97% sequence identity, or at least 98% sequence identity, or at least 99% sequence identity, or at least 99.5% sequence identity to the sequences described herein.

The level of expression is determined for one or more of the foregoing genes in sample obtained from a subject. For example, the quantity of expression of at least two of the foregoing genes, or at least three of the foregoing genes, or at least four of the foregoing genes, or at least five of the foregoing genes, or at least six of the foregoing genes is determined. In some instances, the quantity of expression of at least five or six of the foregoing genes is determined.

The sample can be a fluid sample such as a blood sample, a peripheral blood mononuclear cell (PBMC) sample, a urine sample, a sample of broncho-alveolar lavage fluid, a sample of bile, pleural fluid or peritoneal fluid, any other fluid secreted or excreted by a normally or abnormally functioning allograft, or any other fluid resulting from exudation or transudation through an allograft or in anatomic proximity to an allograft, or any fluid in fluid communication with the allograft. One convenient example of a sample for determination of the level of gene expression is a urine sample, for example, cells present or obtained from a urine sample.

RNA can be isolated from the samples by procedures available in the art. Commercially available kits can be employed for such isolation. Alternatively, the urine sample can be treated to lyse any cells therein and the RNA expression levels can be determined with little or no RNA purification step.

For example, the quantity of CD3ε mRNA, CD105 mRNA, TLR4 mRNA, CD14 mRNA, complement factor B mRNA, vimentin mRNA, CD46 mRNA, 18S rRNA, or a combination thereof can be determined from a urinary cell sample from the recipient of an organ transplant. Any method known to those in the art can be employed for determining the level of CD3ε mRNA, CD105 mRNA, TLR4 mRNA, CD14 mRNA, complement factor B mRNA, vimentin mRNA, CD46 mRNA, 18S rRNA or a combination thereof. For example, total RNA, which includes mRNA, tRNA, and rRNA, can be isolated from the sample by use of a commercial kit, such as the TRI Reagent® commercially available from Molecular Research Center, Inc. (Cincinnati, Ohio), can be used to isolate RNA.

Any method known to those in the art can be employed for determining the level of gene expression. For example, one method for measuring gene expression is by real-time RT-PCR. Classical TaqMan® Gene Expression Assays or TaqMan® Low Density Array microfluidic cards (Applied Biosystems) can be employed. Such methods provide quantitative measurements of RNA levels.

In another example, a microarray can be used. Microarrays are known in the art and consist of a surface to which probes that correspond in sequence to gene products (e.g. mRNAs, rRNAs, polypeptides, fragments thereof etc.) can be specifically hybridized or bound to a known position. Hybridization intensity data detected by the scanner are automatically acquired and processed by the Affymetrix Microarray Suite (MASS) software. Raw data is normalized to expression levels using a target intensity of 150.

The transcriptional state of a cell may be measured by other gene expression technologies known in the art. For example, the RNA can be reverse transcribed into cDNA and then quantity of cDNA can be measured. Technologies can be used that produce pools of restriction fragments of limited complexity for electrophoretic analysis, such as methods combining double restriction enzyme digestion with phasing primers (e.g. EP-A1-0534858), or methods selecting restriction fragments with sites closest to a defined RNA end (e.g. Prashar et al; Proc. Nat. Acad. Sci., 93, 659-663, 1996). Other methods statistically sample cDNA pools, such as by sequencing sufficient bases (e.g. 20-50 bases) in each multiple cDNAs to identify each cDNA, or by sequencing short tags (e.g. 9-10 bases) which are generated at known positions relative to a defined RNA end (e.g. Velculescu, Science, 270, 484-487, 1995) pathway pattern.

The quantification of CD3ε mRNA, CD105 mRNA, TLR4 mRNA, CD14 mRNA, complement factor B mRNA, vimentin mRNA, CD46 mRNA, 18S rRNA, or a combination thereof from the total RNA of a sample can be performed by any method known to those in the art. For example, kinetic, quantitative PCR involves reverse transcribing CD3ε mRNA, CD105 mRNA, TLR4 mRNA, CD14 mRNA, complement factor B mRNA, vimentin mRNA, CD46 mRNA, 18S rRNA, or a combination thereof by using reverse-transcriptase polymerase chain reaction (RT-PCR) to obtain cDNA copies of CD3ε mRNA, CD105 mRNA, TLR4 mRNA, CD14 mRNA, complement factor B mRNA, vimentin mRNA, CD46 mRNA, 18S rRNA, or a combination thereof. The cDNA can then, for example, be amplified by PCR followed by quantification using a suitable detection apparatus. Determination of CD3ε mRNA, CD105 mRNA, TLR4 mRNA, CD14 mRNA, complement factor B mRNA, vimentin mRNA, CD46 mRNA, 18S rRNA, or a combination thereof of expression levels can involve a preamplification step followed by an amplification process. See Examples 1 and 3 for exemplary methods for quantification of CD3ε mRNA, CD105 mRNA, TLR4 mRNA, CD14 mRNA, complement factor B mRNA, vimentin mRNA, CD46 mRNA, 18S rRNA, or a combination thereof by kinetic, quantitative PCR.

Amplification systems utilizing, for example, PCR or RT-PCR methodologies are available to those skilled in the art. For a general overview of amplification technology, see, for example, Dieffenbach et al., PCR Primer: A Laboratory Manual, Cold Spring Harbor Laboratory Press, New York (1995).

An alternative method for determining the level of CD3ε mRNA, CD105 mRNA, TLR4 mRNA, CD14 mRNA, complement factor B mRNA, vimentin mRNA, CD46 mRNA, 18S rRNA, or a combination thereof includes the use of molecular beacons and other labeled probes useful in, for example multiplex PCR. In a multiplex PCR assay, the PCR mixture contains primers and probes directed to the CD3ε mRNA, CD105 mRNA, TLR4 mRNA, CD14 mRNA, complement factor B mRNA, vimentin mRNA, CD46 mRNA, 18S rRNA, or a combination thereof. Typically, a single fluorophore is used in the assay. The molecular beacon or probe is detected to determine the level of CD3ε mRNA, CD105 mRNA, TLR4 mRNA, CD14 mRNA, complement factor B mRNA, vimentin mRNA, CD46 mRNA, 18S rRNA, or a combination thereof. Molecular beacons are described, for example, by Tyagi and Kramer (Nature Biotechnology 14, 303-308, (1996)) and by Andrus and Nichols in U.S. Patent Application Publication No. 20040053284.

Another method includes, for instance, quantifying cDNA (obtained by reverse transcribing the CD3ε mRNA, CD105 mRNA, TLR4 mRNA, CD14 mRNA, complement factor B mRNA, vimentin mRNA, CD46 mRNA, 18S rRNA, or a combination thereof using a fluorescence based real-time detection method, such as the ABI PRISM 7500, 7700, or 7900 Sequence Detection System (TaqMan®) commercially available from Applied Biosystems, Foster City, Calif., or similar system as described by Heid et al., (Genome Res. 1996; 6:986-994) and Gibson et al. (Genome Res. 1996; 6:995-1001).

The quantities of RNA expression are conveniently expressed as RNA copies per microgram of total RNA. A standard curve of RNA copy numbers in the selected RNA measurement (e.g., PCR) assays can range, for example, from 25 to 5 million copies, 25 to 3 million copies, or from 25 to 2.5 million copies. When mRNA copy numbers are measured as less than 25 can be scored as 12.5 copies per microgram of total RNA. Measurements of 18S rRNA that are greater than $5 \times 10^7$ copies/microgram total RNA can be used as a measure of transcript adequacy in that sample specimen.

Generally, the level of CD3ε mRNA, CD105 mRNA, TLR4 mRNA, CD14 mRNA, complement factor B mRNA, vimentin mRNA, CD46 mRNA, 18S rRNA, or a combination thereof in a sample is upregulated if the quantity of expression of CD3ε mRNA, CD105 mRNA, TLR4 mRNA, CD14 mRNA, complement factor B mRNA, vimentin mRNA, CD46 mRNA, 18S rRNA, or a combination thereof is increased beyond a baseline level. In some embodiments, upregulation includes increases above a baseline level of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or higher. In some instances, the "increased expression" means detection of expression that is greater than a baseline level by 2-fold, 3-fold, 5-fold, 7-fold, 8-fold, 9-fold, 10-fold, or more. "Increased expression" can also mean detection of expression with a six-signature of greater than about −0.24, or greater than about −0.2, or greater than about −0.1, or greater than about 0.0, or greater than about 0.1, or greater than about 0.2, or greater than about 0.3, or greater than about 0.4. "Increased expression" can also mean detection of expression with a five-gene signature that is greater than about A five-gene diagnostic signature of greater than about 9.24, or greater than about 9.3, or greater than about 9.4, or greater than about 9.5, or greater than about 9.6, or greater than about 9.7, or greater than about 9.8, or greater than about 9.9.

The level of CD3ε mRNA, CD105 mRNA, TLR4 mRNA, CD14 mRNA, complement factor B mRNA, vimentin mRNA, CD46 mRNA, 18S rRNA, or a combination thereof in a sample is down-regulated if the quantity of expression of CD3ε mRNA, CD105 mRNA, TLR4 mRNA, CD14 mRNA, complement factor B mRNA, vimentin mRNA, CD46 mRNA, 18S rRNA, or a combination thereof is decreased below a baseline. For example, down-regulation can include decreases below a baseline level by 10%, 15%, 20%, 25%, 30%, 35%, 40%, 45%, 50%, 55%, 60%, 65%, 70%, 75%, 80%, 85%, 90%, 95%, 100% or more below the baseline.

The level of CD3ε mRNA, CD105 mRNA, TLR4 mRNA, CD14 mRNA, complement factor B mRNA, vimentin mRNA, CD46 mRNA, 18S rRNA, or a combination thereof in a sample is generally unchanged if the quantity of expression of CD3ε mRNA, CD105 mRNA, TLR4 mRNA, CD14 mRNA, complement factor B mRNA, vimentin mRNA, CD46 mRNA, 18S rRNA, or a combination thereof does not vary significantly from a baseline. In such instances a transplanted tissue in patient with a sample having unchanged level of measured expression of CD3ε mRNA, CD105 mRNA, TLR4 mRNA, CD14 mRNA, complement factor B mRNA, vimentin mRNA, CD46 mRNA, 18S rRNA, or a combination thereof likely is not being rejected (e.g., no acute rejection), and will likely not be rejected. For example, variance from a baseline level of 0.1%, 0.2%, 0.5%, 1%, 2%, 3%, 4% or less is not sufficiently significant and the level of CD3ε mRNA, CD105 mRNA, TLR4 mRNA, CD14 mRNA, complement factor B mRNA, vimentin mRNA, CD46 mRNA, 18S rRNA, or a combination thereof in a sample is generally unchanged if such variance is measured.

As used herein the "level" of expression means the amount of expression. The level or amount can be described as RNA copy number per microgram of total RNA in a sample.

The baseline level of expression can be a level of expression of a gene in a healthy or control group of patients. For example, the baseline level of expression can be a level of expression that distinguishes one type of kidney problem from another. In such a situation, the control group can be the average or median level of expression for the gene in urinary cells from a group of patients with a known kidney problem. For example, for distinguishing acute rejection from acute tubular injury, the baseline level can be the average or median level of expression for the gene in urinary cells from acute tubular injury patients. For distinguishing acute cellular rejection from antibody mediated rejection, the baseline level can be the average or median level of expression for the gene in urinary cells from antibody mediated rejection patients.

A discriminatory level of upregulated gene expression of CD3ε mRNA, CD105 mRNA, TLR4 mRNA, CD14 mRNA, complement factor B mRNA, vimentin mRNA, CD46 mRNA, 18S rRNA, or a combination thereof, or a combination thereof, includes the mean ±95% confidence interval of a group of values observed in transplant recipients that is above the baseline group level or the control group level. Upregulation of CD3ε mRNA, CD105 mRNA, TLR4 mRNA, CD14 mRNA, complement factor B mRNA, vimentin mRNA, CD46 mRNA, 18S rRNA, or a combination thereof expression is considered to be significantly greater if the value is greater than the mean ±95% confidence interval of a group of values observed for the baseline group level or the control group level. Similarly, the level of CD3ε mRNA, CD105 mRNA, TLR4 mRNA, CD14 mRNA, complement factor B mRNA, vimentin mRNA, CD46 mRNA, 18S rRNA, or a combination thereof in the sample is considered to be significantly lower if the amount of CD3ε mRNA, CD105 mRNA, TLR4 mRNA, CD14 mRNA, complement factor B mRNA, vimentin mRNA, CD46 mRNA, 18S rRNA, or a combination thereof detected is lower than the mean ±95% confidence interval of the amount detected for the baseline group level or the control group level.

In some embodiments, the expression level is determined using natural log-transformed levels of CD3ε mRNA, CD105 mRNA, TLR4 mRNA, CD14 mRNA, complement factor B mRNA, vimentin mRNA, CD46 mRNA, 18S rRNA, or a combination thereof in a urine cell sample from the patient. The natural log transformation or RNA levels can reduce the positive skew in the data.

In some embodiments, the level of gene expression is determined using natural log-transformed RNA levels determined by normalizing RNA levels to a normalizer using a logistic regression model of CD3ε mRNA, CD105 mRNA, TLR4 mRNA, CD14 mRNA, complement factor B mRNA, vimentin mRNA, CD46 mRNA, 18S rRNA, or a combination thereof or a weighted combination of log transformed, normalized RNA levels of CD3ε mRNA, CD105 mRNA, TLR4 mRNA, CD14 mRNA, complement factor B mRNA, vimentin mRNA, CD46 mRNA, 18S rRNA, or a combination thereof based on a logistic regression model. Logistic regression models are used for prediction of the probability of occurrence of acute rejection by fitting data to a logistic curve. It is a generalized linear model used for binomial regression.

In some embodiments, for interpretation of quantitative gene expression measurements, a normalizer may be used to correct expression data for differences in cellular input, RNA quality, and RT efficiency between samples. In some embodiments, to accurately assess whether measured RNA levels are significant, the RNA expression can be normalized to accurately compare levels of expression between samples, for example, between a baseline level and an expression level detected in a test sample. Reverse Transcriptase-PCR (RT-PCR) normalization can be performed using normalizers such as one or more housekeeping RNAs as references against the expression level of a gene under investigation. Normalization includes rendering the measured values of RNA expression from different arrays or PCR or in particular RT-PCR experiments comparable by reducing or removing the technical variability. Within these experiments there exists a multiplicity of sources capable of falsifying the measurements. Possible technical sources of interference are: different efficiency in reverse transcription, labeling or hybridization reactions, as well as problems with the arrays, batch effects in reagents, or lab-specific conditions. A more robust or accurate measurement of RNA expression may occur when normalization is employed.

Normalization can involve use of a "housekeeping RNA" as a normalizer. Such a housekeeping RNA can be utilized as a reference, internal control or reference value in the quantification of RNA expression. The housekeeping RNA allows an identification and quantitative analysis of a RNA expression whose expression is regulated differentially in different pathological conditions. A housekeeping RNA exhibits minimum change of expression and transcription across different RNA samples and thus serves as a control, or reference, for the measurement of variable RNA expression levels across different samples. Housekeeping RNAs for mRNA detection include those RNAs expressed from genes such as 2-Microglobulin (β2M), Glucose-6-phosphate dehydrogenase (G6PDH), 5-aminolevulinate synthase (ALAS or ALAS 1) Hypoxanthinephophoribosyltransferase (HPRT), Porphobilinogen deaminase (PBGD), 18S rRNA, or the like. Various housekeeping RNAs and normalization reagents are available from many sources including Applied Biosystems, (Foster City, Calif.), and geNorm® kits Hoffmann-La Roche (Nutley, N.J.).

Development of Molecular Signatures to Identify Tissue Rejection

The inventors' goal was to develop noninvasive molecular signatures of urinary RNA expression levels that differentiate common causes of acute kidney allograft dysfunction-a condition where an increase in serum creatinine suggests acute rejection and triggers a for-cause biopsy. Physicians generally do not predict the histology of acute graft dysfunction well (Al-Awwa et al., *Am J Kidney Dis* 31: S15-18 (1998); Pascual et al., *Transplantation* 67: 737-741 (1999)). A sizable proportion of biopsies performed to confirm acute rejection are in fact not acute rejection, and thus could have been avoided (Pascual et al., *Transplantation* 67: 737-741 (1999)).

As described herein, the inventors have discovered and cross-validated urinary cell RNA signatures for the noninvasive diagnosis of acute allograft dysfunction. The molecular signatures were better predictors of the status of a transplanted tissue than any individual mRNA or clinical parameter conventionally employed by the medical community, including those based on the time of biopsy, serum creatinine levels, tacrolimus trough concentration measured at the time of a for-cause biopsy, or a combination thereof.

The data described herein show that among patients who had for-cause kidney allograft biopsies for acute allograft dysfunction, a 6-gene signature differentiates acute rejection from acute tubular injury (ATI). This signature is not only accurate but its clinical implementation would be beneficial. The data also show that among patients with acute rejection, a 5-gene signature differentiates acute cellular rejection (ACR) from antibody mediated rejection (AMR).

Several features the experiments described herein have contributed to the development of robust noninvasive signatures. First, the three groups that were studied were well characterized with no overlap in histological features (Table 2). Second, the refinement of the standard RT-PCR assays allowed for absolute quantification of levels of mRNAs of interest. Third, a mechanistically informative mRNA panel was used. Fourth, a two-step sequential approach was used to differentiate the three diagnostic categories of ACR, AMR and ATI. The relatively large number of patients with AMR was also a positive aspect of the study.

An important attribute of the signatures described herein is that the heterogeneity in patient and transplant-related characteristics did not undermine the ability of the signatures to differentiate acute rejection from ATI, and ACR from AMR. Also only the cross validated results of the signatures are reported, potentially minimizing the upward bias of the estimate due to model overfit. The cross-validated AUC of 0.92 for the 6-gene signature distinguishing acute rejection from ATI and the cross-validated AUC of 0.81 for the 5-gene signature distinguishing ACR from AMR shows very good discrimination. These AUCs are the expected values in an independent sample that has not been used for deriving the diagnostic signatures.

A newly developed test can be accurate, but, in patient management, may or may not be useful compared to existing strategies (Vickers, *Am Stat* 62: 314-320 (2008)). From a clinical perspective, the 6-gene signature differentiating acute rejection from ATI is may have more significant clinical benefits than the 5-gene signature distinguishing ACR from AMR. The clinical benefit of the 6-gene signature was evaluated using decision curve analysis (Vickers et al., *Med Decis Making* 26: 565-574 (2006); Steyerberg et al., *Med Decis Making* 28: 146-149 (2008)). The advantage of this approach is that it provides a quantitative estimate of the benefit of a new test compared to the existing strategy. The proportion of samples with acute rejection (62%) and ATI (38%) in the studies described herein is a reasonable approximation that can be expected in consecutive biopsies done for acute allograft dysfunction (Kon et al., *Transplantation*, 63: 547-550 (1997)). Thus approximately 35-40% of biopsies done to confirm acute rejection is in fact not acute rejection and can potentially be avoided. Instead of the current strategy of 'biopsy all' to confirm acute rejection, if the physician uses the 6-gene signature, then, a substantial number of biopsies can be avoided without an undue number of patients with acute rejection experiencing delayed diagnosis. This benefit is present across a range of reasonable physician threshold probabilities to do a biopsy.

Moreover, cost of the described PCR assay is about $300, and at the inventors' institution, the Medicare reimbursement for a kidney biopsy is about $3000. Thus, the use of 6-gene signature for clinical decision results in substantial cost savings. Among patients thus identified as acute rejection, incorporating the 5-gene signature in the decision process, for example, by treating acute cellular rejection based on the signature with high dose intravenous corticosteroids and restricting biopsies only for antibody mediated rejection (AMR), a condition that requires complex treatment decisions, or for patients with acute cellular rejection who do not respond to corticosteroids, will further reduce the need for invasive biopsies.

A pre-amplification protocol for the PCR assay allows for measurement of several RNAs in small quantity of cDNA. The turnaround time for the PCR assay is about six hours; the same time needed for a provisional read on biopsies, but PCR assays incur only a fraction of the cost of biopsies. This is especially important in the current health care cost-conscious environment.

Other biomarkers have been evaluated for the diagnosis of acute allograft dysfunction. In a study of 182 consecutive kidney transplant recipients, urinary neutrophil gelatinase-associated lipocalin (NGAL) protein levels were higher in 9 patients with biopsy proven acute rejection compared to the 35 patients with other causes of acute kidney injury. However, clinical criteria rather than biopsy were used to define acute kidney injury. Moreover creatinine levels were also different between patients with acute rejection and acute kidney injury (Heyne et al., *Transplantation* 93: 1252-1257 (2012)). In a recent study, peripheral blood mononuclear cell levels of IL-6 protein differentiated 29 patients with rejection (12 ACR, 7 AMR and 10 borderline) from the 35 with no rejection (6 ATI, 20 chronic damage, 9 others) with an AUC 0.79 in a training cohort and 0.85 in the validation cohort. However there were very few ATI, an important masquerade of acute rejection. Moreover IL-6 levels did not differentiate ACR from AMR (De Serres et al., *Clin J Am Soc Nephrol* 7: 1018-1025 (2012)). In a study of 21 ACR and 8 AMR, urinary protein levels of endothelial protein c receptor differentiated ACR from AMR with an AUC of 0.875. This study however did not include patients with ATI (Lattenist et al., *PLoS ONE* 8: e64994 (2013)).

An important consideration in evaluating the clinical utility of the signature developed in the studies described herein is the impact of infection on the diagnostic accuracy of the signatures. The findings from the recent Clinical Trials of Transplantation-04 (CTOT-04) study revealed that while bacterial urinary tract infection, blood infection and CMV infection do not impact the diagnostic accuracy of the signature, BK virus infection does impact the signature (Suthanthiran et al., *N Engl J Med* 369: 20-31 (2013)). Therefore the clinical decision to biopsy or not, could be made independent of the presence of UTI, blood infection and CMV but the signature would not necessarily obviate a biopsy in the presence of BK virus infection.

Urinary cell mRNA profiles have been recently validated in a multicenter trial (CTOT-04 study) as robust biomarkers of ACR (Suthanthiran et al., *N Engl J Med* 369: 20-31 (2013)). In that study, a three-gene signature of 18S rRNA normalized measures of CD3ε, IP-10 and 18S rRNA distinguished biopsies showing ACR from biopsies not showing rejection, and the cross-validated estimate of the AUC was 0.83 by bootstrap resampling. However there were only nine AMR-biopsy matched urine samples in the multicenter trial that precluded an analysis of the utility of the 3-gene signature in diagnosing AMR. The IP-10 mRNA levels were not measure in the current study as the diagnostic accuracy of the 3-gene signature was not known to the inventors when the experiments were designed for using the 26-member RNA panel. Hence, in the studies described herein, there is no comparison of the performance of the signatures developed in this study with the signature developed in the multicenter trial. Two transcripts measured in both studies—CD3ε mRNA and 18S rRNA—are significantly associated with ACR biopsy diagnosis in both studies.

Thus, the inventors have discovered and validated urinary cell mRNA based signatures for the differential diagnosis of acute dysfunction of kidney allografts. The signatures can be incorporated in clinical decisions for managing kidney transplant recipients with acute allograft dysfunction, potentially avoiding substantial number of biopsies.

The method can detect or predict kidney dysfunction (e.g., acute cellular rejection) a number of days prior to acute rejection. For example, the method can detect or predict kidney dysfunction (e.g., acute cellular rejection) 90 to 3 days before rejection is detectable by biopsy, or 80 to 5 days before confirmation by biopsy, or 70 to 10 days before confirmation by biopsy. Kidney transplant dysfunction such as acute cellular rejection can be predicted about 3 months to about two weeks before it happens.

If an increase or decrease in of CD3ε mRNA, CD105 mRNA, TLR4 mRNA, CD14 mRNA, complement factor B mRNA, vimentin mRNA, CD46 mRNA, 18S rRNA, or a combination thereof expression levels is determined, the patient can be informed that there is increased risk of developing transplant rejection. The increased risk varies in different patients, and the organ transplanted. Generally, the increased risk for developing acute rejection is at least about 25%, at least about 50%, at least about 75%, or at least about 90%, or at least about 99% or at least about 100%.

The method can further comprise determining the patient's serum creatinine protein level. The determination of the level of serum creatinine can be made by any method known to those skilled in the art. The next step in this embodiment can include correlating the level of serum creatinine in peripheral blood with predicting acute rejection and eventual loss of the transplanted organ. A significantly greater level of serum creatinine in peripheral blood and increased levels of CD3ε mRNA, CD105 mRNA, TLR4 mRNA, CD14 mRNA, complement factor B mRNA, vimentin mRNA, CD46 mRNA, 18S rRNA, or a combination thereof in urinary cells correlates with acute rejection and may also increase risk of loss of the transplanted kidney.

Generally, the level of serum creatinine in peripheral blood is considered to be significantly greater if the level is at least about 25% greater than the level of creatinine in a control sample. Commercial kits can be utilized to test creatinine. An example of a commercial kit for determining creatinine level is the QuantiChrom® Creatinine Assay Kit from BioAssay Systems (Hayward, Calif.).

A control or baseline level of serum creatinine can be the level of serum creatinine in peripheral blood of a healthy person or a person with a well-functioning (e.g., stable) transplant. For example, the normal level of serum creatinine in a healthy person or a person with a well-functioning transplant is generally about 0.8-1.6 milligrams/deciliter. In either case, the person may be the patient or a person different from the patient.

It is not necessary to determine the level of creatinine in a control sample every time the method is conducted. For example, the serum creatinine level from the patient can be compared to that of one or more previously determined control samples or to a level recognized by the physician or clinician conducting the method, or by a consensus of medical and/or clinical practitioners.

Diagnostic Signature

Diagnostic signature algorithms are provided herein that can be employed in a method for detecting, monitoring and diagnosing kidney function from a urinary cell samples obtained from a subject. A six-gene signature is useful for detecting or predicting the development of acute rejection of a transplanted organ such as a kidney. A five-gene signature is useful for distinguishing acute cellular rejection (ACR) from antibody-mediated rejection (AMR).

A method for detecting developing or existing acute rejection of a kidney transplant in a subject from a urine sample obtained from the subject can involve:

(a) measuring an amount of CD3ε mRNA, CD105 mRNA, TLR4 mRNA, CD14 mRNA, complement factor B mRNA, vimentin mRNA, or a combination thereof copy number per microgram of total RNA in a urine cell sample;

(b) ascertaining a diagnostic signature of developing or existing acute rejection of a kidney transplant in the subject with the following algorithm:

$$(0.52*\ln CD3\epsilon)+(1.02*\ln CD105)+(0.81*\ln TLR4)+ \\ (-1.16*\ln CD14)+(0.28*\ln \text{Complement Factor} \\ B)+(-0.79*\ln \text{Vimentin}); \text{ and}$$

(c) identifying whether the diagnostic signature is greater than about −0.24.

A signature greater than about −0.24 indicates that the transplanted kidney in the patient from whom the tested sample was obtained can be acutely rejecting the transplanted kidney, or will develop acute rejection of the transplanted kidney. For example, a six-gene diagnostic signature of −0.2, or greater than −0.1, or greater than 0, or greater than 0.1, or greater than 0.2, or greater than 0.3, or greater than 0.4 indicates that the transplanted kidney in the patient from whom the tested sample was obtained can be acutely rejecting the transplanted kidney, or will develop acute rejection of the transplanted kidney.

In general, a six-gene diagnostic signature of less than about −0.25 indicates that the transplanted kidney in the patient from whom the tested sample was obtained is not acutely rejecting the transplanted kidney. However, when a sample has a six-gene diagnostic signature of less than about −0.25, the patient from whom the sample was obtained can have a kidney with acute tubular injury (ATI). For example, samples with a six-gene diagnostic signature of less than about −0.3, or less than about −0.35, or less than about −0.4, or less than about −0.45, or less than about −0.5, or less than about −0.6 can mean that the patient from whom the sample was obtained has a kidney with acute tubular injury (ATI).

A method for distinguishing acute cellular rejection (ACR) from antibody-mediated rejection (AMR) of a kidney transplant in a subject from a urine sample obtained from the subject can involve:

(a) measuring an amount of CD3ε, CD105, CD14, CD46, 18S rRNA or a combination thereof copy number per microgram of total RNA in a urine cell sample;

(b) ascertaining a diagnostic signature of The five-gene model involved natural log (ln) transformation of acute cellular rejection (ACR) versus antibody-mediated rejection (AMR) using the following algorithm:

(0.67*ln CD3ε)+(−1.18*ln CD105)+(1.30*ln CD14)+(−0.83*ln CD46)+(0.45*ln 18S); and (c) identifying whether the diagnostic signature is greater than 9 to distinguish or identify acute rejection of the kidney transplant.

A five-gene diagnostic signature of greater than about 9.24 indicates that the transplanted kidney in the patient from whom the tested sample was obtained is undergoing acute cellular rejection, or will develop acute cellular rejection (rather than from antibody-mediated rejection). For example, a five-gene diagnostic signature of greater than about 9.3, or greater than about 9.4, or greater than about 9.5, or greater than about 9.6, or greater than about 9.7, or greater than about 9.8, or greater than about 9.9 indicates that the transplanted kidney in the patient from whom the tested sample was obtained is undergoing acute cellular rejection, or will develop acute cellular rejection.

In general, a five-gene diagnostic signature of less than about 9.24 indicates that the transplanted kidney in the patient from whom the tested sample was obtained is undergoing antibody-mediated rejection rather than acute cellular rejection. For example, a five-gene diagnostic signature of than about 9.1, or less than about 9.0, or less than 8.0, or less than about 7.0, or less than 6.0, or less than 5.0 indicates that the transplanted kidney in the patient from whom the tested sample was obtained is undergoing antibody-mediated rejection rather than acute cellular rejection.

Treatment

The methods of assaying for kidney rejection can further include informing medical personnel or the patient about the test results. Information about whether the patient will have acute rejection can also be communicated. If the patient is likely to develop kidney dysfunction, the patient can be prescribed and/or administered a treatment to delay rejection of the transplanted organ.

The methods of assaying for kidney rejection can further include treatment of kidney conditions such as kidney transplant rejection, acute tubular injury, acute cellular rejection (ACR), or antibody-mediated rejection (AMR).

Such treatment can include increased or decreased dose of an anti-rejection agent or an anti-rejection agent can be added. Anti-rejection agents, include for example, azathioprine, cyclosporine, FK506, tacrolimus, mycophenolate mofetil, anti-CD25 antibodies, anti-thymocyte globulin, rapamycin, ACE inhibitors, perillyl alcohol, anti-CTLA4 antibodies, anti-CD40L antibodies, anti-thrombin III, tissue plasminogen activator, antioxidants, anti-CD154 antibodies, anti-CD3 antibodies, lymphocyte-depleting antibodies, thymoglobin, OKT3, cortico steroids, or a combination thereof.

For example, if acute rejection is predicted, a steroid pulse therapy can be started and may include the administration for three to six days of a high dose corticosteroid (e.g., greater than 100 mg). A maintenance regimen of prednisone doses can be used if the patient is not receiving steroid treatment. One or more antibody preparations can be added for treatment of acute rejection (e.g., acute cellular rejection). Examples antibody therapy that can be used for treatment of acute rejection include the administration for seven to fourteen days of a lymphocyte-depleting antibody, a polyclonal antibody against Thymoglobin, or the monoclonal antibody OT3 (an anti-CD3 antibody).

Another example of a treatment that can be administered, for example for antibody-mediated rejection, is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded. Other examples, of treatments for antibody mediated acute rejection include intravenous immunoglobulin, and/or anti-CD20 antibodies.

Drugs that can be employed for treatment of patients having a rejection episode include mycophenolate and/or azathioprine.

Kits

The methods can also be performed by use of kits that are described herein. In general, kits can include a detection reagent that is suitable for detecting the presence of one or more RNA of interest.

The kits can include a panel of probe and/or primer sets. Such probe and/or primer sets are designed to detect expression of one or more genes and provide information about the rejection of a transplant organ. Probe sets can include probes or primers that are labeled (e.g., fluorescer, quencher, etc.). Unlabeled probes or primers can also be provided in the kits.

The probes and primers are useful for detection of CD3ε mRNA, CD105 mRNA, TLR4 mRNA, CD14 mRNA, complement factor B mRNA, vimentin mRNA, CD46 mRNA, 18S rRNA, or a combination thereof. The probe and/or primer sets are targeted at the detection of RNA transcripts and/or structural RNAs that are informative about acute rejection. Probe and/or primer sets may also comprise a large or small number of probes or primers that detect gene transcripts that are not informative about transplant rejection. Such probes and primers are useful as controls and for normalization. Probe and/or primer sets can be provided in the kits as a dry material or dissolved in solution. In some embodiments, probe and/or primer sets can be affixed to a solid substrate to form an array of probes. Probe and/or primer sets can be configured for multiplex PCR. The probes and/or primers can be nucleic acids (e.g., DNA, RNA, chemically modified forms of DNA and RNA), LNA, or PNA, or any other polymeric compound capable of specifically hybridizing with the desired nucleic acid sequences.

The kits can include components for isolating and/or detecting RNA in essentially any sample (e.g., urine, blood, etc.), and a wide variety of reagents and methods are, in view of this specification, known in the art. Hence, the kits can include vials, swabs, needles, syringes, labels, pens, pencils, or combinations thereof.

Commercially available components can also be included in the kits.

For example, the kit can include components from QIAGEN, which manufactures a number of components for RNA isolation, including RNEASY, a Total RNA System (involving binding total RNA to a silica-gel-based membrane and spinning the RNA); OLIGOTEX® for isolation of RNA utilizing spherical latex particles; and QIAGEN total RNA kit for In Vitro Transcripts and RNA clean-up.

The kits can include components for fluorescence based real-time detection methods. For example, the kits can include primers for generating cDNA and/or for amplification of mRNA and rRNA. The kits can include components for 5' nuclease assays employ oligonucleotide probes labeled with at least one fluorescer and at least one quencher. Prior to cleavage of the probe, the fluorescer excites the quencher(s) rather than producing a detectable fluorescence emission. The oligonucleotide probe hybridizes to a target oligonucleotide sequence for amplification in PCR. The nuclease activity of the polymerase used to catalyze the amplification of the primers of the target sequence serves to cleave the probe, thereby causing at least one fluorescer to be spatially separated from the quencher so that the signal from the fluorescer is no longer quenched. A change in fluorescence of the fluorescer and/or a change in fluorescence of the quencher due to the oligonucleotide probe being digested can be used to indicate the amplification of the target oligonucleotide sequence. Although some primers and probes are described in Table 1, other suitable primers and probes can be employed. Probes and primers can be designed using techniques available to those of skill in the art.

The kits can also include any of the following components: materials for obtaining a sample, enzymes, buffers, probes, primers for generating cDNA, primers for amplifying RNA or cDNA, materials for labeling nucleic acids, microarrays, one or more microarray reader, competitor nucleic acids, probes and/or primers for a housekeeping gene for normalization, control nucleic acids, and antibodies.

In further embodiments, kits can include a urine collection system. Urine collection systems can include essentially any material useful for obtaining and/or holding a urine sample. Urine collection systems may include, for example, tubing, a beaker, a flask, a vial, a test tube, a container, and/or a lid for a vial, test tube or container (e.g., a plastic container with a snap-on or screw top lid).

In certain embodiments, kits can also include sample test system. A sample test system can include essentially any material that is useful for containing the sample and contacting the sample with the appropriate detection reagents. In some instances, the sample test system can include purification chambers and purification reagents. A sample test system can include, for example, a sample well, which may be part of a multi-well plate, a petri dish, a filter (e.g., paper, nylon, nitrocellulose, PVDF, cellulose, silica, phosphocellulose, or other solid or fibrous surface), a microchannel (which may be part of a microchannel array or a microfluidics device), a small tube such as a thin-walled PCR tube or a 1.5 ml plastic tube, a microarray to which urine, urinary cells, or material obtained from urine may be applied, a capillary tube or a flat or curved surface with detection reagent adhered thereto, or a flat or curved surface with material that adheres to proteins or nucleic acids present in the urine sample or in the urinary cells.

Kits can include probes that may be affixed to a solid surface to form a customized array. The probes can be any probe that can hybridize to any of the nucleic acids described herein. In some instances, the probes hybridize under medium to high stringency conditions.

Kits may also include a sample preparation system. A sample preparation system comprises, generally, any materials or substances that are useful in preparing the urine sample to be contacted with the detection reagents. For example, a sample preparation system may include materials for separating urine sediments from the fluids, such as centrifuge tube, a microcentrifuge, or a filter (optionally fitted to a tube designed to permit a pressure gradient to be established across the filter). One example of a filter that can be used is a filter within a syringe, such as those available from Zymo Research (see website at zymoresearch.com/columns-plastics/column-filter-assemblies/zrc-gf-filter; e.g., ZRC-GF Filter™). Other components that can be included in the kit include buffers, precipitating agents for precipitating either wanted or unwanted materials, chelators, cell lysis reagents, RNase inhibitors etc.

Collection, presentation and preparation systems can accomplished in various ways. For example, a filter can be used to separate urine sediments (e.g., cells) from the urinary fluids, and the filter may be coated with antibodies suitable for specifically detecting the desired proteins. One of skill in the art would, in view of this specification, readily understand many combinations of components that a kit of the invention may comprise.

Definitions

An "anti-rejection agent" is any substance administered to a subject for the purpose of preventing or ameliorating a rejection state. Anti-rejection agents include, but are not limited to, azathioprine, cyclosporine, FK506, tacrolimus, mycophenolate mofetil, anti-CD25 antibody, antithymocyte globulin, rapamycin, ACE inhibitors, perillyl alcohol, anti-CTLA4 antibody, anti-CD40L antibody, anti-thrombin III, tissue plasminogen activator, antioxidants, anti-CD 154, anti-CD3 antibody, thymoglobin, OKT3, corticosteroid, or a combination thereof.

"Baseline therapeutic regimen" is understood to include those anti-rejection agents being administered at a baseline time, subsequent to the transplant. The baseline therapeutic regimen may be modified by the temporary or long-term addition of other anti-rejection agents, or by a temporary or long-term increase or decrease in the dose of one, or all, of the baseline anti-rejection agents.

The term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. Biopsies also include a fine needle aspiration biopsy, a minicore needle biopsy, and/or a conventional percutaneous core needle biopsy.

A "sample" includes fluid samples obtained from a subject. A sample contains cells, proteins, nucleic acids or other cellular matter. A sample may also be the liquid phase of a body fluid from which sedimentary materials have been substantially removed. Exemplary samples include, but are not limited to, blood samples containing peripheral blood mononuclear cells (PBMCs), urine samples containing urinary cells, urine "supernatant" that is substantially free of cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. For example, the sample can be a urinary cell sample. A "post-transplantation sample" refers to a sample obtained from a subject after the transplantation has been performed.

"Baseline level of gene expression level" includes the particular gene expression level of a healthy subject or a subject with a well-functioning transplant. The baseline level of gene expression includes the gene expression level of a subject without acute rejection. The baseline level of gene expression can be a number on paper or the baseline level of gene expression from a control sample of a healthy subject or a subject with a well-functioning transplant.

The term "determining" is used herein to mean testing, assaying, and/or physically manipulating a sample to ascertain what the sample contains. In some cases, "determining" can also include quantifying a component of a sample.

As used herein, "identifying increased expression of an RNA" includes measurement of a signal from a assay that quantifies the amount of RNA in a sample subjected to the assay.

The term "up-regulation," "up-regulated," "increased expression," "higher expression," and "higher levels of expression" are used interchangeably herein and refer to the increase or elevation in the amount of a target RNA. "Up-regulation," "up-regulated," "increased expression," "higher expression," and "increased levels of expression" mean detection of expression that is greater than a baseline level (e.g., a control, or reference) of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or higher. In some instances, the "up-regulation," "up-regulated," "increased expression," "higher expression," and "higher levels of expression" mean detection of expression that is greater than a baseline level by 2-fold, 3-fold, 5-fold, 7-fold, 8-fold, 9-fold, 10-fold, or more. "Increased expression," "up-regulation," "up-regulated," "higher expression," and "higher levels of expression" can also mean detection of expression with a six-signature of greater than about 0.3, or greater than about 0.4, or greater than about 0.5, or greater than about 0.6, or greater than about 0.7, or greater than about 0.8, or greater than about 0.9, or greater than 1.0.

The term "diagnosis" is used herein to refer to the identification or classification of a molecular or pathological state, disease or condition. For example, "diagnosis" may refer to identification of a particular type of acute rejection, e.g., acute cellular rejection.

The term "aiding diagnosis" is used herein to refer to methods that assist in making a clinical determination regarding the presence, degree or other nature, of a particular type of symptom or condition of acute rejection.

The term "prediction" or "predicting" is used herein to refer to the likelihood that a patient will develop acute rejection. Thus, prediction also includes the time period without acute rejection.

A "probe or primer" as used herein refers to a group of nucleic acids where one or more of the nucleic acids can be used to detect one or more genes (e.g., CD3ε mRNA, CD105 mRNA, TLR4 mRNA, CD14 mRNA, complement factor B mRNA, vimentin mRNA, CD46 mRNA, or 18S rRNA). Detection may be, for example, through amplification as in PCR, QPCR, RT-PCR, or primer extension. Detection can also be through hybridization, or through selective destruction and protection, as in assays based on the selective enzymatic degradation of single or double stranded nucleic acids, or by detecting RNA affixed to a solid surface (e.g., a blot). Probes and/or primers may be labeled with one or more fluorescent labels, radioactive labels, fluorescent quenchers, enzymatic labels, or other detectable moieties. Probes may be any size so long as the probe is sufficiently large to selectively detect the desired nucleic acid or to serve as a primer for amplification.

Primers can be polynucleotides or oligonucleotides capable of being extended in a primer extension reaction at their 3' end. In order for an oligonucleotide to serve as a primer, it typically needs only be sufficiently complementary in sequence to be capable of forming a double-stranded structure with the template, or target, under the conditions employed. Establishing such conditions typically involves selection of solvent and salt concentration, incubation temperatures, incubation times, assay reagents and stabilization factors known to those in the art. The term primer or primer oligonucleotide refers to an oligonucleotide as defined herein, which is capable of acting as a point of initiation of synthesis when employed under conditions in which synthesis of a primer extension product that is complementary to a nucleic acid strand is induced, as, for example, in a DNA replication reaction such as a PCR reaction. Like non-primer oligonucleotides, primer oligonucleotides may be labeled according to any technique known in the art, such as with radioactive atoms, fluorescent labels, enzymatic labels, proteins, haptens, antibodies, sequence tags, mass label or the like. Such labels may be employed by associating them, for example, with the 5' terminus of a primer by a plurality of techniques known in the art. Such labels may also act as capture moieties. A probe or primer may be in solution, as would be typical for multiplex PCR, or a probe or primer may be adhered to a solid surface, as in an array or microarray. It is well known that compounds such as PNAs may be used instead of nucleic acids to hybridize to genes. In addition, probes may contain rare or unnatural nucleic acids such as inosine.

As used herein, the term polynucleotide or nucleic acid includes nucleotide polymers of any number. The term polynucleotide can, for example, have less than about 200 nucleotides. However, other polynucleotides can have more than 200 nucleotides. Probes and primers are polynucleotides. Primers can, for example, have between 5 and 100 nucleotides, or have about 15 to 100 nucleotides. Probes can have the same or longer lengths. For example, probes can have about 16 nucleotides to about 10,000 nucleotides. The exact length of a particular polynucleotide depends on many factors, which in turn depend on its ultimate function or use. Some factors affecting the length of a polynucleotide are, for example, the sequence of the polynucleotide, the assay conditions in terms of such variables as salt concentrations and temperatures used during the assay, and whether or not the polynucleotide is modified at the 5' terminus to include additional bases for the purposes of modifying the mass:charge ratio of the polynucleotide, or providing a tag capture sequence which may be used to geographically separate a polynucleotide to a specific hybridization location on a DNA chip, for example.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "recipient" (or "host"). An organ, or graft, transplanted between two genetically different individuals of the same species is called an "allograft." A graft transplanted between individuals of different species can be referred to as a "xenograft."

As used herein, "transplant rejection" refers to a functional and structural deterioration of the organ due to an active immune response expressed by the recipient, and independent of non-immunologic causes of organ dysfunction. Acute transplant rejection can result from the activation of recipient's T cells and/or B cells; the rejection primarily due to T cells is classified as T cell mediated acute rejection or acute cellular rejection (ACR) and the rejection in which B cells are primarily responsible is classified as antibody mediated acute rejection (AMR). In some embodiments, the methods and compositions provided can detect and/or predict acute cellular rejection.

As used herein, "subject" means a mammal. "Mammals" means any member of the class of Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; or the like. The term "subject" does not denote a particular age or sex. Preferably the subject is a human patient. In some instances, the subject is a human who has received an organ transplant.

The term "up-regulation," "up-regulated," "increased expression," "higher expression," and "higher levels of expression" are used interchangeably herein and refer to the increase or elevation in the amount of a target RNA. "Up-regulation," "up-regulated," "increased expression," "higher expression," and "increased levels of expression" include increases above a baseline (e.g., a control, or reference) level of 10%, 15%, 20%, 25%, 30%, 35%, 40%, 45%, 50%, 55%, 60%, 65%, 70%, 75%, 80%, 85%, 90%, 95%, 100% or higher. "Increased expression" can also mean detection of expression with a six-signature of greater than about −0.24, or greater than about −0.2, or greater than about −0.1, or greater than about 0.0, or greater than about 0.1, or greater than about 0.2, or greater than about 0.3, or greater than about 0.4.

The term "hybridization" includes a reaction in which one or more nucleic acids or polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two single strands forming a duplex structure, three or more strands forming a multi-stranded complex, a single self-hybridizing strand, or any combination of these. A hybridization reaction may constitute a step in a more extensive process, such as the initiation of a PCR reaction, primer extension reaction, or the enzymatic cleavage of a polynucleotide by a ribozyme.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C. When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide if hybridization can occur between one of the strands of the first polynucleotide and the second polynucleotide. "Complementarity" or "homology" is quantifiable in terms of the proportion of bases in opposing strands that are expected to hydrogen bond with each other, according to generally accepted base-pairing rules.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); Nucleic Acid Hybridization, A Practical Approach, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed. In general, the stringency of hybridization is determined by the wash step. Hence, a wash step involving 0.1×SSPE, 1.0% SDS at a temperature of at least 42° C. can yield a high stringency hybridization product. In some instances the high stringency hybridization conditions include a wash in 1×SSPE, 1.0% SDS at a temperature of at least 50° C., or at about 65° C.

"Medium stringency conditions" when used in reference to nucleic acid hybridization include conditions equivalent to binding or hybridization at 42☐° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed. Hence, a wash step involving 1.0×SSPE, 1.0% SDS at a temperature of 42° C. can yield a medium stringency hybridization product.

"Low stringency conditions" include conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed. Hence, a wash step involving 5×SSPE, 1.0% SDS at a temperature of 42° C. can yield low stringency hybridization product.

A "gene product" includes a peptide, polypeptide, or structural RNA generated when a gene is transcribed and/or translated. While an mRNA encoding a peptide or polypeptide can be translated to generate the peptide or polypeptide, a structural RNA (e.g., an rRNA) is not translated. In some embodiments, the target gene expresses CD3ε mRNA, CD105 mRNA, TLR4 mRNA, CD14 mRNA, complement factor B mRNA, vimentin mRNA, CD46 mRNA, or 18S rRNA.

The term "level of gene expression" as used herein refers to quantifying gene expression. In some embodiments, to accurately assess whether increased mRNA or rRNA is significant, the measured expression is "normalized" against a selected normalizer. Normalization of gene expression can allow more accurate comparison of levels of expression between samples. Quantification of gene expression can be accomplished by methods known in the art, such as, for example, reverse transcription polymerase chain reaction (RT-PCR), TAQMAN® assays or the like. Gene expression can also be quantified by detecting a protein, peptide or structural RNA gene product directly, in a variety of assay formats known to those of ordinary skill in the art. For example, proteins and peptides can be detected by an assay such as an enzyme linked immunosorbant assay (ELISA), radioimmunoassay (RIA), immunofluorimetry, immunoprecipitation, equilibrium dialysis, immunodiffusion, immunoblotting, mass spectrometry and other techniques. See, e.g., Harlow and Lane, Antibodies: A Laboratory Manual, Cold Spring Harbor Laboratory, 1 88; Weir, D. M., Handbook of Experimental Immunology, 1986, Blackwell Scientific, Boston.

As used herein, the term "biomarker" includes a polynucleotide or polypeptide molecule which is present or increased in quantity or activity in subjects having acute rejection or where the acute rejection is anticipated.

As used herein, the term "panel of biomarkers" includes a group of markers, the quantity or activity of each member of which is correlated with subjects having acute rejection or where the acute rejection is anticipated. In certain embodiments, a panel of markers may include only those markers which are either increased in quantity or activity in those subjects. In some embodiments, the panel of markers include one, two, three, four, five, six, seven, or eight, of CD3ε mRNA, CD105 mRNA, TLR4 mRNA, CD14 mRNA, complement factor B mRNA, vimentin mRNA, CD46 mRNA, and 18S rRNA. For example, the panel can include RNAs from the following genes: CD3ε, CD105, TLR4, CD14, complement factor B, and vimentin (e.g., to detect acute rejection of a transplant). A panel can also include RNAs from the following genes: CD3ε, CD105, CD14, CD46 and 18S rRNA (e.g., to distinguish acute cellular rejection (ACR) from antibody-mediated rejection (AMR)).

The present description is further illustrated by the following examples, which should not be construed as limiting in any way.

EXAMPLE 1

Materials and Methods

This Example describes some of the materials and methods employed in developing the invention.

Study Cohorts

Absolute levels of 26 mRNAs and 18S rRNA in 84 urine samples from 84 kidney transplant recipients were measured. All recipients provided written informed consent to participate in the study and the Institutional Review Board approved the study. The clinical and research activities that reported are consistent with the Principles of the Declaration of Istanbul as outlined in the "Declaration of Istanbul on Organ Trafficking and Transplant Tourism." A single pathologist with no prior information about the urinary cell gene expression results evaluated the biopsy specimens and categorized them using the Banff '07 update of the Banff '97 classification (Solez et al., *Am J Transplant* 8: 753-760 (2008).

There were 26 ACR biopsies (interstitial inflammation and tubulitis with minimal microcirculatory inflammation and absence of peritubular capillary C4d staining) from 26 patients, 26 AMR biopsies (microcirculatory inflammation and presence of C4d staining with minimal interstitial inflammation and tubulitis) from 26 patients, and 32 ATI biopsies (attenuation or loss of brush border or necrosis and sloughing of tubular epithelium with or without isometric vacuolization and no interstitial inflammation, tubulitis, or microcirculatory inflammation and absence of C4d staining) from 32 patients.

Among the 26 patients with AMR, 22 had results available, and were positive, for circulating anti-HLA donor specific antibodies. The remaining 4 patients did not have results available for circulating anti-HLA donor specific antibodies and hence should be categorized as suspicious for AMR based on Banff classification (Solez et al., *Am J Transplant* 8: 753-760 (2008).

Quantification of mRNAs

Approximately 50 ml of urine was obtained at the time of allograft biopsy. Urine was centrifuged at 1250 g for 30 minutes at room temperature within 4 hours of collection. Total RNA was isolated from urinary cells using the RNeasy mini kit (Qiagen, Valencia, Calif.). The quantity (absorbance at 260 nm) and purity (ratio of the absorbance at 260 nm and 280 nm) of the RNA isolated from the urine cell pellet was measured using the NanoDrop® ND-1000 spectrophotometer (Thermo Scientific). The RNA was reverse transcribed to complementary DNA using TaqMan Reverse Transcription Reagents (Applied Biosystems) at a final concentration of 1.0 µg of total RNA in 100 µl volume. Gene-specific oligonucleotide primers and flurogenic probes were designed using Primer Express software (Applied Biosystems, Foster City, Calif.), for the measurement of 26 mRNAs and a housekeeping/reference gene, 18S rRNA. Sequences for some of the designed primers and probes are listed in Table 1.

TABLE 1

Oligonucleotide Primers and Probes

| mRNA | Accession No. | Sequence | Location | SEQ ID NO: |
|---|---|---|---|---|
| CD3ε | NM_000733 | Sense: 5'-AAGAAATGGGTGGTA TTACACAGACA-3'; SEQ ID NO:10 | 131-156 | SEQ ID NO: 10 |
| | | Antisense: 5'-TGCCATAGT-ATTTCA GATCCAGGAT-3'; SEQ ID NO:11 | 233-209 | SEQ ID NO: 11 |
| | | Probe: 5'-FAM-CCATCTCTGGAAC CACAGTAATATTGACATGCC-TAMRA-3'; SEQ ID NO:12 | 170-202 | SEQ ID NO: 12 |
| Granzyme B | J04071 | Sense: 5'-GCGAATCTGACTTACGCC ATTATT-3'; SEQ ID NO:13 | 534-557 | SEQ ID NO: 13 |
| | | Antisense: 5'-CAAGAGGGCCTC-CAG AGTCC-3'; SEQ ID NO:14 | 638-619 | SEQ ID NO: 14 |
| | | Probe: 5'-FAM-CCCACGCACAACTC AATGGTACTGTCG-TAMRA-3' SEQ ID NO:15 | 559-585 | SEQ ID NO: 15 |
| Perforin | M28393 | Sense: 5'-GGACCAGTACAGCTTCA GCACTG-3'; SEQ ID NO:16 | 492-514 | SEQ ID NO: 16 |
| | | Antisense: 5'-GCCCTCTT-GAAGTCA GGGTG-3'; SEQ ID NO:17 | 587-568 | SEQ ID NO: 17 |
| | | Probe: 5'-FAM-TGCCGCTTCTACAG TTTCCATGTGGTACAC-TAMRA-3'; SEQ ID NO:18 | 526-555 | SEQ ID NO: 18 |
| FoxP3 | NM_014009 | Sense 5'-GAGAAGCTGAGTGCC ATGCA-3'; SEQ ID NO:19 | 939-958 | SEQ ID NO: 19 |
| | | Antisense 5-GGAGCCCTTGTCGG ATGAT-3'; SEQ ID NO:20 | 1025-1007 | SEQ ID NO: 20 |
| | | Probe 5'-FAM-TGCCATTTTCCCAG CCAGGTGG-TAMRA-3'; SEQ ID NO:21 | 962-983 | SEQ ID NO: 21 |
| OX40 | NM_003327.2 | Sense: 5'-ACGACGTGGTCAG CTCCAA-3'; SEQ ID NO:22 | 223-241 | SEQ ID NO: 22 |
| | | Antisense: 5'-TCCGCTCACTC CCACTTCTG-3'; SEQ ID NO:23 | 291-272 | SEQ ID NO: 23 |
| | | Probe: 5'-FAM-AAGCCCTGC ACGTGG-MGB-3'; SEQ ID NO:24 | 249-263 | SEQ ID NO: 24 |
| CD105 | NM_000118.2 | Sense: 5'-CAGCCTCAGCCCC ACAAGT-3'; SEQ ID NO:25 | 464-482 | SEQ ID NO: 25 |

TABLE 1-continued

Oligonucleotide Primers and Probes

| mRNA | Accession No. | Sequence | Location | SEQ ID NO: |
|---|---|---|---|---|
| | | Antisense: 5-GGCCCACAGGC TGAAGGT-3'; SEQ ID NO:26 | 522-505 | SEQ ID NO: 26 |
| | | Probe: 5'-FAM-TTGCAGAAA CAGTCCATT-MGB-3'; SEQ ID NO:27 | 484-501 | SEQ ID NO: 27 |
| CD146 | NM_006500.2 | Sense: 5'-CCTGGA CTTGGACA CCATGAT-3'; SEQ ID NO:28 | 995-1015 | SEQ ID NO: 28 |
| | | Antisense: 5'-ACTCGGACGTCA GACACATAGTTC 3'; SEQ ID NO: 29 | 1049-1072 | SEQ ID NO: 29 |
| | | Probe: 5'-FAM-TGCTGAGTGA ACCACAGG-MGB 3'; SEQ ID NO: 30 | 1021-1038 | SEQ ID NO: 30 |
| von Willebrand Factor | X04385.1 | Sense: 5'-CCTCAAAGGCGGT GGTCAT-3'; SEQ ID NO:31 | 5474-5492 | SEQ ID NO: 31 |
| | | Antisense: 5'-AGCGATCTCCA ATTCCAATAGG-3'; SEQ ID NO:32 | 5590-5569 | SEQ ID NO: 32 |
| | | Probe: 5'-FAM-CCAACAGAG TGACAGTGT-MGB-3'; SEQ ID NO:33 | 5549-5566 | SEQ ID NO: 33 |
| Iummuno-globulin J | NM_144646.3 | Sense: 5'-TGGAGAGAAACAT CCGAATTATTG- 3'; SEQ ID NO:34 | 308-331 | SEQ ID NO: 34 |
| | | Antisense: 5'-TGGTGAGGTGG GATCAGAGATA-3'; SEQ ID NO:35 | 375-354 | SEQ ID NO: 35 |
| | | Probe: 5'-FAM-TCCTCTGAAC AACAGGGA-MGB-3'; SEQ ID NO:36 | 333-350 | SEQ ID NO: 36 |
| PSMB10 | NM_002801.3 | Sense: 5'-AGAGCTGCGAGAA GATCCACTT-3'; SEQ ID NO:37 | 331-352 | SEQ ID NO: 37 |
| | | Antisense: 5'-CTCCAGCCCCA CAGCAGTA-3'; SEQ ID NO:38 | 388-369 | SEQ ID NO: 38 |
| | | Probe: 5'-FAM-ATCGCCCCC AAAAT-MGB-3'; SEQ ID NO:39 | 354-367 | SEQ ID NO: 39 |
| TRIBS-1 | BC063292.1 | Sense: 5'-GGGCGCTGTGCA TCCA-3'; SEQ ID NO:40 | 902-917 | SEQ ID NO: 40 |
| | | Antisense: 5-AAGGCCTGATT TTGTCCTGGTA-3'; SEQ ID NO:41 | 982-961 | SEQ ID NO: 41 |
| | | Probe: 5'-FAM-CGCTGCAAG GTGTTT-MGB-3'; SEQ ID NO:42 | 934-948 | SEQ ID NO: 42 |
| TLR-4 | NM_138554.1 | Sense: 5'-CATGGCCTTCCTCT CCTGC-3'; SEQ ID NO:43 | 209-227 | SEQ ID NO: 43 |
| | | Antisense: 5'-GAAATTCAGCT CCATGCATTGA-3'; SEQ ID NO:44 | 302-281 | SEQ ID NO: 44 |
| | | Probe: 5'-FAM-AGGAACCACCT CCACGCAGGGCT- TAMRA-3'; SEQ ID NO:45 | 269-247 | SEQ ID NO: 45 |

TABLE 1-continued

Oligonucleotide Primers and Probes

| mRNA | Accession No. | Sequence | Location | SEQ ID NO: |
|---|---|---|---|---|
| CD14 | NM_000591 | Sense: 5'-GCTGTGTAGAAAGAA GCTAAAGCACTT-3'; SEQ ID NO:46 | 51-77 | SEQ ID NO: 46 |
| | | Antisense: 5'-TGGCGTGGTCGCA GAGA-3'; SEQ ID NO:47 | 185-169 | SEQ ID NO: 47 |
| | | Probe: 5'-FAM-CTTATCGACCAT GGAGCGCGCGT TAMRA 3'; SEQ ID NO:48 | 110-132 | SEQ ID NO: 48 |
| C3 | NM_000064.2 | Sense: 5'-CAGCACCGGAAACAG AAAAGAG-3'; SEQ ID NO:49 | 4168-4189 | SEQ ID NO: 49 |
| | | Antisense: 5'-CCCCGGTACCTG GTACAGATC-3'; SEQ ID NO:50 | 4243-4143 | SEQ ID NO: 50 |
| | | Probe: 5'-FAM-AAGAACACTA TGATCCTTG-MGB-3'; SEQ ID NO:51 | 4203-4221 | SEQ ID NO: 51 |
| C5 | NM_001735.2 | Sense: 5'-TTCCTTGGGAGGCC AGTAGA-3'; SEQ ID NO:52 | 4027-4046 | SEQ ID NO: 52 |
| | | Antisense: 5'-AGCCAAGCCAC TGCCAAA-3'; SEQ ID NO:53 | 4101-4082 | SEQ ID NO: 53 |
| | | Probe: 5'-FAM-ACCTCATTGTC AGTACAGG-MGB-3'; SEQ ID NO:54 | 4084 4064- | SEQ ID NO: 54 |

The mechanistically informative panel of 26 mRNAs was designed based on the inventors' single center experience and as informed from the literature. The probes were labeled with 6-carboxy-fluorescein (FAM) at the 5' end and 6-carboxy-tetramethylrodamine (TAMRA) or dihydrocyclopyrroloindole tripeptide minor groove binder (MGB) at the 3' end. FAM functioned as the reporter dye and TAMRA or MGB as the quencher dye. A two-step PCR assay was performed with a preamplification step (Muthukumar et al., N Engl J Med 353: 2342-2351 (2005)) followed by measurement of the absolute levels of mRNAs, using the inventors' previously described standard curve method (Suthanthiran et al., N Engl J Med 369: 20-31 (2013)) in an ABI Prism 7500HT Fast detection system. The values of mRNAs and the 18S rRNA were expressed as copies per microgram of total RNA. The standard curve copy numbers in our PCR assays ranged from 25 to 2.5 million copies, and for data analysis, mRNA copy numbers greater than 25 were scored as 12.5 copies per microgram of total RNA. In each of the 84 specimens, an 18S rRNA value of greater than $5 \times 10^7$ copies/microgram total RNA and a TGFβ1 mRNA value of greater than $1 \times 10^2$ copies/ug total RNA were used as a measure of transcript adequacy in that specimen (Suthanthiran et al., N Engl J Med 369: 20-31 (2013)).

Three patients (2 in the AMR biopsies group and 1 in the ATI biopsy group) had BK virus replication in the urine, defined as greater than or equal to $10^6$ copies of BK virus VP1 mRNA per microgram of total RNA from urinary cells (Dadhania et al., Transplantation 86: 521-528 (2008)), collected at the time of allograft biopsy. These three patients however did not have BK virus nephropathy as defined by negative immunohistochemistry for renal tubular epithelial nuclear SV40 large T antigen.

Statistical Analysis

The levels of urinary cell transcripts were natural logarithm (ln) transformed to reduce the deviation from normality. The levels of transcripts in the three diagnostic categories; ACR, AMR and ATI were compared, using the Kruskal-Wallis test followed by Dunn's post-test.

A two-step approach was used to develop the diagnostic signatures. In both steps, the AUC was first calculated for each mRNA quantity measured to differentiate the two diagnostic categories, AR vs. ATI and ACR vs. AMR. Quadratic discriminant function analysis was then used to develop a linear combination of variables that best predicted the diagnostic category (Hair et al. (Eds.) Multivariate Analysis, Upper Saddle river, New Jersey, Prentice hall (1998). Twenty-five of the 26 mRNAs measured and 18S rRNA were used as independent variables. Discriminant analysis measures the distance from each point in the data to each group's multivariate mean and calculates a posterior probability of group membership. The analysis also takes into account the prior probability of group membership for calculating the posterior probability.

To mimic the approximate prevalence of AR and ATI in consecutive biopsies done for acute allograft dysfunction, for step-1, a prior probability of 0.6 for AR and 0.4 for ATI was assigned. For the same reason, in step-2, a prior probability of 0.65 for ACR and 0.35 for AMR was assigned. A step-wise backward estimation was used; all 25 mRNAs and 18SrRNA were entered in the model and were removed one at a time on the basis of their discriminating power. At $P<0.05$, no further variables were removed and the existing variables were considered as the final parsimonious model. The linear combination of variables yielded a discriminant score that constituted the diagnostic signature.

The inventors tested whether the signature better predicted the diagnostic outcome than individual mRNAs using the likelihood ratio test. A 10-fold cross validation was used to internally validate the diagnostic signatures. The entire cohort was randomly divided into ten equal groups. Within each of the ten groups, the proportion of samples was similar to the undivided cohort. At the first run, group 1 was excluded and the signature was derived from the remaining 9 groups (90% of samples) including both variables selection and model fitting. Next, this newly derived signature was applied to samples of group 1 (10% of samples) to predict their diagnostic outcome. In the second run, group 2 was excluded and the signature was derived from the remaining 9 groups (90% of samples) including both variables selection and model fitting. This newly derived signature was applied to samples of group 2 (10% of samples) to predict their diagnostic outcome. This iteration was done for all the 10 groups. Thus, all observations are used for both deriving and validating a model and each observation is used for validation exactly once. Accordingly, the predicted probability for an individual patient was derived from a model that does not include any data from that patient. The predicted probability for each patient from the cross validation was then used to calculate discrimination statistics and in decision curve analysis, which quantifies the clinical benefit of the diagnostic signature in terms of the number of unnecessary biopsies that can be avoided in the diagnosis of AR. Decision curve analysis is a widely used method for evaluating predictions (Steyerberg et al., *Epidemiology* 21: 128-138 (2010); Vickers et al., *Med Decis Making* 26: 565-574 (2006); Steyerberg & Vickers, *Med Decis Making* 28: 146-149 (2008); Vickers, *Am Stat* 62: 314-320 (2008). It is a weighted sum of true and false positives, with the latter weighted by the odds at the threshold probability for biopsy, a value that can be modified to reflect different preferences about the harms of unnecessary biopsies compared to that of delayed diagnosis of acute rejection. JMP 10.0.2 software (SAS Institute Inc., Cary, N.C.) was used for discriminant analysis and Stata 11.2 software (StataCorp, College Station, Tex.) for decision curve analysis.

EXAMPLE 2

Patient Characteristics

This Example describes the patient characteristics.

Absolute levels of mRNAs were measured in 84 urine samples from 84-kidney transplant recipients who had undergone a clinically indicated (for-cause) kidney allograft biopsy at our institution to determine the cause of their acute allograft dysfunction (FIG. 1A). All 84 patients had either an elevation in the level of serum creatinine from baseline or had persistently elevated serum creatinine levels that did not decrease as expected that prompted the treating physician to do a biopsy. Urine samples were collected at the time of a for-cause biopsy and prior to the initiation of any specific treatment. Among the 84 biopsy matched urine samples, 52 were from patients with biopsies showing acute rejection (26 ACR and 26 AMR), and 32 were from patients with biopsies showing ATI without acute rejection (AR; Table 1). Biopsy-matched urine specimens were selected at a ratio of 3:2 for AR:ATI and 1:1 for ACR:AMR. The 3:2 ratio is an approximation of the expected proportions of the biopsy diagnosis in consecutive biopsies performed for suspected acute rejection. A 1:1 ratio of ACR to AMR was used to develop robust biomarkers for distinguishing these two major subtypes of AR. Urine from patients with less frequent findings such as BK virus nephropathy or allergic interstitial nephritis were not included. As illustrated in FIG. 1A, a two-step approach was used to develop the diagnostic signatures for the differential diagnosis of acute graft dysfunction. First, AR (both types, N=52) was differentiated from ATI (N=32) with the use of urinary cell mRNA levels. Thereafter, ACR (N=26) was differentiated from AMR (N=26) using the same assay results.

Urine volume and the quantity and purity of total RNA isolated from the urinary cells did not vary across the three diagnostic categories (Table 2).

TABLE 2

Characteristics of Kidney Allograft Recipients

| Variables | Acute T-cell Mediated Rejection | Acute Antibody-Mediated Rejection | Acute Tubular Injury | P$^a$ value |
|---|---|---|---|---|
| Kidney allograft recipients, N | 26 | 26 | 32 | — |
| Urine specimens, N | 26 | 26 | 32 | — |
| At the time of transplant | | | | |
| Age, years, mean (SD) | 49 (14) | 47 (13) | 51 (15) | 0.5 |
| Gender, female, N (%) | 8 (31) | 11 (42) | 13 (41) | 0.6 |
| Racial categories, black/other categories, N (%) | 11/15 (42/58) | 8/18 (31/69) | 9/23 (28/72) | 0.5 |
| Cause of end-stage kidney disease, N (%) | | | | |
| Diabetes mellitus | 7 (27) | 4 (15) | 6 (19) | 0.9 |
| Hypertension | 6 (23) | 7 (27) | 8 (24) | |
| Glomerulonephritis | 3 (12) | 5 (20) | 6 (19) | |
| Others | 6 (23) | 4 (15) | 6 (19) | |
| Unknown | 4 (15) | 6 (23) | 6 (19) | |
| Donor information | | | | |
| Age, years, mean (SD) | 43 (21) | 45 (13) | 53 (11) | 0.1 |
| Gender, female, N (%) | 15 (68) | 10 (45) | 12 (44) | 0.2 |
| Racial categories, black/other categories, N (%) | 4/22 (15/85) | 8/18 (31/69) | 5/27 (16/84) | 0.5 |

TABLE 2-continued

Characteristics of Kidney Allograft Recipients

| Variables | Acute T-cell Mediated Rejection | Acute Antibody-Mediated Rejection | Acute Tubular Injury | P[a] value |
|---|---|---|---|---|
| Deceased donor organ, N (%) | 10 (38) | 14 (54) | 19 (59) | 0.3 |
| Human leukocyte antigen mismatches, mean (SD) | 4 (1.2) | 5 (1.6) | 4 (1.8) | 0.1 |
| Cold ischemia time (deceased donors), hours, median (interquartile range) | 21 (12-29) | 24 (12-26) | 28 (18-33) | 0.5 |
| Induction therapy | | | | |
| Lymphocyte depleting-Thymoglobulin ®, N (%) | 16 (62) | 16 (62) | 27[b] (84) | 0.02[c] |
| Lymphocyte non-depleting-Interleukin-2 receptor antibody, N (%) | 4 (15) | 8 (30) | 5 (16) | 0.01[d] |
| None, N (%) | 6 (23) | 2 (8) | 0 (0) | |
| After transplant and prior to the index allograft biopsy | | | | |
| Delayed graft function, N (%) | 8 (31) | 5 (19) | 19 (59) | 0.01 |
| Maintenance immunosuppression | | | | |
| Tacrolimus, N (%) | 26 (100) | 26 (100) | 32 (100) | — |
| Mycophenolate, N (%) | 26 (100) | 26 (100) | 32 (100) | — |
| Corticosteroids, N (%) | 16 (62) | 17 (65) | 7 (22) | 0.001 |
| Acute rejection, N (%) | 2 (8) | 2 (8) | 0 (0) | — |
| Bacterial urinary tract infections[e], N (%) | 9 (35) | 8 (31) | 5 (16) | 0.2 |
| BK virus nephropathy, N (%) | 0 (0) | 1 (4) | 0 (0) | — |
| Cytomegalovirus disease, N (%) | 0 (0) | 0 (0) | 0 (0) | — |
| At the time of the index allograft biopsy[f] | | | | |
| Time from transplantation to biopsy, months, median (interquartile range) | 4.4 (0.6-10.5) | 16.2 (0.5-34.4) | 1.2 (0.6-2.8) | 0.03[g] |
| Biopsy within 1 month of transplantation, N (%) | 10 (39) | 9 (35) | 12 (38) | <0.001 |
| Biopsy between 1 month and 12 months of transplantation, N (%) | 10 (39) | 3 (12) | 18 (56) | |
| Biopsy beyond 12 months of transplantation, N (%) | 6 (23) | 14 (54) | 2 (6) | |
| Indication for biopsy, creatinine increase/delayed graft function, N (%) | 25/1 (96/4) | 23/3 (88/12) | 24/8 (75/25) | 0.1 |
| Serum creatinine, mg/dl, median (interquartile range) | 3.20 (1.90-4.33) | 2.62 (2.01-4.29) | 3.10 (2.46-5.12) | 0.3 |
| Urine protein to creatinine ratio, median (inter quartile range) | 0.56 (0.3-2.4) | 1.03 (0.4-2.9) | 0.31 (0-2-0.9) | 0.1 |
| Serum tacrolimus trough, ng/ml, median (interquartile range) | 5.2 (4.6-8.7) | 6.5 (4.4-8.9) | 9.3 (7.8-10.4) | <0.0001[h] |
| Biopsy information | | | | |
| Acute antibody-mediated rejection, I/II/III[i] | — | 1/25/0 | — | — |
| Acute T-cell-mediated rejection, IA/IB/IIA/IIB/III[i] | 5/15/4/2/0 | — | — | — |
| Acute tubular injury, focal necrosis/isometric vacuolization, N (%) | — | — | 32 9/20 (28/63) | — |
| Positive staining for complement split product C4d, N (%) | 0 (0) | 26 (100) | 0 (0) | — |
| Concomitant interstitial fibrosis/tubular atrophy (moderate-severe), N (%) | 3 (12) | 7 (27) | 1 (3) | 0.1 |
| Antibodies to one or more donor specific Human leukocyte antigens - Data available, N (%) | 13 (50) | 22 (85) | 25 (78) | |
| Mean fluorescent intensity (MFI) of the highest rank donor specific bead <1000, N (%) | 3 (23) | 0 (0) | 17 (68) | <0.0001 |

TABLE 2-continued

Characteristics of Kidney Allograft Recipients

| Variables | Acute T-cell Mediated Rejection | Acute Antibody-Mediated Rejection | Acute Tubular Injury | P$^a$ value |
|---|---|---|---|---|
| MFI 1000-3000, N (%) | 6 (46) | 2 (9) | 4 (16) | |
| MFI 3000-10000, N (%) | 3 (23) | 10 (46) | 3 (12) | |
| MFI >10000, N (%) | 1 (8) | 10 (46) | 1 (4) | |
| Urine specimens | | | | |
| Collected on the day of biopsy, N (%) | 18 (69) | 18 (69) | 21 (66) | 0.7 |
| Collected 1-day prior/1-day after biopsy, N (%) | 3/5 (12/19) | 4/4 (15/15) | 2/9 (6/28) | |
| Urine volume, ml, median (inter quartile range) | 45 (28-70) | 43 (28-55) | 35 (25-45) | 0.1 |
| Urinary cell total RNA quantity, μg, Median (inter quartile range) | 2.1 (1.2-3.4) | 1.0 (0.6-2.5) | 1.2 (0.5-2.3) | 0.1 |
| Urinary cell total RNA purity, $OD_{260}/OD_{280}$ ratio$^j$, median (inter quartile range) | 1.97 (1.93-2.02) | 1.96 (1.91-1.99) | 1.93 (1.84-1.99) | 0.1 |

$^a$P value derived by Chi-square test for categorical variables or Kruskal-Wallis for continuous variables
$^b$Includes one patient with Alemtuzumab (Campath-1H) induction
$^c$P value based on Chi-square test of independence for 3 rows (lymphocyte depleting induction immunosuppression, lymphocyte non-depleting induction and no induction) and 3 columns (ACR, AMR and ATI).
$^d$P value based on Chi-square test of independence for 2 rows (induction immunosuppression and no induction) and 3 columns (ACR, AMR and ATI).
$^e$Defined as the presence of ≥$10^5$ colony forming units per milliliter of urine
$^f$Three patients (2 AMR and 1 ATI) had BK virus replication (≥$10^6$ copies of BK virus VP1 mRNA/microgram of total RNA from urinary cells) in the urine collected at the time of biopsy. None of the three had BK virus nephropathy (negative for SV40 staining)
$^g$P < 0.05 by Dunn's test for AMR vs. ATI
$^h$P < 0.05 by Dunn's test for ACR vs. ATI and AMR vs. ATI
$^i$Based on the Banff '09 update of the Banff 97 diagnostic categories for renal allograft biopsies
$^j$Ratio of optical density (absorbance of ultraviolet light) at 260 nm and 280 nm. Pure RNA has a ratio of ~2.

EXAMPLE 3

Patient RNA Properties

Figure 1B:
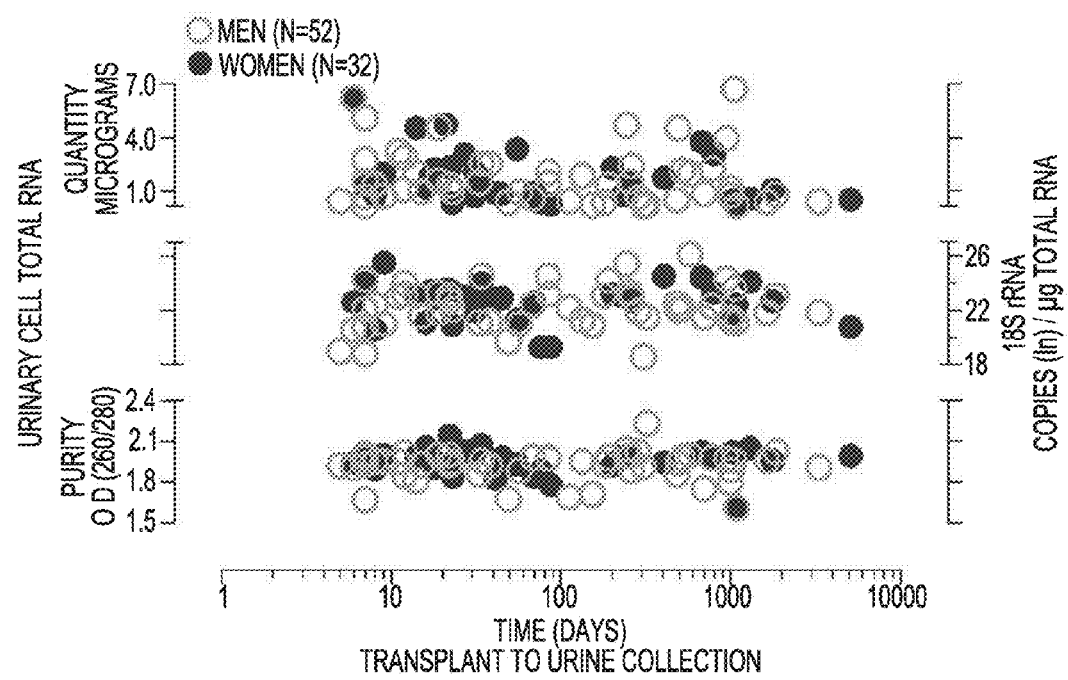

This Example describes the properties of the RNA obtained from biopsies and urine samples. The quantity and purity of total RNA and the absolute levels of housekeeping/reference gene 18S rRNA were not related to the time from transplantation to biopsy/urine collection (FIG. 1B).

Gene specific oligonucleotide primers and TaqMan probes were designed (Table 1) and used to measure absolute levels of 26 pre-specified mRNAs and 18S rRNA in urinary cells using pre-amplification enhanced real time-quantitative PCR assays (Suthanthiran et al., *N Engl J Med* 369: 20-31 (2013)). The 26-member mRNA panel was designed to be mechanistically informative and to include mRNAs encoding proteins implicated in innate as well as adaptive immunity.

Table 3 shows the median (interquartile range) absolute copy number per microgram of total RNA of all 26 mRNAs measured and the levels of 18S rRNA in the urinary cells from all 84 patients. Box plots of the levels are illustrated in FIG. 2A-2ZB.

TABLE 3

Levels of mRNA in Urinary Cells

| | | | P value | P Value (Dunn's Test) | | |
|---|---|---|---|---|---|---|
| ACR (N = 26) | AMR (N = 26) | ATI (N = 32) | (Kruskal-Wallis Test) | ACR vs. AMR | ACR vs. ATI | AMR vs. ATI |
| 27350 (15525, 96400) | 2690 (875, 8540) | 382 (108, 1415) | <0.0001 | <0.05 | <0.05 | <0.05 |
| 17400 (4105, 33950) | 2240 (708, 5610) | 444 (190, 2105) | <0.0001 | <0.05 | <0.05 | >0.05 |
| 12950 (4745, 48125) | 1920 (407, 6443) | 21 (84, 1313) | <0.0001 | <0.05 | <0.05 | <0.05 |
| 541 (371, 1080) | 119 (13, 288) | 12.5 (12.5, 12.5) | <0.0001 | <0.5 | <0.5 | <0.5 |
| 4885 (1007, 11450) | 422 (127, 2033) | 235 (12.5, 385) | <0.0001 | <0.05 | <0.05 | >0.05 |
| 32550 (13750, 55750) | 6890 (1785, 16450) | 2950 (663, 8398) | <0.0001 | <0.05 | <0.05 | >0.05 |
| 983 (630, 2923) | 573 (126, 1323) | 316 (56, 750) | <0.01 | >0.05 | <0.05 | >0.05 |
| 1245 (523, 2680) | 718 (121, 1960) | 316 (88, 1096) | <0.01 | <0.05 | <0.05 | >0.05 |

TABLE 3-continued

Levels of mRNA in Urinary Cells

| ACR (N = 26) | AMR (N = 26) | ATI (N = 32) | P value (Kruskal-Wallis Test) | ACR vs. AMR | ACR vs. ATI | AMR vs. ATI |
|---|---|---|---|---|---|---|
| 1210 (571, 4525) | 523 (149, 3660) | 72 (12.5, 192) | <0.0001 | >0.05 | <0.05 | <0.05 |
| 214500 (66525, 484500) | 28900 (9345, 58975) | 28550 (6253, 44150) | <0.0001 | <0.05 | <0.05 | >0.05 |
| 227000 (145250, 452750) | 62450 (18900, 176500) | 86200 (18750, 242500) | <0.01 | <0.05 | <0.05 | >0.05 |
| 25200 (5363, 67525) | 6800 (975, 19725) | 4140 (444, 13775) | <0.01 | <0.05 | <0.05 | >0.05 |
| 290500 (117025, 699250) | 21500 (9548, 88500) | 55950 (3083, 182250) | <0.0001 | <0.05 | <0.05 | >0.05 |
| 16700 (6028, 43550) | 6445 (1233, 13950) | 2120 (745, 8318) | <0.001 | <0.05 | <0.05 | >0.05 |
| 806 (374, 1733) | 260 (46, 535) | 97 (12.5, 390) | <0.0001 | <0.05 | <0.05 | >0.05 |
| 68500 (19600, 208500) | 8960 (3165, 47425) | 21450 (1858, 59400) | <0.01 | <0.05 | <0.05 | >0.05 |
| 31900 (14200, 58925) | 27150 (14150, 51475) | 15250 (6085, 26575) | 0.01 | >0.05 | <0.05 | >0.05 |
| 571000 (321500, 1403000) | 175500 (63075, 530000) | 173500 (44475, 891750) | <0.01 | <0.05 | <0.05 | >0.05 |
| 749500 (328000, 1438000) | 173500 (83100, 411750) | 272000 (60075, 526500) | <0.0001 | <0.05 | <0.05 | >0.05 |
| 1430000 (556000, 3810000) | 390000 (91100, 800500) | 295500 (53350, 844250) | <0.001 | <0.05 | <0.05 | >0.05 |
| 3130 (967, 7133) | 1031 (214, 3480) | 1110 (191, 2863) | <0.01 | <0.05 | <0.05 | >0.05 |
| 19200 (7248, 41700) | 7160 (3443, 15675) | 5310 (1246, 14675) | <0.01 | <0.05 | <0.05 | >0.05 |
| 1307 (576, 10433) | 328 (47, 2598) | 151 (12.5, 1935) | <0.01 | <0.05 | <0.05 | >0.05 |
| 7920 (3428, 50600) | 437 (12.5, 3865) | 78 (12.5, 459) | <0.0001 | <0.05 | <0.05 | >0.05 |
| 3360 (644, 6805) | 449 (133, 2088) | 89 (12.5, 403) | <0.0001 | <0.05 | <0.05 | <0.05 |
| 117000 (44350, 207250) | 27950 (5410, 68750) | 18050 (2978, 46675) | <0.0001 | <0.05 | <0.05 | >0.05 |
| $1.12 \times 10^{10}$ ($6.68 \times 10^9$, $3.62 \times 10^{10}$) | $4.15 \times 10^9$ ($1.97 \times 10^9$, $9.45 \times 10^9$) | $4.28 \times 10^9$ ($1.40 \times 10^9$, $1.19 \times 10^{10}$) | <0.01 | <0.05 | <0.05 | >0.05 |

The 26 mRNAs and 18S rRNA levels shown in Table 3 were quantified using gene specific primers and probes by real-time PCR assay. Median absolute copy number per microgram of total RNA (interquartile range) of each mRNA measure and 18S rRNA are shown. P values were calculated using Kruskal-Wallis test of no differences among the Acute T-cell mediated rejection (ACR) biopsy group, Acute antibody mediated rejection (AMR) biopsy group and Acute tubular injury (ATI) biopsy group. After Kruskal-Wallis test, pair-wise comparisons among the three groups were performed using the Dunn's test. P-values <0.05 were considered statistically significant.

The levels of all 26 mRNAs and the levels of 18S rRNA were significantly different (P<0.05) in urinary cells from the patients with biopsies showing ACR, AMR or ATI by Kruskal-Wallis test. Pair-wise comparisons using Dunn's test showed that urinary cell levels of mRNA for CD3ε, perforin, FoxP3, and CD20 were significantly different between ACR and AMR, ACR and ATI and AMR and ATI. Pair-wise comparisons also showed that the levels of 18 rRNA were significantly different between ACR vs. AMR and ACR vs. ATI but not AMR vs. ATI (Table 3).

EXAMPLE 4

Development of a 6-gene Urinary Cell Diagnostic Signature to Differentiate Acute Rejection from Acute Tubular Injury (ATI)

This Example describes the development of a diagnostic signature to distinguish acute rejection (AR) from acute tubular injury (ATI).

Receiver-operating-characteristic (ROC) curve analyses of the urinary cell mRNA measures to differentiate AR (both types) from ATI are shown in Table 4.

TABLE 4

Receiver Operating Characteristic Curve Analysis of Urinary Cell mRNAs to Differentiate Acute Rejection (N = 52) from Acute Tubular Injury (N = 32)

| Urinary Cell mRNA | Area Under the Curve | 95% Confidence Interval | |
|---|---|---|---|
| CD3ε | 0.8786 | 0.8078 | 0.9493 |
| FoxP3 | 0.8705 | 0.8030 | 0.9379 |
| Perforin | 0.8395 | 0.7538 | 0.9252 |
| Immunoglobulin J | 0.8338 | 0.7395 | 0.9281 |
| Granzyme B | 0.8242 | 0.7356 | 0.9128 |
| CD20 | 0.8131 | 0.7175 | 0.9086 |
| OX40 | 0.7930 | 0.6974 | 0.8885 |
| CXCL13 | 0.7683 | 0.6601 | 0.8765 |
| CD105 | 0.7479 | 0.6405 | 0.8552 |
| PSMB10 | 0.7121 | 0.6019 | 0.8223 |
| TGFβ1 | 0.7112 | 0.5991 | 0.8234 |

TABLE 4-continued

Receiver Operating Characteristic Curve Analysis
of Urinary Cell mRNAs to Differentiate Acute Rejection
(N = 52) from Acute Tubular Injury (N = 32)

| Urinary Cell mRNA | Area Under the Curve | 95% Confidence Interval | |
|---|---|---|---|
| C3 | 0.7046 | 0.5867 | 0.8224 |
| C5 | 0.6989 | 0.5806 | 0.8171 |
| Complement Factor B | 0.6869 | 0.5669 | 0.8068 |
| CD146 | 0.6812 | 0.5595 | 0.8028 |
| Toll Like Receptor | 0.6572 | 0.5341 | 0.7801 |
| Von Willebrand Factor | 0.6665 | 0.5439 | 0.7892 |
| E cadherin | 0.6656 | 0.5431 | 0.7879 |
| Vimentin | 0.6502 | 0.5265 | 0.7739 |
| CD46 | 0.6487 | 0.5270 | 0.7704 |
| Interleukin 6 | 0.6469 | 0.5201 | 0.7737 |
| CD14 | 0.6352 | 0.5112 | 0.7591 |
| NKCC2 | 0.6247 | 0.5019 | 0.7474 |
| 18S rRNA | 0.6130 | 0.4860 | 0.7399 |
| TRIBS1 | 0.5980 | 0.4676 | 0.7282 |
| CD55 | 0.5965 | 0.4653 | 0.7276 |
| Complement Factor Properdin | 0.5895 | 0.4605 | 0.7185 |

Receiver-operating-characteristic (ROC) curve analyses of the urinary cell mRNA measures to differentiate AR (both types) from ATI are shown. Urinary cell levels of CD3ε mRNA differentiated the two groups best. To determine if combination of mRNAs better differentiated AR from ATI, we then used stepwise quadratic discriminant analysis to develop a linear combination of variables that best predicted the diagnostic groups. A six-gene model of natural logarithm (ln)-transformed mRNA values of CD3ε, CD105, TLR4, CD14, Complement factor B, and Vimentin emerged as the parsimonious model yielding a diagnostic signature that distinguished AR from ATI. This diagnostic signature better differentiated AR from ATI than CD3ε mRNA value alone (likelihood ratio test $\chi^2 = 40.6$, P < 0.0001).

Stepwise quadratic discriminant analysis was used to develop a linear combination of variables that best predicted the diagnostic groups (Dessing et al., *Nephrol Dial Transplant* 25: 4087-4092 (2010)). Because several patients in the ATI group had zero copies of FoxP3 mRNA, this mRNA was not included as an independent variable but all other measures of the twenty-five mRNAs and the 18S rRNA were used as independent variables in the analysis.

A six-gene model of natural logarithm (ln)-transformed mRNA values of CD3ε, CD105, TLR4, CD14, Complement factor B, and Vimentin emerged as the parsimonious model yielding the diagnostic signature that distinguished AR from ATI:

(0.52*ln CD3ε)+(1.02*ln CD105)+(0.81*ln TLR4)+
(−1.16*ln CD14)+(0.28*ln Complement Factor
B)+(−0.79*ln Vimentin)

where the unit of measurement in the PCR assay is copies/μg of total RNA. This diagnostic signature better differentiated AR from ATI than any single mRNA measure (e.g. vs. CD3ε [AUC: 0.88], likelihood ratio test $X^2=40.6$, P<0.0001). The diagnostic signature also outperformed other variables; time from transplantation to biopsy (AUC: 0.65), serum creatinine (AUC: 0.59) or tacrolimus trough levels (AUC: 0.77).

EXAMPLE 5

Internal Validation of the 6-gene Urinary Cell Diagnostic Signature

Figure 3A:
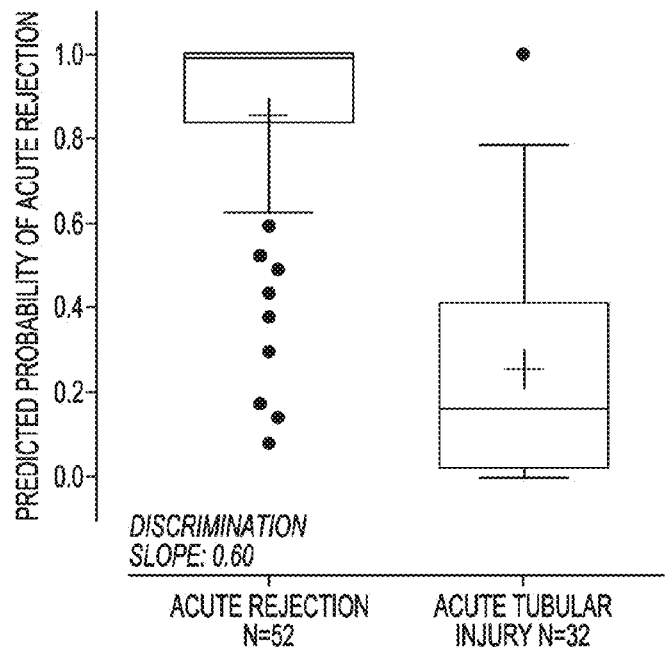
FIG. 3A-3B graphically illustrate differentiation of acute rejection from acute tubular injury.
Figure 3B:
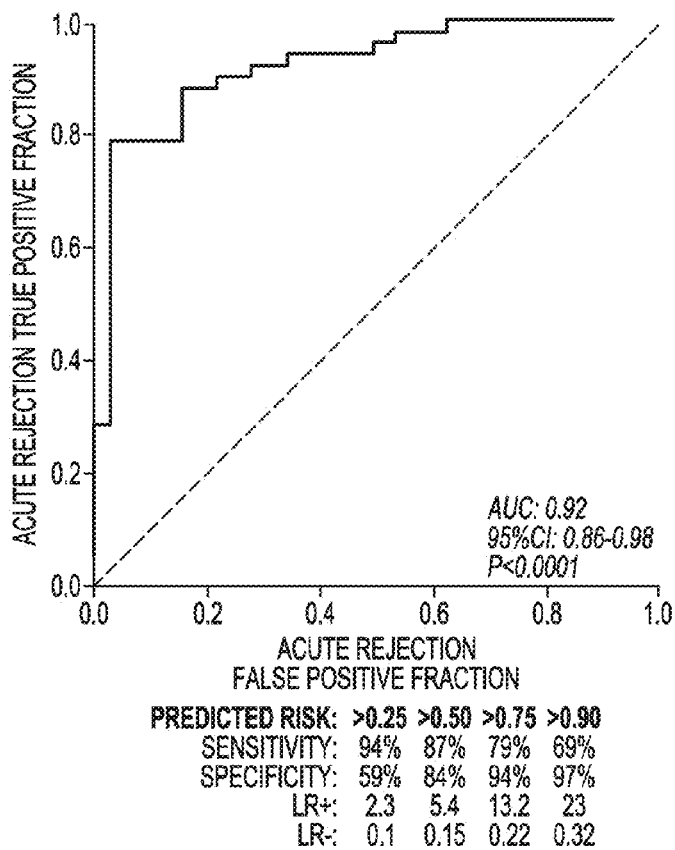

A 10-fold cross validation was performed to internally validate the 6-gene diagnostic signature (FIG. 3). The predicted probability for each patient from the cross validation was used to construct a ROC curve. The 6-gene model yielded a cross-validated estimate of the AUC of 0.92 (95% CI 0.86 to 0.98, P<0.0001). This is the estimate of the expected value of the AUC in an independent sample not used for deriving the diagnostic signature.

EXAMPLE 6

Clinical Benefit of the 6-gene Urinary Cell Diagnostic Signature

Figure 4B:
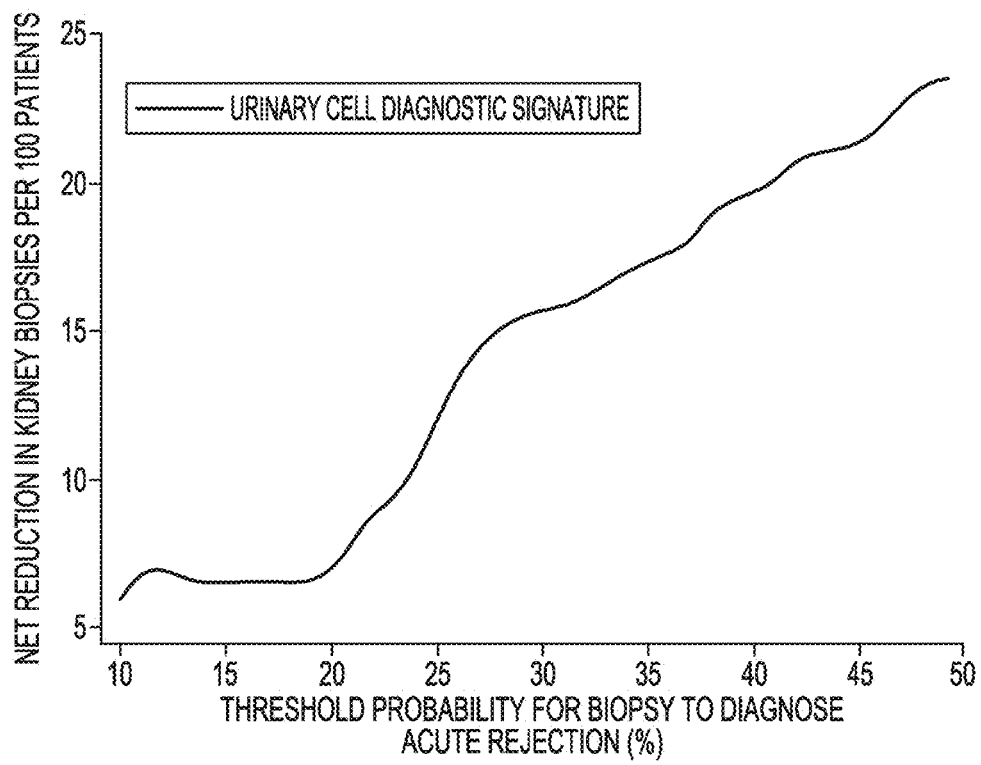

Decision curve analysis (FIG. 4A) was used to assess whether the signature was clinically beneficial (Vickers & Elkin, *Med Decis Making* 26: 565-574 (2006)). This analysis depicts the 'net benefit' of the signature at various threshold probabilities ($p_t$), the minimum expected probability of AR at which the physician in consultation with the patient opts for a biopsy to diagnose AR (e.g., if a physician will do a biopsy when the probability of AR in a patient is 20%, but will not do a biopsy if the probability is 19%, then the $p_t$ is 20%, but this $p_t$ may vary among physicians). The analysis showed that across a range of reasonable threshold probabilities from 10% to 50%, the highest net benefit was for the diagnostic signature. The net reduction in avoidable biopsies per 100 patients, when using the diagnostic signature, is shown in FIG. 4B.

EXAMPLE 7

Development and Validation of a 5-gene Urinary Cell Diagnostic Signature to Differentiate Acute Cellular Rejection from Acute Antibody Mediated Rejection After noninvasively distinguishing acute rejection from acute tubular injury using the 6-gene diagnostic signature, the inventors next determined if the two types of acute rejections (acute cellular rejection (ACR) and acute antibody mediated rejection (AMR)) could be differentiated without the need for an invasive biopsy (FIG. 1).

Table 5 shows the diagnostic value of individual mRNAs to differentiate ACR from AMR, as ascertained using the ROC curve analysis.

TABLE 5

Receiver Operating Characteristic Curve Analysis of Urinary
Cell mRNAs to Differentiate Acute T-Cell Mediated Rejection
(N = 26) from Acute Antibody Mediated Rejection (N = 26)

| Urinary Cell mRNA | Area Under the Curve | 95% Confidence Interval | |
|---|---|---|---|
| CD3ε | 0.8735 | 0.7758 | 0.9711 |
| FoxP3 | 0.8735 | 0.7741 | 0.9729 |
| PSMB10 | 0.8462 | 0.7415 | 0.9507 |
| CD14 | 0.8351 | 0.7256 | 0.9445 |
| CXCL13 | 0.8299 | 0.7207 | 0.9390 |
| Granzyme B | 0.8262 | 0.7129 | 0.9394 |
| Perforin | 0.8062 | 0.6864 | 0.9259 |
| OX40 | 0.8129 | 0.6968 | 0.9289 |
| TGFβ1 | 0.8047 | 0.6871 | 0.9223 |
| CD46 | 0.8010 | 0.6782 | 0.9238 |
| Vimentin | 0.7966 | 0.6725 | 0.9206 |
| Complement Factor Properdin | 0.7840 | 0.6604 | 0.9075 |
| CD105 | 0.7751 | 0.6427 | 0.9075 |
| TRIBS1 | 0.7714 | 0.6430 | 0.8999 |
| C5 | 0.7700 | 0.6401 | 0.8998 |
| 18S rRNA | 0.7663 | 0.6378 | 0.8948 |
| CD55 | 0.7611 | 0.6319 | 0.8902 |
| Interleukin 6 | 0.7382 | 0.6033 | 0.8730 |
| Toll Like Receptor 4 | 0.7352 | 0.5997 | 0.8706 |
| E cadherin | 0.7241 | 0.5847 | 0.8634 |
| CD20 | 0.7204 | 0.5694 | 0.8714 |

TABLE 5-continued

Receiver Operating Characteristic Curve Analysis of Urinary
Cell mRNAs to Differentiate Acute T-Cell Mediated Rejection
(N = 26) from Acute Antibody Mediated Rejection (N = 26)

| Urinary Cell mRNA | Area Under the Curve | 95% Confidence Interval | |
|---|---|---|---|
| C3 | 0.7145 | 0.5714 | 0.8575 |
| NKCC2 | 0.7034 | 0.5602 | 0.8465 |
| Immunoglobulin J | 0.6746 | 0.5202 | 0.8288 |
| CD146 | 0.6686 | 0.5192 | 0.8180 |
| Von Willebrand Factor | 0.6546 | 0.5029 | 0.8062 |
| Complement Factor B | 0.5673 | 0.4088 | 0.7258 |

The best determinant of ACR was the urinary cell level of CD3ε mRNA—CD3ε mRNA levels differentiated ACR from AMR the best. To determine if a combination of mRNAs better differentiated ACR from AMR, the inventors then used stepwise quadratic discriminant analysis to develop a linear combination of variables that best predicted the diagnostic groups. A five-gene model of ln-transformed mRNA values of CD3ε, CD105, CD14 and CD46 as well as ln-transformed 18S rRNA emerged as the parsimonious model yielding a diagnostic signature that distinguished ACR from AMR. This diagnostic signature better differentiated ACR from AMR than CD3ε mRNA value alone (likelihood ratio test $X^2$=30.4, P<0.0001).

A five-gene model of ln-transformed mRNA values of CD3ε, CD105, CD14, CD46 and 18S rRNA emerged as the parsimonious model yielding the following diagnostic signature:

$$(0.67*\ln CD3\epsilon)+(-1.18*\ln CD105)+(1.30*\ln CD14)+(-0.83*\ln CD46)+(0.45*\ln 18S).$$

Figure 5A:
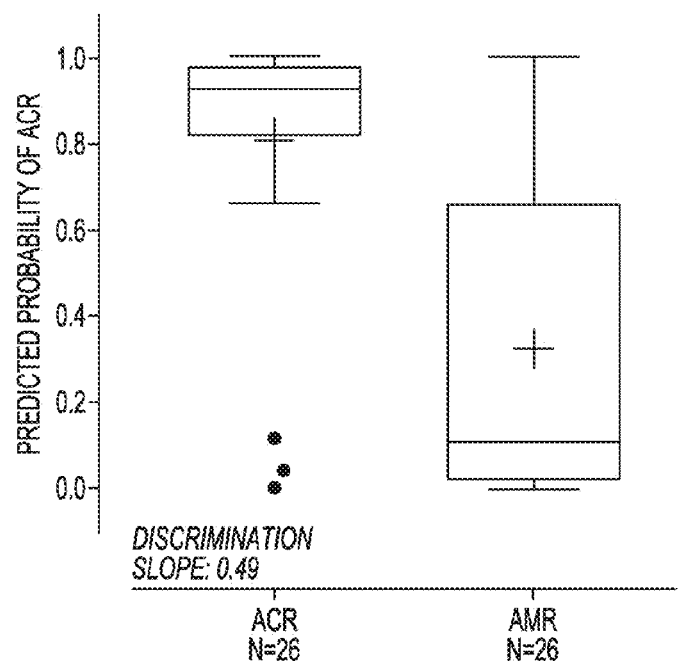
FIG. 5A-5B graphically illustrates the differentiation of acute T-cell mediated rejection from acute antibody-mediated rejection. After differentiation of acute rejection from acute tubular injury in step 1 (see, FIG. 1A), in step 2 and among patients diagnosed with acute rejection biopsies, another urinary cell diagnostic signature was derived to better differentiate ACR biopsies (N=26 patients) from AMR biopsies (N=26 patients) (see, FIG. 1A) than any single mRNA measure. By quadratic discriminant function analysis, a linear combination of four mRNAs (CD3ϵ, CD105, CD14, and CD46) and 18S rRNA emerged as the parsimonious model and yielded a discriminant score that constituted the diagnostic signature. Ten-fold cross validation was performed to internally validate the 5-gene diagnostic signature.
Figure 5B:
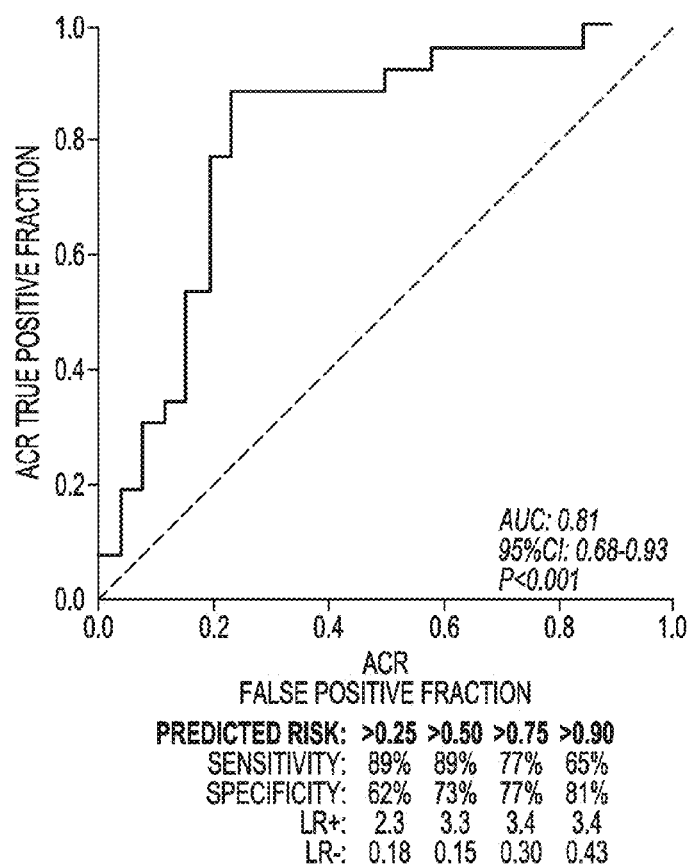

This diagnostic signature better differentiated ACR from AMR than any other single mRNA measure (e.g. vs. CD3ε [AUC: 0.87], likelihood ratio test $X^2$=30.4, P<0.0001). Ten-fold cross validation of this 5-gene model yielded an AUC of 0.81 (95% CI 0.68 to 0.93, P<0.001, FIG. 5).

EXAMPLE 8

Other Attributes of the Urinary Cell Diagnostic Signatures

The signatures were examined to determine whether they were diagnostic in patients induced with different types of induction therapy. The 6-gene signature distinguishes AR from ATI in those induced with lymphocyte depleting antibodies (P<0.0001) and in those induced with anti-interleukin-2 receptor antibodies or no induction (P<0.01) (Table 3). The inventors analysis also showed that the 5-gene signature distinguishes ACR from AMR in those induced with lymphocyte depleting antibodies (P<0.0001) and in those induced with anti-interleukin-2 receptor antibodies or no induction (P<0.0001) (Table 6).

TABLE 6

Urinary Cell Diagnostic Signature Score: Subgroup Analysis

| | | 6-gene Signature Score (AR vs. ATI) Median value[a] | | | | 5-gene Signature Score (ACR vs. AMR) Median value[a] | | |
|---|---|---|---|---|---|---|---|---|
| Variables | N | AR (N = 52) | ATI (N = 32) | P value | N | ACR (N = 26) | AMR (N = 26) | P value |
| Biopsy within 1 month of transplantation | 31 | 1.15 | −1.47 | <0.0001 | 19 | 10.18 | 7.87 | <0.0001 |
| Biopsy beyond 1 month of transplantation | 53 | 0.77 | −1.41 | <0.0001 | 33 | 10.21 | 8.10 | <0.0001 |
| P Value | | 0.7 | 0.6 | | | 0.7 | 0.3 | |
| Male | 52 | 0.98 | −1.45 | <0.0001 | 33 | 10.29 | 7.95 | <0.0001 |
| Female | 32 | 0.77 | −1.46 | <0.0001 | 19 | 10.11 | 7.88 | <0.01 |
| P Value | | 0.7 | 0.7 | | | 0.7 | 0.6 | |
| Black | 28 | 1.08 | −1.36 | <0.0001 | 19 | 10.34 | 8.05 | <0.001 |
| Others | 56 | 0.77 | −1.46 | <0.0001 | 33 | 10.08 | 7.90 | <0.0001 |
| P Value | | 0.7 | 0.8 | | | 0.5 | 0.6 | |
| Black donor | 17 | 1.61 | −1.87 | <0.01 | 12 | 10.29 | 8.38 | <0.01 |
| Other donor | 67 | 0.77 | −1.45 | <0.0001 | 40 | 10.18 | 7.87 | <0.0001 |
| P Value | | 0.6 | 0.3 | | | 0.9 | 0.2 | |
| Living donor | 41 | 1.11 | −1.45 | <0.0001 | 27 | 10.33 | 8.70 | <0.0001 |
| Deceased donor | 43 | 0.47 | −1.46 | <0.0001 | 25 | 10.11 | 7.87 | <0.0001 |
| P Value | | 0.1 | 0.7 | | | 0.5 | 0.04 | |
| History of delayed graft function | 26 | 1.30 | −1.34 | <0.0001 | 13 | 10.17 | 7.95 | <0.01 |
| No delayed graft function | 58 | 0.77 | −1.46 | <0.0001 | 39 | 10.22 | 7.92 | <0.0001 |
| P Value | | 0.9 | 0.6 | | | 0.9 | 0.7 | |
| Induction immunosuppression | 76 | 1.01 | −1.46 | <0.0001 | 44 | 10.11 | 7.98 | <0.0001 |
| No induction immunosuppression | 8 | 0.77 | —[b] | — | 8 | 11.06 | 7.40[c] | — |
| P Value | | 0.9 | — | | | 0.2 | — | |
| Lymphocyte depleting induction immunosuppression (Thymoglobulin ®)[d] | 59 | 1.11 | −1.50 | <0.0001 | 32 | 10.18 | 8.31 | <0.0001 |

TABLE 6-continued

Urinary Cell Diagnostic Signature Score: Subgroup Analysis

| Variables | N | 6-gene Signature Score (AR vs. ATI) Median value[a] | | | N | 5-gene Signature Score (ACR vs. AMR) Median value[a] | | |
|---|---|---|---|---|---|---|---|---|
| | | AR (N = 52) | ATI (N = 32) | P value | | ACR (N = 26) | AMR (N = 26) | P value |
| Lymphocyte non-depleting induction (Interleukin-2 receptor antibody) or no induction | 25 | 0.62 | −1.11 | <0.01 | 20 | 10.20 | 7.90 | <0.0001 |
| P Value | | 0.5 | 0.1 | | | 0.7 | 0.7 | |
| Maintenance immunosuppression with corticosteroids | 40 | 0.77 | −1.45 | <0.0001 | 33 | 10.61 | 7.87 | <0.0001 |
| Maintenance immunosuppression without corticosteroids | 44 | 1.30 | −1.46 | <0.0001 | 19 | 10.09 | 8.65 | <0.001 |
| P Value | | 0.4 | 0.8 | | | 0.4 | 0.1 | |
| History of bacterial urinary tract infection | 22 | 0.77 | −1.27 | <0.01 | 17 | 10.0 | 8.0 | <0.0001 |
| No bacterial urinary tract infection | 62 | 1.01 | −1.46 | <0.0001 | 35 | 10.3 | 7.9 | <0.0001 |
| P Value | | 0.8 | 0.5 | | | 0.4 | 0.6 | |
| Acute T-cell mediated rejection, Banff 4-Ia/Ib | 20 | 1.36 | — | — | 20 | 10.09 | — | — |
| Acute T-cell mediated rejection, Banff 4-IIa/IIb | 6 | 0.49 | — | — | 6 | 11.14 | — | — |
| P Value | | 0.3 | — | | | 0.1 | | |
| Concomitant interstitial fibrosis/tubular atrophy, nil-mild | 73 | 0.77 | −1.46 | <0.0001 | 42 | 10.25 | 7.87 | <0.0001 |
| Concomitant interstitial fibrosis/tubular atrophy, moderate-severe | 11 | 1.36 | −0.55[c] | — | 10 | 9.66 | 8.65 | 0.02 |
| P Value | | 0.9 | — | | | 0.8 | 0.3 | |

[a]Median values of the two diagnostic signature scores are shown for different subgroups of patient variables. P values are derived using the Mann-Whiney test.
[b]There were no patients in the "ATI and No induction immunosuppression" group
[c]N ≤ 2. Hence no statistical comparisons were done
[d]Includes one patient with Alemtuzumab (Campath®) induction Tacrolimus and mycophenolate were used as maintenance immunosuppressive therapy, with or without additional corticosteroids (Table 2). The signature discriminated AR from ATI in patients managed with or without corticosteroids maintenance therapy (P<0.0001, for both groups). The signature also distinguished ACR from AMR in patients managed with (P<0.0001) or without (P<0.001) corticosteroids maintenance therapy (Table 6).

Figure 6A:
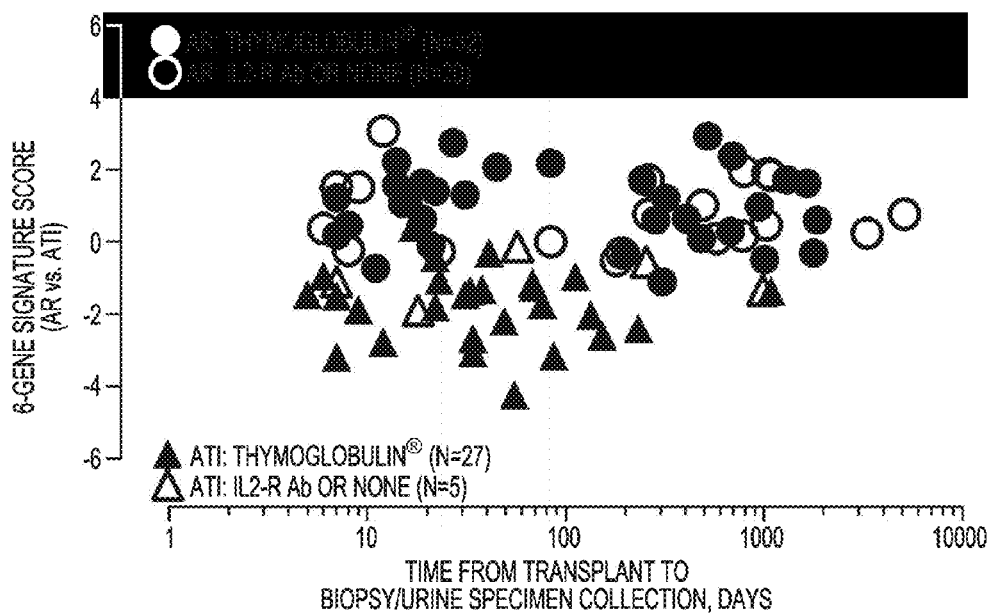
FIG. 6A-6B illustrate the relationship between the urinary cell diagnostic signature score and the time from transplantation to biopsy/urine sample collection.
Figure 6B:
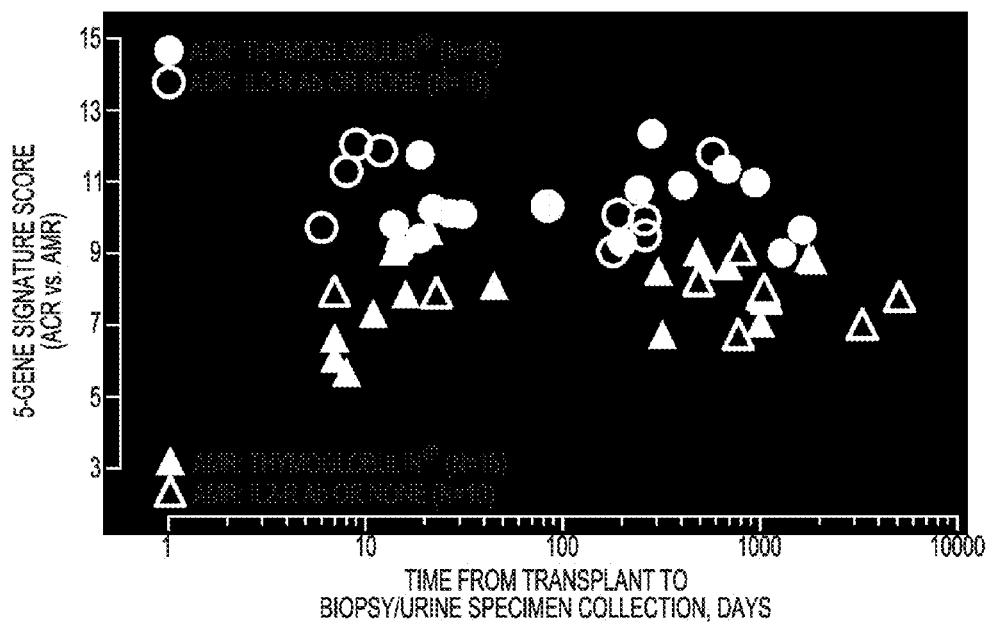

The inventors examined whether the two diagnostic signatures are associated with time from transplantation to biopsy/urine collection. Such evaluation showed that there was no significant relationship between the signatures and the time from transplantation to biopsy in patients induced with depleting or non-depleting antibodies (FIG. 6A-6B, Spearman's correlation, P>0.05).

REFERENCES

Solez, K, Colvin, R B, Racusen, L C, Haas, M, Sis, B, Mengel, M, Halloran, P F, Baldwin, W, Banfi, G, Collins, A B, Cosio, F, David, D S, Drachenberg, C, Einecke, G, Fogo, A B, Gibson, I W, Glotz, D, Iskandar, S S, Kraus, E, Lerut, E, Mannon, R B, Mihatsch, M, Nankivell, B J, Nickeleit, V, Papadimitriou, J C, Randhawa, P, Regele, H, Renaudin, K, Roberts, I, Seron, D, Smith, R N, Valente, M: Banff 07 classification of renal allograft pathology: updates and future directions. *Am J Transplant* 8: 753-760, 2008

Muthukumar, T, Dadhania, D, Ding, R, Snopkowski, C, Naqvi, R, Lee, J B, Hartono, C, Li, B, Sharma, V K, Seshan, S V, Kapur, S, Hancock, W W, Schwartz, J E, Suthanthiran, M: Messenger RNA for FOXP3 in the urine of renal-allograft recipients. *N Engl J Med* 353: 2342-2351, 2005

Suthanthiran, M, Schwartz, J E, Ding, R, Abecassis, M, Dadhania, D, Samstein, B, Knechtle, S J, Friedewald, J, Becker, Y T, Sharma, V K, Williams, N M, Chang, C S, Hoang, C, Muthukumar, T, August, P, Keslar, K S, Fairchild, R L, Hricik, D E, Heeger, P S, Han, L, Liu, J, Riggs, M, Ikle, D N, Bridges, N D, Shaked, A: Urinary-cell mRNA profile and acute cellular rejection in kidney allografts. *N Engl J Med* 369: 20-31, 2013

Dadhania D, Snopkowski C, Ding R, Muthukumar T, Chang C, Aull M, Lee J, Sharma V K, Kapur S, Suthanthiran M. Epidemiology of BK virus in renal allograft recipients: independent risk factors for BK virus replication. *Transplantation* 86: 521-528, 2008

Li, B, Hartono, C, Ding, R, Sharma, V K, Ramaswamy, R, Qian, B, Serur, D, Mouradian, J, Schwartz, J E, Suthanthiran, M: Noninvasive diagnosis of renal-allograft rejection by measurement of messenger RNA for perforin and granzyme B in urine. *N Engl J Med* 344: 947-954, 2001

Afaneh, C, Muthukumar, T, Lubetzky, M, Ding, R, Snopkowski, C, Sharma, V K, Seshan, S, Dadhania, D, Schwartz, J E, Suthanthiran, M: Urinary cell levels of mRNA for OX40, OX40L, PD-1, PD-L1, or PD-L2 and acute rejection of human renal allografts. *Transplantation* 90: 1381-1387, 2010

Woywodt, A, Schroeder, M, Gwinner, W, Mengel, M, Jaeger, M, Schwarz, A, Haller, H, Haubitz, M: Elevated numbers of circulating endothelial cells in renal transplant recipients. *Transplantation* 76: 1-4, 2003

Perco, P, Kainz, A, Wilflingseder, J, Soleiman, A, Mayer, B, Oberbauer, R: Histogenomics: association of gene expression patterns with histological parameters in kidney biopsies. *Transplantation* 87: 290-295, 2009

Ashton-Chess, J, Mai, H L, Jovanovic, V, Renaudin, K, Foucher, Y, Giral, M, Moreau, A, Dugast, E, Mengel, M, Racape, M, Danger, R, Usal, C, Smit, H, Guillet, M, Gwinner, W, Le Berre, L, Dantal, J, Soulillou, J P, Brouard, S: Immunoproteasome beta subunit 10 is increased in chronic antibody-mediated rejection. *Kidney Int* 77: 880-890, 2010

Ashton-Chess, J, Giral, M, Mengel, M, Renaudin, K, Foucher, Y, Gwinner, W, Braud, C, Dugast, E, Quillard, T, Thebault, P, Chiffoleau, E, Braudeau, C, Charreau, B, Soulillou, J P, Brouard, S: Tribbles-1 as a novel biomarker of chronic antibody-mediated rejection. *J Am Soc Nephrol* 19: 1116-1127, 2008

Dessing, M C, Bemelman, F J, Claessen, N, Ten Berge, I J, Florquin, S, Leemans, J C: Intragraft Toll-like receptor profiling in acute renal allograft rejection. *Nephrol Dial Transplant* 25: 4087-4092, 2010

Bogman, M J, Dooper, I M, van de Winkel, J G, Tax, W J, Hoitsma, A J, Assmann, K J, Ruiter, D J, Koene, R A: Diagnosis of renal allograft rejection by macrophage immunostaining with a CD14 monoclonal antibody, WT14. *Lancet* 2: 235-238, 1989

Stegall, M D, Chedid, M F, Cornell, L D: The role of complement in antibody-mediated rejection in kidney transplantation. *Nat Rev Nephrol* 8: 670-678, 2012

Anglicheau, D, Muthukumar, T, Hummel, A, Ding, R, Sharma, V K, Dadhania, D, Seshan, S V, Schwartz, J E, Suthanthiran, M: Discovery and validation of a molecular signature for the noninvasive diagnosis of human renal allograft fibrosis. *Transplantation* 93: 1136-1146, 2012

De Serres, S A, Mfarrej, B G, Grafals, M, Riella, L V, Magee, C N, Yeung, M Y, Dyer, C, Ahmad, U, Chandraker, A, Najafian, N: Derivation and validation of a cytokine-based assay to screen for acute rejection in renal transplant recipients. *Clin J Am Soc Nephrol* 7: 1018-1025, 2012

Steinmetz, O M, Panzer, U, Kneissler, U, Harendza, S, Lipp, M, Helmchen, U, Stahl, R A: BCA-1/CXCL13 expression is associated with CXCR5-positive B-cell cluster formation in acute renal transplant rejection. *Kidney Int* 67: 1616-1621, 2005

Sarwal, M, Chua, M S, Kambham, N, Hsieh, S C, Satterwhite, T, Masek, M, Salvatierra, O, Jr.: Molecular heterogeneity in acute renal allograft rejection identified by DNA microarray profiling. *N Engl J Med* 349: 125-138, 2003

Hair, J F, Anderson, R E, Tatham, R L, Black, W C: (Eds.) *Multivariate Analysis*, Upper Saddle river, New Jersey, Prentice hall, 1998

Steyerberg, E W, Vickers, A J, Cook, N R, Gerds, T, Gonen, M, Obuchowski, N, Pencina, M J, Kattan, M W: Assessing the performance of prediction models: a framework for traditional and novel measures. *Epidemiology* 21: 128-138, 2010

Vickers, A J, Elkin, E B: Decision curve analysis: a novel method for evaluating prediction models. *Med Decis Making* 26: 565-574, 2006

Steyerberg, E W, Vickers, A J: Decision curve analysis: a discussion. *Med Decis Making* 28: 146-149, 2008

Vickers, A J: Decision analysis for the evaluation of diagnostic tests, prediction models and molecular markers. *Am Stat* 62: 314-320, 2008.

Knechtle, S J, Pirsch, J D: Early Course of the patient with a Kidney Transplant. In: *Kidney Transplantation: Principles and Practice*. 6 ed. edited by Morris, P. J., Knechtle, S. J., Philadelphia, Saunders, 2008, pp 210-219

Wilkinson, A: The "First Quarter". The First Three Months After Transplant. In: *Handbook of Kidney Transplantation*. 5 ed. edited by Danovitch, G. M., Philadelphia, Lippincott Willimas & Wilkins, 2010, pp 198-216

Al-Awwa, I A, Hariharan, S, First, M R: Importance of allograft biopsy in renal transplant recipients: correlation between clinical and histological diagnosis. *Am J Kidney Dis* 31: S15-18, 1998

Pascual, M, Vallhonrat, H, Cosimi, A B, Tolkoff-Rubin, N, Colvin, R B, Delmonico, F L, Ko, D S, Schoenfeld, D A, Williams, W W, Jr.: The clinical usefulness of the renal allograft biopsy in the cyclosporine era: a prospective study. *Transplantation* 67: 737-741, 1999

Furness, P N, Taub, N: International variation in the interpretation of renal transplant biopsies: report of the CERT-PAP Project. *Kidney Int* 60: 1998-2012, 2001.

Williams, W W, Taheri, D, Tolkoff-Rubin, N, Colvin, R B: Clinical role of the renal transplant biopsy. *Nat Rev Nephrol* 8: 110-121, 2012

Li, B, Hartono, C, Ding, R, Sharma, V K, Ramaswamy, R, Qian, B, Serur, D, Mouradian, J, Schwartz, J E, Suthanthiran, M: Noninvasive diagnosis of renal-allograft rejection by measurement of messenger RNA for perforin and granzyme B in urine. *N Engl J Med* 344: 947-954, 2001

Muthukumar, T, Dadhania, D, Ding, R, Snopkowski, C, Naqvi, R, Lee, J B, Hartono, C, Li, B, Sharma, V K, Seshan, S V, Kapur, S, Hancock, W W, Schwartz, J E, Suthanthiran, M: Messenger RNA for FOXP3 in the urine of renal-allograft recipients. *N Engl J Med* 353: 2342-2351, 2005

Anglicheau, D, Muthukumar, T, Hummel, A, Ding, R, Sharma, V K, Dadhania, D, Seshan, S V, Schwartz, J E, Suthanthiran, M: Discovery and validation of a molecular signature for the noninvasive diagnosis of human renal allograft fibrosis. *Transplantation* 93: 1136-1146, 2012

Suthanthiran, M, Schwartz, J E, Ding, R, Abecassis, M, Dadhania, D, Samstein, B, Knechtle, S J, Friedewald, J, Becker, Y T, Sharma, V K, Williams, N M, Chang, C S, Hoang, C, Muthukumar, T, August, P, Keslar, K S, Fairchild, R L, Hricik, D E, Heeger, P S, Han, L, Liu, J, Riggs, M, Ikle, D N, Bridges, N D, Shaked, A: Urinary-cell mRNA profile and acute cellular rejection in kidney allografts. *N Engl J Med* 369: 20-31, 2013

Hair, J F, Anderson, R E, Tatham, R L, Black, W C: (Eds.) *Multivariate Analysis*, Upper Saddle river, New Jersey, Prentice hall, 1998

Vickers, A J, Elkin, E B: Decision curve analysis: a novel method for evaluating prediction models. *Med Decis Making* 26: 565-574, 2006.

Vickers, A J: Decision analysis for the evaluation of diagnostic tests, prediction models and molecular markers. *Am Stat* 62: 314-320, 2008

Steyerberg, E W, Vickers, A J: Decision curve analysis: a discussion. *Med Decis Making* 28: 146-149, 2008

Kon, S P, Templar, J, Dodd, S M, Rudge, C J, Raftery, M J: Diagnostic contribution of renal allograft biopsies at various intervals after transplantation. *Transplantation*, 63: 547-550, 1997

Heyne, N, Kemmner, S, Schneider, C, Nadalin, S, Konigsrainer, A, Haring, H U: Urinary neutrophil gelatinase-associated lipocalin accurately detects acute allograft rejection among other causes of acute kidney injury in renal allograft recipients. *Transplantation* 93: 1252-1257, 2012

De Serres, S A, Mfarrej, B G, Grafals, M, Riella, L V, Magee, C N, Yeung, M Y, Dyer, C, Ahmad, U, Chandraker, A, Najafian, N: Derivation and validation of a cytokine-based assay to screen for acute rejection in renal transplant recipients. *Clin J Am Soc Nephrol* 7: 1018-1025, 2012

Lattenist, L, Kers, J, Claessen, N, ten Berge, I J, Bemelman, F J, Florquin, S, Roelofs, J J: Renal and urinary levels of Endothelial Protein C Receptor correlate with acute renal allograft rejection. *PLoS ONE* 8: e64994, 2013

Solez, K, Colvin, R B, Racusen, L C, Haas, M, Sis, B, Mengel, M, Halloran, P F, Baldwin, W, Banfi, G, Collins, A B, Cosio, F, David, D S, Drachenberg, C, Einecke, G, Fogo, A B, Gibson, I W, Glotz, D, Iskandar, S S, Kraus, E, Lerut, E, Mannon, R B, Mihatsch, M, Nankivell, B J, Nickeleit, V, Papadimitriou, J C, Randhawa, P, Regele, H, Renaudin, K, Roberts, I, Seron, D, Smith, R N, Valente, M: Banff 07 classification of renal allograft pathology: updates and future directions. *Am J Transplant* 8: 753-760, 2008

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The following statements summarize aspects of the invention.

Statements:

1. A method of detecting acute kidney rejection in a subject comprising detecting urinary RNA expression levels in a test urinary sample from the subject.
2. The method of statement 1, wherein detecting urinary RNA expression levels comprises detection of one or more of the following: CD3ε, CD105, TLR4, CD14, CD46, complement factor B, vimentin, and 18S rRNA in the test sample.
3. The method of statement 1 or 2, wherein detecting urinary RNA expression levels comprises detection of two or more (at least two) of the following: CD3ε, CD105, TLR4, CD14, CD46, complement factor B, vimentin, and 18S rRNA expression levels in the test sample.
4. The method of any of statements 1-3, wherein detecting urinary RNA expression levels comprises detection of three or more (at least three) of the following: CD3ε, CD105, TLR4, CD14, CD46, complement factor B, vimentin, and 18S rRNA expression levels in the test sample.
5. The method of any of statements 1-4, wherein detecting urinary RNA expression levels comprises detection of four or more (at least four) of the following: CD3ε, CD105, TLR4, CD14, CD46, complement factor B, vimentin, and 18S rRNA expression levels in the test sample.
6. The method of any of statements 1-5, wherein detecting urinary RNA expression levels comprises detection of five or more (at least five) of the following: CD3ε, CD105, TLR4, CD14, CD46, complement factor B, vimentin, and 18S rRNA expression levels in the test sample.
7. The method of any of statements 1-6, wherein detecting urinary RNA expression levels comprises detection of six or more (at least six) of the following: CD3ε, CD105, TLR4, CD14, CD46, complement factor B, vimentin, and 18S rRNA expression levels in the test sample.
8. The method of any of statements 1-7, further comprising distinguishing acute kidney rejection from acute tubular injury (without acute rejection) comprising detecting urinary RNA expression levels in a test urinary sample from the subject.
9. The method of statement 8, wherein distinguishing acute kidney rejection from acute tubular injury (without acute rejection) comprises detection of RNA expression levels in the test urinary sample for one or more RNAs for CD3ε, CD105, TLR4, CD14, complement factor B, vimentin, or any combination thereof.
10. The method of statement 8 or 9, wherein distinguishing acute kidney rejection from acute tubular injury (without acute rejection) comprises detection of RNA expression levels in the test urinary sample for two or more RNAs for CD3ε, CD105, TLR4, CD14, complement factor B, or vimentin.
11. The method of any of statements 8-10, wherein distinguishing acute kidney rejection from acute tubular injury (without acute rejection) comprises detection of RNA expression levels in the test urinary sample for three or more RNAs for CD3ε, CD105, TLR4, CD14, complement factor B, or vimentin.
12. The method of any of statements 8-11, wherein distinguishing acute kidney rejection from acute tubular injury (without acute rejection) comprises detection of RNA expression levels in the test urinary sample for four or more RNAs for CD3ε, CD105, TLR4, CD14, complement factor B, or vimentin.
13. The method of any of statements 8-12, wherein distinguishing acute kidney rejection from acute tubular injury (without acute rejection) comprises detection of RNA expression levels in the test urinary sample for five or more RNAs for CD3ε, CD105, TLR4, CD14, complement factor B, or vimentin.
14. The method of any of statements 8-13, wherein distinguishing acute kidney rejection from acute tubular injury (without acute rejection) comprises detection of RNA expression levels in the test urinary sample for CD3ε, CD105, TLR4, CD14, complement factor B, and vimentin.

15. The method of any of statements 1-14, further comprising distinguishing T-cell mediated rejection (ACR) from antibody-mediated rejection (AMR) comprising detecting urinary RNA expression levels in a test urinary sample from the subject.

16. The method of statement 15, wherein distinguishing T-cell mediated rejection (ACR) from antibody-mediated rejection (AMR) comprises detection of RNA expression levels in the test urinary sample for one or more RNAs for CD3ε, CD105, CD14, CD46, 18S rRNA, or any combination thereof.

17. The method of statement 15 or 16, wherein distinguishing T-cell mediated rejection (ACR) from antibody-mediated rejection (AMR) comprises detection of RNA expression levels in the test urinary sample for two or more RNAs for CD3ε, CD105, CD14, CD46, or 18S rRNA.

18. The method of any of statements 15-17, wherein distinguishing T-cell mediated rejection (ACR) from antibody-mediated rejection (AMR) comprises detection of RNA expression levels in the test urinary sample for three or more RNAs for CD3ε, CD105, CD14, CD46, or 18S rRNA.

19. The method of any of statements 15-18, wherein distinguishing T-cell mediated rejection (ACR) from antibody-mediated rejection (AMR) comprises detection of RNA expression levels in the test urinary sample for four or more RNAs for CD3ε, CD105, CD14, CD46, or 18S rRNA.

20. The method of any of statements 15-19, wherein distinguishing T-cell mediated rejection (ACR) from antibody-mediated rejection (AMR) comprises detection of RNA expression levels in the test urinary sample for RNAs for CD3ε, CD105, CD14, CD46, and 18S rRNA.

21. The method of any of statements 1-20, wherein measuring urinary RNA expression levels comprises reverse transcription of RNA isolated from the test urinary cell sample of the subject.

22. The method of any of statements 1-21, wherein measuring urinary RNA expression levels comprises hybridization and/or primer extension of at least one probe or primer that selectively hybridizes to CD3ε, CD105, TLR4, CD14, CD46, complement factor B, vimentin, or 18S rRNA.

23. The method of any of statements 1-22, wherein measuring urinary RNA expression levels comprises hybridization and/or primer extension of at least one probe or primer selected from primers or probes listed in Table 1.

24. The method of any of statements 1-23, wherein measuring urinary RNA expression levels comprises preamplification of urinary RNA from the sample.

25. The method of any of statements 1-24, wherein measuring urinary RNA expression levels comprises quantitative polymerase chain reaction of one or more of the following RNAs, or cDNAs generated from one or more of the following RNAs: CD3ε, CD105, TLR4, CD14, CD46, complement factor B, vimentin, and 18S rRNA.

26. The method of any of statements 1-25, wherein measuring urinary RNA expression levels comprises quantifying amounts of one or more of the following RNAs: CD3ε, CD105, TLR4, CD14, CD46, complement factor B, vimentin, and 18S rRNA as copies of RNA per microgram of total RNA.

27. The method of any of statements 1-26, further comprising identifying increased expression of one or more of the CD3ε, CD105, TLR4, CD14, CD46, complement factor B, vimentin, and 18S rRNA to thereby detect, predict, or monitor acute kidney rejection in a subject.

28. The method of any of statements 1-27, further comprising identifying increased expression of CD3ε, CD105, TLR4, CD14, complement factor B, and vimentin.

29. The method of any of statements 1-28, further comprising identifying increased expression of each of the following mRNAs CD3ε, CD105, TLR4, CD14, complement factor B, and vimentin.

30. The method of any of statements 1-29, comprising identifying increased expression of each of the following mRNAs CD3ε, CD105, TLR4, CD14, complement factor B, and vimentin using the following six-gene diagnostic signature that distinguishes acute rejection from acute tubular injury:

$$(0.52*\ln CD3\epsilon)+(1.02*\ln CD105)+(0.81*\ln TLR4)+ \\ (-1.16*\ln CD14)+(0.28*\ln \text{Complement Factor} \\ B)+(-0.79*\ln \text{Vimentin});$$

wherein a six-gene diagnostic signature of greater than about −0.24, or greater than about −0.2, or greater than −0.1, or greater than 0, or greater than 0.1, or greater than 0.2, or greater than 0.3, or greater than 0.4 indicates that the transplanted kidney in the patient from whom the tested sample was obtained is acutely rejecting the transplanted kidney, or will develop acute rejection of the transplanted kidney.

31. The method of any of statements 1-30, wherein measuring urinary RNA expression levels comprises measuring amounts of each of the following mRNAs: CD3ε, CD105, CD14, CD46 and 18S rRNA.

32. The method of any of statements 1-31, wherein measuring urinary RNA expression levels comprises quantifying amounts of one or more of the following RNAs: CD3ε, CD105, CD14, CD46 and 18S rRNA.

33. The method of any of statements 1-32, further comprising identifying increased expression of one or more of the following RNAs: CD3ε, CD105, CD14, CD46 and 18S rRNA.

34. The method of any of statements 1-33, comprising identifying increased expression of each of the following mRNAs CD3ε, CD105, CD14, CD46 and 18S rRNA using the following six-gene diagnostic signature that distinguishes acute cellular rejection (ACR) from antibody-mediated rejection (AMR):

$$(0.67*\ln CD3\epsilon)+(-1.18*\ln CD105)+(1.30*\ln \\ CD14)+(-0.83*\ln CD46)+(0.45*\ln 18S)$$

wherein a five-gene diagnostic signature of greater than about 9.24, or greater than about 9.3, or greater than about 9.4, or greater than about 9.5, or greater than about 9.6, or greater than about 9.7, or greater than about 9.8, or greater than about 9.9 indicates that the transplanted kidney in the patient from whom the tested sample was obtained is undergoing acute cellular rejection, or will develop acute cellular rejection, rather than antibody-mediated rejection.

35. The method of any of statements 1-34, further comprising treatment of subject in need thereof.

36. The method of any of statements 1-35, further comprising treatment of subject when one or RNA expression levels differs from a control or baseline RNA expression level of a control RNA selected from the group consisting of CD3ε, CD105, TLR4, CD14, CD46, complement factor B, vimentin, 18S rRNA expression levels, or any combination thereof.

37. The method of statement 36, wherein the control or baseline RNA expression level is that of a healthy subject.

38. A method of detecting lack of acute kidney rejection comprising measuring urinary RNA expression levels of one or more of the following: CD3ε, CD105, TLR4, CD14, CD46, complement factor B, vimentin, and 18S rRNA expression levels in a test urinary cell sample from a subject with a kidney transplant, identifying no increased expression of one or more of the CD3ε, CD105, TLR4, CD14, CD46, complement factor B, vimentin, and 18S rRNA to thereby detect lack of acute kidney rejection in a subject.

39. A method of detecting, predicting, or monitoring acute rejection of a kidney transplant comprising
  (a) measuring urinary RNA expression levels of the following genes: CD3ε, CD105, TLR4, CD14, complement factor B, and vimentin in a test urinary cell sample from a subject with a kidney transplant; and
  (b) identifying increased expression of the CD3ε mRNA CD105 mRNA, TLR4 mRNA, CD14 mRNA, complement factor B mRNA, and vimentin mRNA compared to a baseline to thereby detect, predict, or monitor acute rejection of a kidney transplant in the subject.

40. The method of statement 39, wherein the method identifies acute cellular rejection in the sample, and distinguishes patients with acute rejection from patients with acute tubular injury.

41. The method of statement 39 or 40, wherein the baseline is an average or median amount of expression for the corresponding gene in urinary cells from a group of healthy patients or from a group of patients with a known kidney problem.

42. The method of any of statements 39-41, wherein measuring urinary RNA expression levels comprises:
  reverse transcription of RNA isolated from the test urinary cell sample of the subject;
  hybridization and/or primer extension of at least one probe or primer that selectively hybridizes to CD3ε, CD105, TLR4, CD14, complement factor B, vimentin, CD46, or 18S rRNA;
  preamplification of urinary RNA from the sample;
  quantitative polymerase chain reaction of at least six of the following RNAs, or cDNAs generated from at least six of the following RNAs: CD3ε, CD105, TLR4, CD14, complement factor B, vimentin, CD46, and 18S rRNA;
  quantifying amounts of at least six of the following RNAs: CD3ε, CD105, TLR4, CD14, CD46, complement factor B, vimentin, and 18S rRNA, each as copy number of RNA per microgram of total RNA; or
  a combination thereof.

43. The method of any of statements 39-42, comprising identifying increased expression of each of the following mRNAs: CD3ε, CD105, TLR4, CD14, complement factor B, and vimentin using the following six-gene diagnostic signature that distinguishes acute rejection from acute tubular injury:

$$(0.52*\ln CD3\epsilon)+(1.02*\ln CD105)+(0.81*\ln TLR4)+(-1.16*\ln CD14)+(0.28*\ln \text{Complement Factor B})+(-0.79*\ln \text{Vimentin});$$

wherein a patient whose test urinary cell sample has a six-gene diagnostic signature of greater than about −0.24 has a transplanted kidney that is undergoing acute rejection, or will develop acute rejection.

44. The method of statement 43, further comprising treatment of subject for acute rejection of a kidney transplant when the six-gene diagnostic signature is greater than about −0.24.

45. The method of any of statements 39-44, further comprising identifying expression of each of the following mRNAs: CD3ε, CD105, TLR4, CD14, complement factor B, and vimentin using the following six-gene diagnostic signature that distinguishes acute rejection from acute tubular injury:

$$(0.52*\ln CD3\epsilon)+(1.02*\ln CD105)+(0.81*\ln TLR4)+(-1.16*\ln CD14)+(0.28*\ln \text{Complement Factor B})+(-0.79*\ln \text{Vimentin});$$

wherein a patient whose test urinary cell sample has a six-gene diagnostic signature of less than about −0.24 has a transplanted kidney that is undergoing acute tubular injury, or will develop acute tubular injury.

46. The method of statement 45, further comprising treatment of a subject for acute tubular injury when the six-gene diagnostic signature is less than about −0.25, or less than about −0.3.

47. The method of any of statements 39-46, further comprising measuring urinary RNA expression levels of CD46, and 18S rRNA and identifying increased expression CD46, and 18S rRNA compared to a baseline, to thereby distinguish acute cellular rejection (ACR) from antibody-mediated rejection (AMR) of a kidney transplant in a subject.

48. A method of detecting, predicting, or monitoring acute cellular rejection of a kidney transplant comprising
  (a) measuring urinary RNA expression levels of the following genes: CD3ε, CD105, CD14, CD46 and 18S rRNA in a test urinary cell sample from a subject with a kidney transplant; and
  (b) identifying increased expression of the CD3ε mRNA, CD105 mRNA, CD14 mRNA, CD46 mRNA, and 18S rRNA compared to a baseline to thereby detect, predict, or monitor acute cellular rejection of a kidney transplant in the subject.

49. A method of statement 48, wherein identifying increased expression of the CD3ε mRNA, CD105 mRNA, CD14 mRNA, CD46 mRNA, and 18S rRNA comprises using the following five-gene diagnostic signature that distinguishes acute cellular rejection (ACR) from antibody-mediated rejection (AMR):

$$(0.67*\ln CD3\epsilon)+(-1.18*\ln CD105)+(1.30*\ln CD14)+(-0.83*\ln CD46)+(0.45*\ln 18S)$$

wherein a patient whose test urinary cell sample has a five-gene diagnostic signature of greater than about 9.24 has a transplanted kidney that is undergoing acute cellular rejection, or will develop acute cellular rejection, rather than antibody-mediated rejection.

50. The method of statement 48 or 49, further comprising treatment of subject for acute cellular rejection when the five-gene diagnostic signature is greater than about 9.24.

51. A method of detecting, predicting, or monitoring antibody-mediated rejection of a kidney transplant comprising
   (a) measuring urinary RNA expression levels of the following genes: CD3ε, CD105, CD14, CD46 and 18S rRNA in a test urinary cell sample from a subject with a kidney transplant; and
   (b) identifying reduced expression of the CD3ε mRNA, CD105 mRNA, CD14 mRNA, CD46 mRNA, and 18S rRNA compared to a baseline to thereby detect, predict, or monitor antibody-mediated rejection of a kidney transplant in the subject.

52. The method of statement 51, wherein identifying reduced expression of each of the following mRNAs CD3ε, CD105, CD14, CD46 and 18S rRNA comprises using the following five-gene diagnostic signature that distinguishes acute cellular rejection (ACR) from antibody-mediated rejection (AMR):

$$(0.67*\ln CD3\epsilon)+(-1.18*\ln CD105)+(1.30*\ln CD14)+(-0.83*\ln CD46)+(0.45*\ln 18S)$$

wherein a patient whose test urinary cell sample has a five-gene diagnostic signature of less than about 9.2 has a transplanted kidney that is undergoing antibody-mediated rejection, or will develop antibody-mediated rejection, rather than acute cellular rejection.

53. The method of statement 52, further comprising treatment of subject for antibody-mediated rejection when the five-gene diagnostic signature is less than about 9.2, or less than about 9.3.

54. A method of detecting lack of acute kidney rejection comprising measuring urinary RNA expression levels of the following: CD3ε, CD105, TLR4, CD14, complement factor B, and vimentin expression levels in a test urinary cell sample from a subject with a kidney transplant, identifying no increased expression of the following RNAs: CD3ε, CD105, TLR4, CD14, CD46, complement factor B, vimentin, and 18S rRNA in the test urinary cell sample to thereby detect lack of acute kidney rejection in a subject.

55. A kit comprising instructions for detecting acute rejection of a kidney transplant, and probes or primers for selective hybridization to at least five mRNAs selected from the group: CD3ε, CD105, TLR4, CD14, complement factor B, vimentin, CD46, and 18S rRNA.

56. The kit of statement 55, comprising at least one probe or primer for each of the following mRNAs: CD3ε, CD105, TLR4, CD14, complement factor B, and vimentin.

57. The kit of statement 55 or 56, wherein the instructions comprise the following signature for distinguishing acute rejection of a kidney transplant from acute tubular injury to the kidney transplant:

$$(0.52*\ln CD3\epsilon)+(1.02*\ln CD105)+(0.81*\ln TLR4)+(-1.16*\ln CD14)+(0.28*\ln Complement Factor B)+(-0.79*\ln Vimentin);$$

wherein a patient whose test urinary cell sample has a six-gene diagnostic signature of greater than about −0.24 has a transplanted kidney that is undergoing acute rejection, or will develop acute rejection.

58. The kit of any of statements 55-57, comprising at least one probe or primer for each of the following mRNAs: CD46, and 18S rRNA.

59. The kit of any of statements 55-58, wherein the instructions comprise the following method for distinguishing acute cellular rejection (ACR) from antibody-mediated rejection (AMR):

$$(0.67*\ln CD3\epsilon)+(-1.18*\ln CD105)+(1.30*\ln CD14)+(-0.83*\ln CD46)+(0.45*\ln 18S)$$

wherein a patient whose test urinary cell sample has a five-gene diagnostic signature of greater than about 9.24 has a transplanted kidney that is undergoing acute cellular rejection, or will develop acute cellular rejection, rather than antibody-mediated rejection.

60. Use of at least one oligonucleotide probe or primer that is complementary to an RNA selected from the group consisting of CD3ε, CD105, TLR4, CD14, CD46, complement factor B, vimentin, 18S rRNA expression levels, or any combination thereof, for detection of acute kidney rejection in a urinary test sample from a subject.

61. The use of statement 38, wherein at least one probe or primer is selected from primers or probes listed in Table 1.

The specific methods, compositions, kits, and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which are not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acids or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The Abstract is provided to allow the reader to quickly ascertain the nature and gist of the technical disclosure. The Abstract is submitted with the understanding that it will not be used to interpret or limit the scope or meaning of the claims.

What is claimed:

1. A method comprising:
   (a) measuring urinary RNA expression levels of the following genes: CD3ε, CD105, TLR4, CD14, complement factor B, and vimentin as copies of RNA per microgram of total RNA using at least one probe or primer with a sequence selected from SEQ ID NO: 10, 11, 12, 25, 26, 27, 43, 44, 45, 46, 47, 48, 58, 59, or 60, in a test urinary cell sample from a subject with a kidney transplant to provide measured CD3ε, CD105, TLR4, CD14, Complement factor B, and Vimentin mRNA expression levels; and
   (b) determining a six-gene diagnostic signature for the subject from natural log (ln) values of measured CD3ε, CD105, TLR4, CD14, Complement factor B, and Vimentin mRNA expression levels using the following formula:

$(0.52*\ln CD3\epsilon)+(1.02*\ln CD105)+(0.81*\ln TLR4)+(-1.16*\ln CD14)+(0.28*\ln \text{Complement Factor B})+(-0.79*\ln \text{Vimentin})$; and identifying a subject whose test urinary cell sample has a six-gene diagnostic signature of greater than −0.24 as having an increased likelihood that the transplanted kidney is undergoing acute rejection; or identifying a subject whose test urinary cell sample has a six-gene diagnostic signature of less than −0.24 as having an increased likelihood of acute tubular injury of a kidney transplant in the subject.

2. The method of claim 1, wherein the method distinguishes subjects undergoing acute rejection from subjects with acute tubular injury.

3. The method of claim 1, further comprising treatment of a subject for acute rejection of a kidney transplant with a six-gene diagnostic signature greater than −0.24.

4. The method of claim 1, further comprising treatment of a subject for acute tubular injury with a six-gene diagnostic signature less than −0.24.

* * * * *